United States Patent
Chee et al.

(10) Patent No.: US 9,879,313 B2
(45) Date of Patent: Jan. 30, 2018

(54) METHODS AND SYSTEMS FOR DETERMINING SPATIAL PATTERNS OF BIOLOGICAL TARGETS IN A SAMPLE

(71) Applicant: Prognosys Biosciences, Inc., San Diego, CA (US)

(72) Inventors: Mark S. Chee, San Diego, CA (US); David A. Routenberg, San Diego, CA (US)

(73) Assignee: Prognosys Biosciences, Inc., San Diego, CA (US)

( * ) Notice: Subject to any disclaimer, the term of this patent is extended or adjusted under 35 U.S.C. 154(b) by 0 days.

(21) Appl. No.: 14/900,604

(22) PCT Filed: Jun. 25, 2014

(86) PCT No.: PCT/US2014/044196
§ 371 (c)(1),
(2) Date: Dec. 21, 2015

(87) PCT Pub. No.: WO2014/210225
PCT Pub. Date: Dec. 31, 2014

(65) Prior Publication Data
US 2016/0138091 A1 May 19, 2016

Related U.S. Application Data

(60) Provisional application No. 61/839,320, filed on Jun. 25, 2013, provisional application No. 61/839,313, filed on Jun. 25, 2013.

(51) Int. Cl.
G01N 33/53 (2006.01)
C12Q 1/68 (2006.01)
B01L 3/00 (2006.01)

(52) U.S. Cl.
CPC .......... *C12Q 1/6809* (2013.01); *B01L 3/5027* (2013.01)

(58) Field of Classification Search
CPC . C12Q 1/68; C12M 1/34; C07H 21/02; C07H 21/04; C40B 30/04
See application file for complete search history.

(56) References Cited

U.S. PATENT DOCUMENTS 5,002,882 A 3/1991 Lunnen et al.
5,512,439 A 4/1996 Hornes et al.
(Continued)

FOREIGN PATENT DOCUMENTS

EP 1712623 10/2006
JP 2011-182702 6/2011
(Continued)

OTHER PUBLICATIONS

Office Action for U.S. Appl. No. 13/266,568, dated Mar. 29, 2013.
(Continued)

*Primary Examiner* — Narayan Bhat
(74) *Attorney, Agent, or Firm* — Morrison & Foerster LLP

(57) ABSTRACT

The present disclosure provides methods and assay systems for use in spatially encoded biological assays, including assays to determine a spatial pattern of abundance, expression, and/or activity of one or more biological targets across multiple sites in a sample. In particular, the biological targets comprise proteins, and the methods and assay systems do not depend on imaging techniques for the spatial information of the targets. The present disclosure provides methods and assay systems capable of high levels of multiplexing where reagents are provided to a biological sample in order to address tag the sites to which reagents are delivered; instrumentation capable of controlled delivery of reagents;

(Continued)

and a decoding scheme providing a readout that is digital in nature.

30 Claims, 13 Drawing Sheets

(56) References Cited

U.S. PATENT DOCUMENTS

| | | |
|---|---|---|
| 6,210,894 B1 | 4/2001 | Brennan |
| 6,258,558 B1 | 7/2001 | Szostak et al. |
| 6,261,804 B1 | 7/2001 | Szostak et al. |
| 6,281,804 B1 | 8/2001 | Haller et al. |
| 6,344,316 B1 | 2/2002 | Lockhart et al. |
| 6,416,950 B1 | 7/2002 | Lohse et al. |
| 6,485,982 B1 | 11/2002 | Charlton |
| 6,518,018 B1 | 2/2003 | Szostak et al. |
| 6,579,695 B1 | 6/2003 | Lambalot et al. |
| 6,632,641 B1 | 10/2003 | Brennan et al. |
| 6,800,453 B2 | 10/2004 | LaBaer et al. |
| 6,878,515 B1 | 4/2005 | Landegren et al. |
| 7,118,883 B2 | 10/2006 | Inoue et al. |
| 7,192,735 B2 | 3/2007 | Lambalot et al. |
| 7,229,769 B2 | 6/2007 | Kozlov et al. |
| 7,270,950 B2 | 9/2007 | Szostak et al. |
| 7,378,242 B2 | 5/2008 | Hurt et al. |
| 7,393,665 B2 | 7/2008 | Brenner |
| 7,407,757 B2 | 8/2008 | Brenner |
| 7,537,897 B2 | 5/2009 | Brenner |
| 7,544,473 B2 | 6/2009 | Brenner |
| 7,579,153 B2 | 8/2009 | Brenner |
| 7,635,566 B2 | 12/2009 | Brenner |
| 7,666,612 B2 | 2/2010 | Johnsson et al. |
| 7,674,752 B2 | 3/2010 | He et al. |
| 7,776,547 B2 | 8/2010 | Roth |
| 7,858,321 B2 | 12/2010 | Glezer et al. |
| 8,207,093 B2 | 6/2012 | Szostak et al. |
| 8,337,851 B2 | 12/2012 | Aukerman |
| 8,343,500 B2 | 1/2013 | Wraith |
| 9,085,798 B2 | 7/2015 | Chee |
| 2003/0087232 A1 | 5/2003 | Christians et al. |
| 2003/0096323 A1 | 5/2003 | James |
| 2003/0113713 A1 | 6/2003 | Glezer et al. |
| 2003/0232382 A1 | 6/2003 | Brennan et al. |
| 2003/0138879 A1 | 7/2003 | Lambalot et al. |
| 2003/0162216 A1 | 8/2003 | Gold et al. |
| 2003/0224419 A1 | 12/2003 | Corcoran et al. |
| 2003/0235852 A1 | 12/2003 | Roberts et al. |
| 2004/0112442 A1 | 6/2004 | Maerkl |
| 2005/0003431 A1 | 1/2005 | Wucherpfennig |
| 2005/0026188 A1 | 2/2005 | Van Kessel et al. |
| 2005/0048580 A1 | 3/2005 | LaBaer et al. |
| 2005/0164292 A1 | 7/2005 | Faroqui et al. |
| 2005/0255548 A1 | 11/2005 | Lipovsek et al. |
| 2005/0260653 A1 | 11/2005 | LaBaer et al. |
| 2006/0003394 A1 | 1/2006 | Song et al. |
| 2006/0046313 A1 | 3/2006 | Roth et al. |
| 2006/0134669 A1 | 6/2006 | Casasanta, III |
| 2006/0199207 A1 | 9/2006 | Matysiak |
| 2006/0216721 A1 | 9/2006 | Kozlov et al. |
| 2006/0216775 A1 | 9/2006 | Burkhart et al. |
| 2006/0228758 A1 | 10/2006 | Muchhal |
| 2006/0275799 A1 | 12/2006 | Banerjee et al. |
| 2007/0014810 A1 | 1/2007 | Baker et al. |
| 2007/0020625 A1 | 1/2007 | Duchaud et al. |
| 2007/0020669 A1 | 1/2007 | Olof |
| 2007/0026430 A1 | 2/2007 | Andersen et al. |
| 2007/0172873 A1 | 7/2007 | Brenner et al. |
| 2008/0071071 A1 | 3/2008 | LaBaer et al. |
| 2008/0108804 A1 | 5/2008 | Hayashizaki et al. |
| 2008/0220981 A1 | 9/2008 | McGregor |
| 2008/0293591 A1 | 11/2008 | Taussig et al. |
| 2008/0312103 A1 | 12/2008 | Nemoto et al. |
| 2009/0280487 A1 | 11/2009 | Hung et al. |
| 2009/0291854 A1 | 11/2009 | Weisinger-Mayr et al. |
| 2010/0069263 A1 | 3/2010 | Shendure et al. |
| 2010/0099103 A1 | 4/2010 | Hsieh et al. |
| 2010/0113302 A1 | 6/2010 | Williams |
| 2010/0159446 A1 | 6/2010 | Haff |
| 2010/0173384 A1 | 7/2010 | Johnsson et al. |
| 2010/0184614 A1 | 7/2010 | Ye et al. |
| 2011/0245101 A1 | 10/2011 | Chee et al. |
| 2011/0245111 A1* | 10/2011 | Chee .................... C12Q 1/6837 506/35 |
| 2012/0065081 A1 | 3/2012 | Chee |
| 2012/0129248 A1 | 5/2012 | Chee et al. |
| 2012/0195810 A1 | 8/2012 | Cohen |
| 2012/0258871 A1 | 10/2012 | Kozlov et al. |
| 2012/0270748 A1 | 10/2012 | Chee et al. |
| 2013/0096033 A1 | 4/2013 | Routenberg |
| 2013/0109595 A1 | 5/2013 | Routenberg |
| 2013/0296174 A1* | 11/2013 | Peumans ............... B01L 3/5027 506/2 |
| 2015/0087027 A1* | 3/2015 | Makarov ................ C12P 19/34 435/91.3 |
| 2016/0024576 A1 | 1/2016 | Chee |
| 2016/0333403 A1 | 11/2016 | Chee |
| 2017/0058339 A1 | 3/2017 | Chee |
| 2017/0058340 A1 | 3/2017 | Chee |
| 2017/0058345 A1 | 3/2017 | Chee |
| 2017/0088881 A1 | 3/2017 | Chee |

FOREIGN PATENT DOCUMENTS

| | | |
|---|---|---|
| WO | WO 2003/010176 | 2/2003 |
| WO | WO 2004/028955 | 4/2004 |
| WO | WO 2005/026387 | 3/2005 |
| WO | WO 2006/117541 | 11/2006 |
| WO | WO 2007/041689 | 4/2007 |
| WO | WO 2007/060599 | 5/2007 |
| WO | WO 2007/073171 | 6/2007 |
| WO | WO 2007/076726 | 7/2007 |
| WO | WO 2007/145612 | 12/2007 |
| WO | WO 2009/032167 | 3/2009 |
| WO | WO 2010/019826 | 2/2010 |
| WO | WO 2010/027870 | 3/2010 |
| WO | WO 2010/127186 | 11/2010 |
| WO | WO 2011/014879 | 2/2011 |
| WO | WO 2011/071943 | 6/2011 |
| WO | WO 2011/127006 | 10/2011 |
| WO | WO 2011/127099 | 10/2011 |
| WO | WO 2012/022975 | 2/2012 |
| WO | WO 2012/071428 | 5/2012 |
| WO | WO 2012/139110 | 10/2012 |
| WO | WO /2014/210223 | 12/2014 |
| WO | WO /2014/210225 | 12/2014 |

OTHER PUBLICATIONS

Response to Office Action for U.S. Appl. No. 13/266,568, filed Aug. 29, 2013.

Final Office Action for U.S. Appl. No. 13/266,568, dated Dec. 5, 2013.

Response After Final Office Action for U.S. Appl. No. 13/266,568, filed Mar. 4, 2014.

Office Action for U.S. Appl. No. 13/266,568, dated Mar. 26, 2014.

Response to Office Action for U.S. Appl. No. 13/266,568, filed Jun. 26, 2014.

Non-final Office Action in U.S. Appl. No. 14/723,332, dated Feb. 23, 2016.

Final Office Action in U.S. Appl. No. 14/723,332, dated Nov. 29, 2016.

Non-final Office Action in U.S. Appl. No. 14/723,332, dated Mar. 28, 2017.

Non-final Office Action in U.S. Appl. No. 15/224,253, dated Dec. 9, 2016.

Non-final Office Action in U.S. Appl. No. 15/224,253, dated May 18, 2017.

Final Office Action in U.S. Appl. No. 15/224,253, dated Jul. 3, 2017.

Office Action for U.S. Appl. No. 13/388,229, dated Dec. 24, 2012.

(56) References Cited

OTHER PUBLICATIONS

International Search Report and Written Opinion for PCT/US2010/033064, dated Jul. 30, 2010.
International Preliminary Report on Patentability Chapter I for PCT/US2010/033064, dated Nov. 1, 2011.
International Search Report and Written Opinion for PCT/US2010/044134, dated Mar. 18, 2011.
International Preliminary Report on Patentability Chapter I for PCT/US2010/044134, dated Jan. 31, 2012.
Patent Examination Report No. 1 for AU 2010278710, dated Feb. 11, 2014.
Communication Pursuant to Art. 94(3) EPC for EP 10747097.3-1405, dated Jul. 26, 2013.
Restriction Requirement for U.S. Appl. No. 13/514,045, dated Nov. 23, 2012.
Response to Restriction Requirement for U.S. Appl. No. 13/514,045, filed Dec. 19, 2012.
Office Action for U.S. Appl. No. 13/514,045, dated Feb. 21, 2013.
Response to Office Action for U.S. Appl. No. 13/514,045, filed Jun. 17, 2013.
Response to Office Action for U.S. Appl. No. 13/514,045, filed Jun. 27, 2013.
Final Office Action for U.S. Appl. No. 13/514,045, dated Oct. 18, 2013.
International Search Report and Written Opinion for PCT/US2010/059327, dated Mar. 29, 2011.
International Preliminary Report on Patentability Chapter I for PCT/US2010/059327, dated Jun. 12, 2012.
Patent Examination Report No. 1 for AU 2010328226, dated May 9, 2013.
First Office Action for CN 201080055351.2, dated Jul. 23, 2013.
Supplemental European Search Report for EP 10836568.5-1403, dated Feb. 13, 2013.
Response to Supplemental European Search Report for EP 10836568.5-1403, filed Sep. 10, 2013.
Communication Pursuant to Art. 94(3) EPC for EP 10836568.5-1403, dated Mar. 12, 2014.
First Examination Report for EP 10836568.5-1403, dated Oct. 1, 2013.
Response to First Examination Report for EP 10836568.5-1403, filed Feb. 17, 2014.
Response to Examination Report for EP 10836568.5-1403, dated Jul. 10, 2014.
Restriction Requirement for U.S. Appl. No. 13/080,616, dated Dec. 17, 2013.
Response to Restriction Requirement for U.S. Appl. No. 13/080,616, filed Jan. 16, 2014.
Office Action for U.S. Appl. No. 13/080,616, dated Apr. 9, 2014.
Response to Office Action for U.S. Appl. No. 13/080,616, filed Aug. 11, 2014.
Final Office Action for U.S. Appl. No. 13/080,616, dated Oct. 21, 2014.
Response to final Office Action for U.S. Appl. No. 13/080,616, filed Feb. 23, 2015.
Advisory Action for U.S. Appl. No. 13/080,616, dated Mar. 17, 2015.
International Search Report and Written Opinion for PCT/US2011/031308, dated Jun. 7, 2011.
International Preliminary Report on Patentability Chapter I for PCT/US2011/031308, dated Oct. 9, 2012.
Patent Examination Report No. 1 for AU 2011237729, dated Jul. 9, 2013.
Response to Patent Examination Report No. 1 for AU 2011237729, filed Mar. 3, 2014.
Patent Examination Report No. 1 for AU 2014203638, dated Oct. 1, 2015.
Office Action for CA 2794522, dated May 22, 2014.
Response to Office Action for CA 2794522, dated Sep. 17, 2014.
Voluntary Amendment and Observation for CN 201180017696.3, filed Jul. 25, 2013.
First Examination Report for CN 201180017696.3, dated Oct. 18, 2013.
Second Examination Report for CN 201180017696.3, dated Jul. 3, 2014.
Response to First Examination Report for CN 201180017696.3, filed Mar. 3, 2014.
Response to Second Examination Report for CN 201180017696.3, filed Sep. 17, 2014.
Third Examination Report for CN 201180017696.3, dated Jan. 27, 2015.
Response to Third Examination Report for CN 201180017696.3, filed Apr. 13, 2015.
Rule 161/162 Communication for EP 11766613.1, dated Nov. 14, 2012.
Response to Rule 161/162 Communication for EP 11766613.1, filed May 17, 2013.
European Search Report for EP 11766613.1, dated Jan. 15, 2014.
Response to European Search Report for EP 11766613.1, filed Jul. 11, 2014.
European Examination Report for EP 11766613.1, dated Aug. 22, 2014.
Response to European Examination Report for EP 11766613.1, filed Jan. 8, 2015.
Office Action for U.S. Appl. No. 13/079,878, dated Aug. 13, 2012.
International Search Report and Written Opinion for PCT/US2011/031163, dated May 23, 2011.
International Preliminary Report on Patentability Chapter I for PCT/US2011/031163, dated Oct. 9, 2012.
Restriction Requirement for U.S. Appl. No. 13/442,637, dated May 17, 2012.
Response to Restriction Requirement for U.S. Appl. No. 13/442,637, filed Jun. 5, 2012.
Supplemental Response and Amendment for U.S. Appl. No. 13/442,637, filed Jun. 6, 2012.
Office Action for U.S. Appl. No. 13/442,637, dated Aug. 9, 2012.
Response to Office Action for U.S. Appl. No. 13/442,637, filed Oct. 9, 2012.
Final Office Action for U.S. Appl. No. 13/442,637, dated Dec. 20, 2012.
Response to Final Office Action for U.S. Appl. No. 13/442,637, filed Mar. 20, 2013.
Advisory Action for U.S. Appl. No. 13/442,637, dated Apr. 1, 2013.
Preliminary Amendment and remarks with filing of RCE for U.S. Appl. No. 13/442,637, filed Apr. 17, 2013.
Office Action for U.S. Appl. No. 13/442,637, dated Jan. 22, 2015.
Office Action for U.S. Appl. No. 13/442,637, dated Oct. 8, 2015.
Preliminary Amendment for U.S. Appl. No. 14/068,921, filed Nov. 22, 2013.
Non-final Office Action in U.S. Appl. No. 14/068,921, dated Jun. 29, 2015.
Final Office Action in U.S. Appl. No. 14/068,921, dated Mar. 1, 2016.
Non-final Office Action in U.S. Appl. No. 14/068,921, dated May 8, 2017.
International Search Report and Written Opinion for PCT/US20120/032759, dated Sep. 28, 2012.
International Preliminary Report on Patentability Chapter I for PCT/US2012/032759, dated Oct. 8, 2013.
Invitation to Pay Additional Fees and, Where Applicable, Protest Fee for PCT/US2012/032759, dated Jul. 16, 2012.
Extended European Search Report for EP 12767937.1-1403, dated Nov. 18, 2014.
Extended European Search Report for EP 16183356.1, dated Apr. 24, 2017.
International Search Report and Written Opinion of PCT/US14/29691, dated Aug. 19, 2014.
Restriction Requirement in U.S. Appl. No. 14/776,537, dated Jan. 6, 2017.
Non-final Office Action in U.S. Appl. No. 14/776,537, dated May 2, 2017.
First Examination Report in CN 201480028069.3, dated Aug. 26, 2016 (English translation).

(56) References Cited

OTHER PUBLICATIONS

Second Examination Report in CN 201480028069.3, dated Jul. 10, 2017 (English translation).
Extended European Search Report for EP 14765026.1, dated Sep. 26, 2016.
International Search Report and Written Opinion of PCT/US14/44191, dated Nov. 7, 2014.
Non-final Office Action in U.S. Appl. No. 14/900,602, dated Jan. 9, 2017.
Extended European Search Report for EP 14816674.7, dated Feb. 3, 2017.
International Search Report and Written Opinion of PCT/US14/44196, dated Nov. 7, 2014.
Extended European Search Report for EP 14818012.8, dated Feb. 3, 2017.
International Search Report and Written Opinion of PCT/US14/64588, dated Mar. 11, 2015.
Non-final Office Action in U.S. Appl. No. 15/035,206, dated Jun. 30, 2017.
Valencia et al., "mRNA-display-based selections for proteins with desired functions: A protease-substrate case study," Biotechnology Progress, 2008, 24(3): 561-569.
Anderson et al., "Microarrayed Compound Screening to Identify Activators and Inhibitors of AMP-Activated Protein Kinase," J. of Biomolecular Screening (2004) 9:112 POI: 0.1177/1087057103260592.
Angenendt et al., "Cell-free expression and functional assay in a nanowell chip format," Analytical Chemistry (2004) 76(7):1844-49.
Angenendt et al.,"Generation of High Density Protein Microarrays by Cell-free in Situ Expression of Unpurified PCR Products," Molecular and Cellular Proteomics (2006) Ch. 5.9, pp. 1658-1666.
Atkinson, Overview of Translation: Lecture Manuscript, U of Texas (2000) pp. 6.1-6.8.
Blokzijl et al., "Profiling protein expression and interactions: proximity ligation as a tool for personalized medicine," J Intern Med (2010) 268:232-245.
Burns et al., "Well-less, gel-permeation formats for ultra-HTS," DDT (2001) 6(12):S40-S47.
Carlson et al., "Formylglycine-generating Enzyme," J. of Biological Chemistry (2008) 283(29):20117-125.
Cerutti et al., "Generation of sequence-specific, high affinity anti-DNA antibodies," Journal of Biological Chemistry (2001) 276(16):12769-12773.
Cha et al., "Specificity, Efficiency and Fidelity of PCR," Genome Res. (1993) 3:518-29.
Chandra et al., "Cell-free synthesis-based protein microarrays and their applications," Proteomics ePub (2009) 5(6):717-30.
Chatterjee et al., "Protein Microarray On-Demand: A Novel Protein Microarray System," PLos One (2008) 3(9):e3265.
Chen et al., "DNA hybridization detection in a microfluidic Channel using two fluorescently labelled nucleic acid probes", Biosensors and Bioelectronics (2008) 23:1878-1882.
Cheng et al., "Sensitive Detection of Small Molecules by Competitive Immunomagnetic-Proximity Ligation Assay," Anal Chem (2012) 84:2129-2132.
Condina et al., "A sensitive magnetic bead method for the detection and identification of tyrosine phosphorylation in proteins by MALDI-TOF/TOF MS," Proteomics (2009) 9:3047-3057.
Cujec et al. "Selection of v-abl tyrosine kinase substate sequences from randomnized peptide and cellular proteomic libraries using mRNA display," Chemistry and Biology (2002) 9:253-264.
Darmanis, et al.,"ProteinSeq: High-Performance Proteomic Analyses by Proximity, Ligation and Next Generation Sequencing", PLos One (2011) 6(9):e25583 doi1 0.1371/journal.pone.0025583 20 1.
Eldridge et al. "An in vitro selection strategy for conferring protease resistance to ligand binding peptides," Protein Eng Des Sel (2009) 22(11):691-698.
Ellington et al., "Antibody-based protein multiplex platforms: technical and operational challenges," Clin Chem (2010) 56(2):186-193.
Flanigon et al., "Multiplex protein detection with DNA readout via mass spectrometry," N Biotechnol (2013) 30(2):153-158.
Fredriksson et al., "Protein detection using proximity-dependent DNA ligation assays," Nature Biotech. (2002) 20:473-77.
Fredriksson et al., "Multiplexed protein detection by proximity ligation for cancer biomarker validation," Nature Methods (2007) 4(4):327-29.
Fredriksson et al., "Multiplexed proximity ligation assays to profile putative plasma biomarkers relevant to pancreatic and ovarian cancer," Clin. Chem. (2008) 5(3): 582-89.
Frese et al., "Formylglycine Aldehyde Tag-Protein Engineering through a Novel Post-translational Modification," ChemBioChem (2009) 10:425-27.
Fu et al., "Counting individual DNA molecules by the stochastic attachment of diverse labels," PNAS (2011) 108:9026-9031.
Gu et al., "Protein tag-mediated conjugation of oligonucleotides to recombinant affinity binders for proximity ligation," N Biotechnol (2013) 30(2):144-152.
Hammond et al., "Profiling cellular protein complexes by proximity ligation with dual tag microarray readout," (2012) 7(7):e40405.
He et al., "In situ synthesis of protein arrays," Current Opinion in Biotechnology (2008) 19:4-9.
He et al., "In situ synthesis of protein arrays," Current Opinion in Biotechnology (2008)19:4-9 Supplementary figures.
He, "Cell-free protein synthesis: applications in proteomics and biotechnology," New Biotechnology (2008) 25:126-132.
He et al., "Printing protein arrays from DNA arrays," Nature Methods (2008) 5:175-77.
Hedskog et al., "Dynamics of HIV-1 Quasispecies during Antiviral Treatment Dissected using Ultra-Deep Pyrosequencing," PLoS One (2010) 5(7):e11345.
Hendrickson et al., "High sensitivity multianalyte immunoassay using covalent DNA-labeled antibodies and polymerase chain reaction," Nucl. Acid Res. (1995) 23(9):522-29.
Hiatt et al., "Parallel, tag-directed assembly of locally-derived short sequence reads," Nature Methods (2010) 7(2):119-25.
Mir et al., "Sequencing by cyclic ligation and cleavage (CycLiC) directly on a microarray captured template," Nucleic Acids Research (2009) 37(1):e5-1.
Kozlov et al., "A Method for Rapid Protease Substrate Evaluation and Optimization," Comb. Chem. and High Throughput (2006) 9:481-87.
Kozlov et al., "A High-Complexity Multiplexed Solution-Phase Assay for Profiling Protease Activity on Microarrays," Comb. Chem. and High Throughput (2008) 11:24-35.
Kozlov et al., "A Highly Scalable Peptide-Based Assay System for Proteomics," PLoS ONE (2012) 7(6):e37441.
Kurz et al., "eDNA-Protein Fusions: Covalent Protein-Gene Conjugates for the In Vitro Selection of Peptides and Proteins," ChemBioChem (2001) 2:666-72.
Larman et al., "Autoantigen discovery with a synthetic human peptidome", Nature Biotechnology (2011) doi:1 0.1038/nbt.1856.
Lundberg et al., "Multiplexed homogeneous proximity ligation assays for high-throughput protein biomarker research in serological material," Mol Cell Proteomics (2011) 10(4):M110.004978.
Lundberg et al., "Homogeneous antibody-based proximity extension assays provide sensitive and specific detection of low-abundant proteins in human blood", Nucleic Acids Res (2011) 39(15):e102 (Abstract).
Mizusawa et al., "A bacteriophage lambda vector for cloning with BamHI and Sau3A," Gene (1982) 20:317-322.
Ng et al., "Massively parallel sequencing and rare disease," Human Molec. Genetics (2010) 19(2):R119-R124.
Niemeyer., "The developments of semisynthetic DNA/protein conjugates," Trends Biotechnol (2002) 20(9):395-401.
Oleinikov et al. "Self-assembling protein arrays using electronic semiconductor microchips and in vitro translation," Journal of Proteome Research (2003) 2:313-319.
Osada et al., "Epitope mapping using ribosome display in a reconstituted cell-free protein synthesis system," Journal of Biochemistry, 2009, 145(5):693-700.

(56) References Cited

OTHER PUBLICATIONS

O'Shannessy et al., "Detection and Quantitation of Hexa-Histidine-Tagged recombinant proteins on western blots and by a surface plasmon resonance biosensor technique," Analytical Biochemistry (1995) 229:119-124.
Proseek® Multiplex 96×96 User Manual (2013) Olink Bioscience, Uppsala, Sweden, 20 pages.
Ramachandran et al., "Next-generation high-density self-assembling functional protein arrays," Nature Methods (2008) 5(6):535-38.
Roberts et al., "RNA-peptide fusions for the in vitro selection of peptides and proteins," PNAS USA (1997) 94:12297-302.
Rouillard et al., "OligoArray 2.0: design of oligonucleotide probes for DNA microarrays using a thermodynamic approach," Nuc. Acid Research (2003) 31 (12):3057-62.
Rountenberg et al., "Microfluidic probe: a new tool for integrating microfluidic environments and electronic wafer-probing," Lab Chip, Oct. 29, 2009, 10: 123-127.
Rush et al., "New Aldehyde Tag Sequences Identified by Screening Formylglycine Generating Enzymes in Vitro and in Vivo," J. of American Chemical Society (2008) 130: 12240-41.
Rush et al., "New Aldehyde Tag Sequences Identified by Screening Formylglycine Generating Enzymes in Vitro and in Vivo," J. of American Chemical Society (2008) 130: 12240-41 (2008) Supplement.
Schmitt et al., "Detection of ultra-rare mutations by next-generation sequencing," PNAS (2012) 109:14508-14523.
Sergeeva et al., "Display technologies: Application for the discovery of drug and gene delivery agents," Advanced Drug Delivery Reviews (2006) 58(15):1622-1654.
Shoemaker et al., "Quantitative phenotypic analysis of yeast deletion mutants using a highly parallel molecular bar-coding strategy," Nature genetics (1996) 14:450-456.
Shults et al., "A multiplexed protein kinase assay," Chem Bio Chem (2007) 8:933-942.
Tian et al., "Antigen peptide-based immunosensors for rapid detection of antibodies and antigens," Anal Chem (2009) 81:5218-5225.
Tolbert et al., "New Methods for Proteomic Research: Preparation of Proteins with N-Terminal Cysteines for Labeling and Conjugation," Angew. Chem. Int. Ed. (2002) 41 (12):2171-2174.
Takahashi et al., "In Vitro Selection of Protein and Peptide Libraries Using mRNA Display," Nucleic Acid and Peptide Aptamers: Methods and Protocols (2009) 535:293-314 (Ch.17).
Vogelstein et al., "Digital PCR," PNAS USA (1999) 96:9236-9241.
Waichman et al., "Functional Immobilization and Patterning of Proteins by an Enzymatic Transfer Reaction," Anal. Chem (2010) 82:1478-1785.
Weichhart et al., "Functional selection of vaccine candidate peptides from *Staphylococcus aureus* whole-genome expression libraries in vitro," Infection and Immunity, 2003, 71(8):4333-4641.
Wong et al., "Direct Site-Selective Covalent Protein Immobilization Catalyzed by a Phosphopantetheinyl Transferase," J. Am. Chem Soc. (2008) 130:12456-64.
Worthington et al., "Cloning of random oligonucleotides to create single-insert plasmid libraries," Analyt. Biochem (2001) 294:169-175.
Xiao et al., "Direct determination of haplotypes from single DNA molecules," Nature Methods (2009) 6(3):199-01.
Yin et al., "Genetically encoded short peptide tag for versatile protein labeling by Sfp phosphopantetheinyl transferase," PNAS (2005) 102(44):15815-20.
Yonezawa et al., "DNA display for in vitro selection of diverse peptide libraries", Nucleic Acids Research (2003) 31(19):e118.
Zhang et al., "Assembling DNA through Affinity Binding to Achieve Ultrasensitive Protein Detection," Angew Chem Int Ed (2013) 52:2-10.
Zhang et al., "Binding-induced DNA assembly and its application to yoctomole detection of proteins," Anal Chem (2012) 84(2):877-884.
Zhou et al., "Genetically Encoded Short Peptide Tags for Orthogonal Protein Labeling by Sfp and AcpS Phosphopentetheinyl Transferases," ACS Chemical Biology (2007) 2(5): 337-346.
Zlobec et al., "Next-generation tissue microarray (ngTMA) increases the quality of biomarker studies: an example using CD3, CD8, and CD45RO in the tumor microenvironment of six different solid tumor types," Journal of Translational Medicine (2013) 11:104.

\* cited by examiner

Figure 6
D
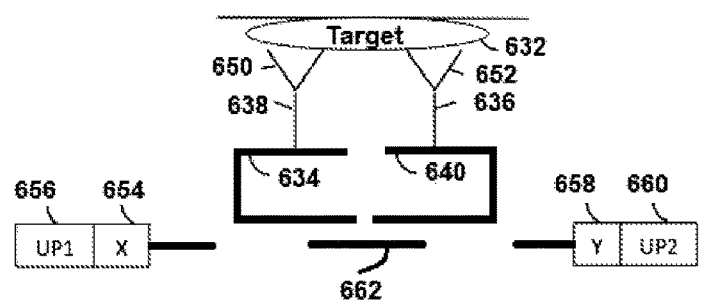
E
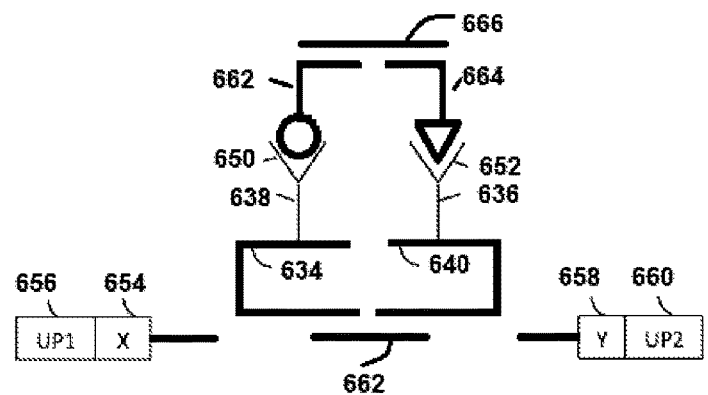

Figure 8
A
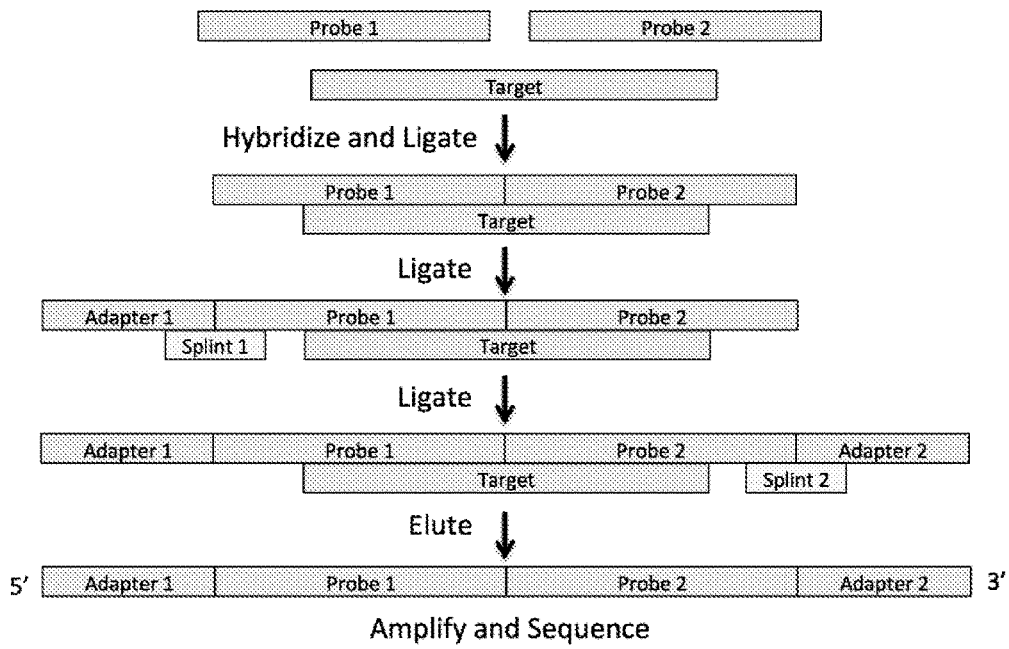
B
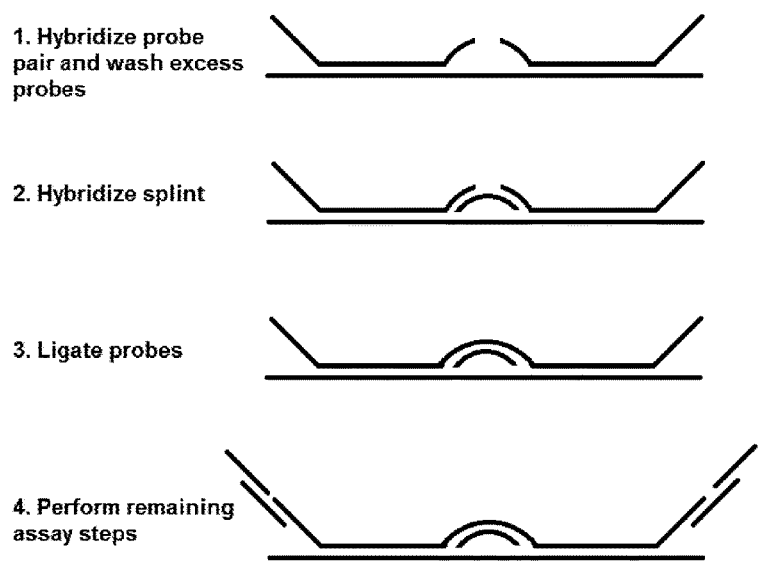

Figure 11
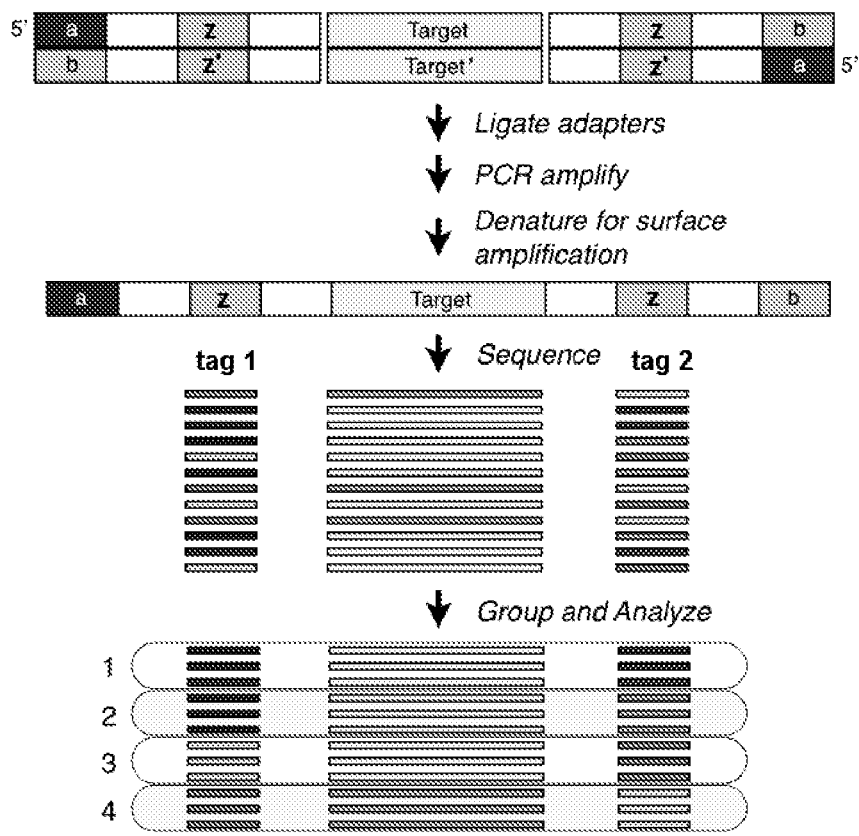

METHODS AND SYSTEMS FOR DETERMINING SPATIAL PATTERNS OF BIOLOGICAL TARGETS IN A SAMPLE

RELATED APPLICATIONS

This application is a national phase of International Application No. PCT/US2014/044196, filed Jun. 25, 2014, which claims benefit of priority to U.S. Provisional Patent Application Ser. No. 61/839,320, filed Jun. 25, 2013, entitled "Spatially encoded biological assays using a microfluidic device," and U.S. Provisional Patent Application Ser. No. 61/839,313, filed Jun. 25, 2013, entitled "Methods and systems for determining spatial patterns of biological targets in a sample," the disclosures of which are incorporated by reference herein in their entireties. In some embodiments, this application is related to International Application No. PCT/US2014/044191, filed Jun. 25, 2014, entitled "Spatially encoded biological assays using a microfluidic device," the disclosure of which is incorporated by reference herein in its entirety.

STATEMENT REGARDING FEDERALLY SPONSORED RESEARCH OR DEVELOPMENT

This invention was made with the support by the Department of Health and Human Services, National Institute of General Medical Sciences Grant Number R43GM096706, and National Human Genome Research Institute Grant Number R43HG006223. The U.S. government may have certain rights in this invention.

TECHNICAL FIELD

The present disclosure generally relates to assays of biological molecules, and in particular, to methods, compositions, and assay systems for determining spatial patterns of abundance, expression, and/or activity of one or more biological targets across multiple sites in a sample.

BACKGROUND

In the following discussion, certain articles and methods are described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Comprehensive gene expression analysis and protein analysis have been useful tools in understanding mechanisms of biology. Use of these tools has allowed the identification of genes and proteins involved in development and in various diseases such as cancer and autoimmune disease. Conventional methods such as in situ hybridization and other multiplexed detection of different transcripts have revealed spatial patterns of gene expression and have helped shed light on the molecular basis of development and disease. Other technologies that have enabled the quantitative analysis of many RNA sequences per sample include microarrays (see Shi et al., Nature Biotechnology, 24(9): 1151-61 (2006); and Slonim and Yanai, Plos Computational Biology, 5(10):e1000543 (2009)); serial analysis of gene expression (SAGE) (see Velculescu et al., Science, 270 (5235):484-87 (1995)); high-throughput implementations of qPCR (see Spurgeon et al., Plos ONE, 3(2):e1662 (2008)); in situ PCR (see Nuovo, Genome Res., 4:151-67 (1995)); and RNA-Seq (see Mortazavi et al., Nature Methods, 5(7): 621-8 (2008)). As useful as these methods are, however, they do not enable simultaneous measurement of the expression of many genes or the presence and/or activity of multiple proteins at many spatial locations in a sample.

Laser capture microdissection has permitted the analysis of many genes at a small number of locations, but it is very expensive, laborious, and does not scale well. Certain PCR assays in a 2D format preserve spatial information (see Armani et al., Lab on a Chip, 9(24):3526-34 (2009)), but these methods have low spatial resolution because they rely on physically transferring tissues into wells, which also prevents random access to tissue samples and high levels of multiplexing.

At present, there is a need to analyze at high resolution the spatial expression patterns of large numbers of genes, proteins, or other biologically active molecules simultaneously. There is also a need for reproducible, high-resolution spatial maps of biological molecules in tissues. The present disclosure addresses these needs.

SUMMARY

In one aspect, disclosed herein is a method of determining a spatial pattern of abundance, expression, and/or activity of one or more biological targets across multiple sites in a sample, comprising:

delivering a probe for each of one or more biological targets to multiple sites in a sample, wherein each probe comprises: (1) a target-binding moiety capable of binding to the probe's corresponding biological target; (2) an address tag that identifies each of the multiple sites to which the probe is delivered; and (3) an identity tag that identifies the probe's corresponding biological target or target-binding moiety;

allowing each probe to bind to its corresponding biological target in the sample;

analyzing the probe bound to the one or more biological targets, the analysis comprising: (1) determining abundance, expression, and/or activity of each of the one or more biological targets by assessing the amount of the probe bound to the biological target; and (2) determining the identities of the identity tag and the address tag of the probe; and determining a spatial pattern of abundance, expression, and/or activity of the one or more biological targets across the multiple sites in the sample based on the analysis. In some embodiments, the method does not depend on an imaging technique for determining spatial information of the one or more biological targets in the sample. In one embodiment, analysis of the probe bound to the one or more biological targets can be done by sequencing, wherein the amount of a sequencing product indicates abundance, expression, and/or activity of each of the one or more biological targets, and the sequencing product may comprise all or a portion of the address tag sequence and all or a portion of the identity tag sequence.

In another aspect, disclosed herein is a method of determining a spatial pattern of abundance, expression, and/or activity of one or more biological targets across multiple sites in a sample, comprising:

delivering a probe for each of one or more biological targets to multiple sites in a sample, wherein each probe comprises: (1) a target-binding moiety capable of binding to the probe's corresponding biological target; and (2) an identity tag that identifies the probe's corresponding biological target or target-binding moiety;

allowing each probe to bind to its corresponding biological target in the sample;

delivering an address tag to each of the multiple sites in the sample, wherein the address tag is to be coupled to the probe bound to the biological target and identifies the site to which the address tag is delivered;

analyzing the probe/address tag conjugate bound to the one or more biological targets, the analysis comprising: (1) determining abundance, expression, and/or activity of each of the one or more biological targets by assessing the amount of the probe/address tag conjugate bound to the biological target; and (2) determining the identities of the identity tag and the address tag of the probe/address tag conjugate; and determining a spatial pattern of abundance, expression, and/or activity of the one or more biological targets across the multiple sites in the sample based on the analysis. In some embodiments, the method does not depend on an imaging technique for determining spatial information of the one or more biological targets in the sample. In one embodiment, the probe/address tag conjugate bound to the one or more biological targets may be analyzed by sequencing, wherein the amount of a sequencing product indicates abundance, expression, and/or activity of each of the one or more biological targets, and the sequencing product may comprise all or a portion of the address tag sequence and all or a portion of the identity tag sequence.

In any of the preceding embodiments or combinations thereof, the one or more biological targets can be non-nucleic acid molecules. In any of the preceding embodiments, the one or more biological targets may comprise a protein, a lipid, a carbohydrate, or any combination thereof. In any of the preceding embodiments, there can be at least two address tags that identify each of the multiple sites in the sample.

In any of the preceding embodiments, the spatial patterns of abundance, expression, and/or activity of multiple biological targets can be determined in parallel, and the address tag or combination of address tags may be the same for each of the multiple biological targets at a given site of the multiple sites in the sample. In any of the preceding embodiments, the analyzing step may be performed in parallel in the same reaction run.

In any of the preceding embodiments or combinations thereof, the one or more biological targets may include at least one known marker for the sample, for example, a tissue-specific marker, a cell type marker, a cell lineage marker, a cell morphology marker, a cell cycle marker, a cell death marker, a developmental stage marker, a stem cell or progenitor cell marker, a marker for a differentiated state, an epigenetic marker, a physiological or pathophysiological marker, a marker for a transformed state, a cancer marker, or any combination thereof.

In yet another embodiment, provided herein is a method of determining a spatial pattern of abundance, expression, and/or activity of a target protein across multiple sites in a sample, comprising:

delivering a probe for a target protein to multiple sites in a sample, wherein the probe comprises: (1) a target-binding moiety capable of binding to the target protein; (2) a first address tag that identifies each of the multiple sites to which the probe is delivered; and (3) an identity tag that identifies the target protein or the target-binding moiety;

allowing the probe to bind to the target protein in the sample;

analyzing the probe bound to the target protein, the analysis comprising: (1) determining abundance, expression, and/or activity of the target protein by assessing the amount of the probe bound to the target protein; and (2) determining the identities of the identity tag and the first address tag of the probe for the target protein; and determining a spatial pattern of abundance, expression, and/or activity of the target protein across the multiple sites in the sample based on the analysis.

In any of the preceding embodiments, the method may further comprise:

delivering a probe for a target polynucleotide to each of the multiple sites in the sample, wherein the probe for the target polynucleotide comprises: (1) a sequence that hybridizes to and identifies the target polynucleotide; (2) a second address tag that identifies each of the multiple sites to which the probe for the target polynucleotide is delivered;

allowing the probe for the target polynucleotide to bind to the target polynucleotide in the sample;

analyzing the probe bound to the target polynucleotide, the analysis comprising: (1) determining abundance, expression, and/or activity of the target polynucleotide by assessing the amount of the probe bound to the target polynucleotide; and (2) determining the identities of the sequence that hybridizes to and identifies the target polynucleotide and the second address tag of the probe for the target polynucleotide; and determining a spatial pattern of abundance, expression, and/or activity of the target polynucleotide across the multiple sites in the sample based on the analysis of the probe bound to the target polynucleotide at each of the multiple sites in the sample.

In another aspect, disclosed herein is a method of determining a spatial pattern of abundance, expression, and/or activity of a target protein across multiple sites in a sample, comprising:

delivering a probe for a target protein to multiple sites in the sample, wherein the probe comprises: (1) a target-binding moiety capable of binding to the target protein; and (2) an identity tag that identifies the target protein or the protein-binding moiety;

allowing the probe to bind to the target protein in the sample;

delivering a first address tag to each of the multiple sites in the sample, wherein the first address tag is to be coupled to the probe bound to the target protein and identifies the site to which it is delivered;

analyzing the probe/first address tag conjugate bound to the target protein, the analysis comprising: (1) determining abundance, expression, and/or activity of the target protein by assessing the amount of the probe/first address tag conjugate bound to the target protein; and (2) determining the identities of the identity tag and the first address tag of the probe/first address tag conjugate; and determining a spatial pattern of abundance, expression, and/or activity of the target protein across the multiple sites in the sample based on the analysis.

In any of the preceding embodiment, the method may further comprise:

delivering a probe for a target polynucleotide to each of the multiple sites in the sample, wherein the probe for the target polynucleotide comprises a sequence that hybridizes to and identifies the target polynucleotide;

allowing the probe for the target polynucleotide to bind to the target polynucleotide in the sample;

delivering a second address tag to each of the multiple sites in the sample, wherein the second address tag is to be coupled to the probe bound to the target polynucleotide and identifies the site to which it is delivered;

analyzing the probe/second address tag conjugate bound to the target polynucleotide, the analysis comprising: (1) determining abundance, expression, and/or activity of the target polynucleotide by assessing the amount of the probe/second address tag conjugate bound to the target polynucleotide; and (2) determining the identities of the sequence that hybridizes to and identifies the target polynucleotide and the second address tag of the probe/second address tag conjugate; and determining a spatial pattern of abundance, expression, and/or activity of the target polynucleotide across the multiple sites in the sample based on the analysis of the probe/second address tag conjugate bound to the target polynucleotide at each of the multiple sites in the sample.

In one embodiment, the target polynucleotide or the complement thereof may encode all or a portion of the target protein. In some embodiments, the step of analyzing the probe or probe/first address tag conjugate bound to the target protein and the step of analyzing the probe or probe/second address tag conjugate bound to the target polynucleotide may be performed in parallel in the same reaction run. In other aspects, the first address tag and the second address tag may be the same for a given site of the multiple sites in the sample. In yet other aspects, the first address tag and the second address tag can be different for a given site of the multiple sites in the sample. In any of the preceding embodiments, the method may further comprise associating abundance, expression, and/or activity of the target protein to abundance, expression, and/or activity of the target polynucleotide at each of the multiple sites in the sample.

In any of the preceding embodiments or any combinations thereof, the biological target or the target protein may comprise an enzyme activity. In certain aspects, the target-binding moiety of the probe in any of the preceding embodiments may comprise an antibody or an antigen binding fragment thereof, an aptamer, a small molecule, an enzyme substrate, a putative enzyme substrate, an affinity capture agent, or a combination thereof.

In any of the preceding embodiments or any combinations thereof, the target-binding moiety is conjugated to a polynucleotide comprising the identity tag. In any of the preceding embodiments, the target-binding moiety may be conjugated to a polynucleotide capable of specifically hybridizing to a polynucleotide comprising the identity tag. In certain aspects, the probe may comprise a multiplicity of target-binding moieties capable of binding to the same domain or different domains of the target, or capable of binding to different targets.

In any of the preceding embodiments or any combinations thereof, the sample can be a biological sample selected from the group consisting of a freshly isolated sample, a fixed sample, a frozen sample, an embedded sample, a processed sample, or a combination thereof.

In any of the preceding embodiments or any combinations thereof, there can be two address tags that identify each of the multiple sites in the sample. In certain aspects, two probes for each target can be delivered to the sample.

In any of the preceding embodiments or any combinations thereof, the address tag may comprise an oligonucleotide. In another aspect, the identity tag of any of the preceding embodiments may comprise an oligonucleotide.

In any of the preceding embodiments or any combinations thereof, the analyzing step may be performed by nucleic acid sequencing. In one aspect, the analyzing step can be performed by high-throughput digital nucleic acid sequencing.

In any of the preceding embodiments or any combinations thereof, the product of the number of the target(s) being assayed and the number of the multiple sites being assayed in the sample can be greater than 20, greater than 50, greater than 75, greater than 100, greater than 1,000, greater than 10,000, greater than 100,000, or greater than 1,000,000.

In any of the preceding embodiments or any combinations thereof, at least one hundred thousand, at least five hundred thousand, or at least one million probes or probe/address tag conjugates bound to the target(s) may be analyzed in parallel.

In any of the preceding embodiments or any combinations thereof, software programmed hardware may perform at least two steps of the delivering step(s), the analyzing step(s) and the determining step(s). In any of the preceding embodiments or any combinations thereof, one or more microfluidic devices may be used to perform the delivering step(s).

In any of the preceding embodiments or any combinations thereof, a known percentage of the probe for the biological target, the probe for the target protein, or the probe for the target polynucleotide can be an attenuator probe. In one aspect, the attenuator probe may limit production of an amplifiable product. For example, an attenuator probe may compete with an active probe for binding to the target. While an active probe can lead to the generation of an amplifiable product from the target, an attenuator probe does not or has reduced ability in generating an amplifiable product. In one embodiment where a nucleic acid probe is used, the attenuator probe can lack a 5' phosphate.

In any of the preceding embodiments or any combinations thereof, the address tag may be coupled to the probe by ligation, by extension, by ligation following extension, or any combination thereof.

In any of the preceding embodiments or any combinations thereof, the method may further comprise constructing a 3-dimensional pattern of abundance, expression, and/or activity of each target from spatial patterns of abundance, expression, and/or activity of each target of multiple samples. In one aspect, the multiple samples can be consecutive tissue sections of a 3-dimensional tissue sample.

In yet another aspect, provided herein is a system for determining a spatial pattern of abundance, expression, and/or activity of one or more biological targets across multiple sites in a sample, comprising:

a first module for delivering a probe for each of one or more biological targets to multiple sites in a sample, wherein each probe comprises: (1) a target-binding moiety capable of binding to the probe's corresponding biological target; and (2) an identity tag that identifies the probe's corresponding biological target or target-binding moiety;

a second module for delivering an address tag to each of the multiple sites in the sample, wherein the address tag is to be coupled to the probe bound to the biological target and identifies the site to which the address tag is delivered;

a third module for analyzing the probe/address tag conjugate bound to the one or more biological targets, the analysis comprising: (1) determining abundance, expression, and/or activity of the one or more biological targets by assessing the amount of the probe/address tag conjugate bound to the biological target; and (2) determining the identities of the identity tag and the address tag of the probe/address tag conjugate; and a fourth module for determining a spatial pattern of abundance, expression, and/or activity of the one or more biological targets across the multiple sites in the sample based on the analysis. In one aspect, the system does not depend on an imaging technique for determining spatial information of the one or more biological targets in the sample.

In one embodiment, the second module may comprise one or more microfluidic devices for delivering the address tags. In one aspect, the one or more microfluidic devices may comprise a first set of multiple addressing channels, each delivering a different first address tag to the sample. In one embodiment, the one or more microfluidic devices may further comprise a second set of multiple addressing channels, each delivering a different second address tag to the sample. In one aspect, the multiple sites in the sample can be chosen by the first and second set of multiple addressing channels cooperatively delivering the first address tags and the second address tags, respectively, to each of the multiple sites, each site identified by a different combination of first and second address tags.

In another embodiment, disclosed herein is a method comprising: delivering a probe for each of one or more biological targets to multiple sites in a sample, wherein each probe comprises a target-binding moiety capable of binding to the probe's corresponding biological target; allowing each probe to bind to its corresponding biological target in the sample; delivering at least one adaptor to the multiple sites in the sample, wherein the at least one adaptor specifically binds to the probe and comprises an address tag that identifies each of the multiple sites to which the at least one adaptor is delivered, wherein the probe and/or the adaptor comprises an identity tag that identifies the probe's and/or adaptor's corresponding biological target or target-binding moiety; analyzing the at least one adaptor and the probe bound to the one or more biological targets, the analysis comprising: (1) determining abundance, expression, and/or activity of each of the one or more biological targets by assessing the amount of at least one adaptor bound to the probe bound to the biological target; and (2) determining the identities of the identity tag, and the address tag of the at least one adaptor; and determining a spatial pattern of abundance and/or activity of the one or more biological targets across the multiple sites in the sample based on the analysis. In one aspect, the method does not depend on an imaging technique for determining spatial information of the one or more biological targets in the sample.

In another embodiment, disclosed herein is a method comprising: delivering a probe for each of one or more biological targets to multiple sites in a sample, wherein each probe comprises a target-binding moiety capable of binding to the probe's corresponding biological target; allowing each probe to bind to its corresponding biological target in the sample; delivering at least one adaptor to the multiple sites in the sample, wherein the at least one adaptor specifically binds to the probe and comprises an address tag that identifies each of the multiple sites to which the at least one adaptor is delivered, wherein the probe and/or the adaptor comprises an identity tag that identifies the probe's and/or adaptor's corresponding biological target or target-binding moiety; analyzing the at least one adaptor and the probe bound to the one or more biological targets by sequencing, wherein the amount of a sequencing product indicates abundance, expression, and/or activity of each of the one or more biological targets, the sequencing product comprising all or a portion of the address tag sequence and all or a portion of the identity tag sequence; and determining a spatial pattern of abundance, expression, and/or activity of the one or more biological targets across the multiple sites in the sample based on the analysis. In one aspect, the method does not depend on an imaging technique for determining spatial information of the one or more biological targets in the sample.

In yet another embodiment, provided herein is a method comprising: delivering a probe for each of one or more biological targets to multiple sites in a sample, wherein each probe comprises a target-binding moiety capable of binding to the probe's corresponding biological target; allowing each probe to bind to its corresponding biological target in the sample; delivering at least one adaptor to the multiple sites in the sample, wherein the at least one adaptor specifically binds to the probe, wherein the probe and/or the adaptor comprises an identity tag that identifies the probe's and/or adaptor's corresponding biological target or target-binding moiety; delivering an address tag to each of the multiple sites in the sample, wherein the address tag is to be coupled to the at least one adaptor bound to the probe bound to the biological target and identifies the site to which the address tag is delivered; analyzing the adaptor/address tag conjugate, the analysis comprising: (1) determining abundance, expression, and/or activity of each of the one or more biological targets by assessing the amount of the adaptor/address tag conjugate bound to the probe bound to the biological target; and (2) determining the identities of the identity tag, and the address tag of the adaptor/address tag conjugate; and determining a spatial pattern of abundance, expression, and/or activity of the one or more biological targets across the multiple sites in the sample based on the analysis. In one embodiment, the method does not depend on an imaging technique for determining spatial information of the one or more biological targets in the sample.

In still another embodiment, provided herein is a method comprising: delivering a probe for each of one or more biological targets to multiple sites in a sample, wherein each probe comprises a target-binding moiety capable of binding to the probe's corresponding biological target; allowing each probe to bind to its corresponding biological target in the sample; delivering at least one adaptor to the multiple sites in the sample, wherein the at least one adaptor specifically binds to the probe, wherein the probe and/or the adaptor comprises an identity tag that identifies the probe's and/or adaptor's corresponding biological target or target-binding moiety; delivering an address tag to each of the multiple sites in the sample, wherein the address tag is to be coupled to the at least one adaptor bound to the probe bound to the biological target and identifies the site to which the address tag is delivered; analyzing the adaptor/address tag conjugate by sequencing, wherein the amount of a sequencing product indicates abundance, expression, and/or activity of each of the one or more biological targets, the sequencing product comprising all or a portion of the address tag sequence and all or a portion of the identity tag sequence; and determining a spatial pattern of abundance, expression, and/or activity of the one or more biological targets across the multiple sites in the sample based on the analysis. In one aspect, the method does not depend on an imaging technique for determining spatial information of the one or more biological targets in the sample.

In any of the preceding embodiments, at least two adaptors can be delivered to each of the multiple sites in the sample, wherein the at least two adaptors each specifically binds to one probe that specifically binds to the biological target. In one aspect, the at least two adaptors are joined, for example, by ligation using a portion of the probe sequence as a splint.

In any of the preceding embodiments, the probe for each of the one or more biological targets can comprise an affinity agent for the biological target and an oligonucleotide, and the adaptor can comprise an oligonucleotide.

BRIEF DESCRIPTION OF THE DRAWINGS

FIG. 8 illustrates sequential address tagging schemes, according to embodiments of the present disclosure.

FIG. 11 illustrates a method for reducing random errors during the sequencing step (FIG. 11A), and exemplary configurations of probes with integrated X and Y address tags and variable tag region z (FIG. 11B), according to some embodiments of the present disclosure.

DETAILED DESCRIPTION

Figure 1:
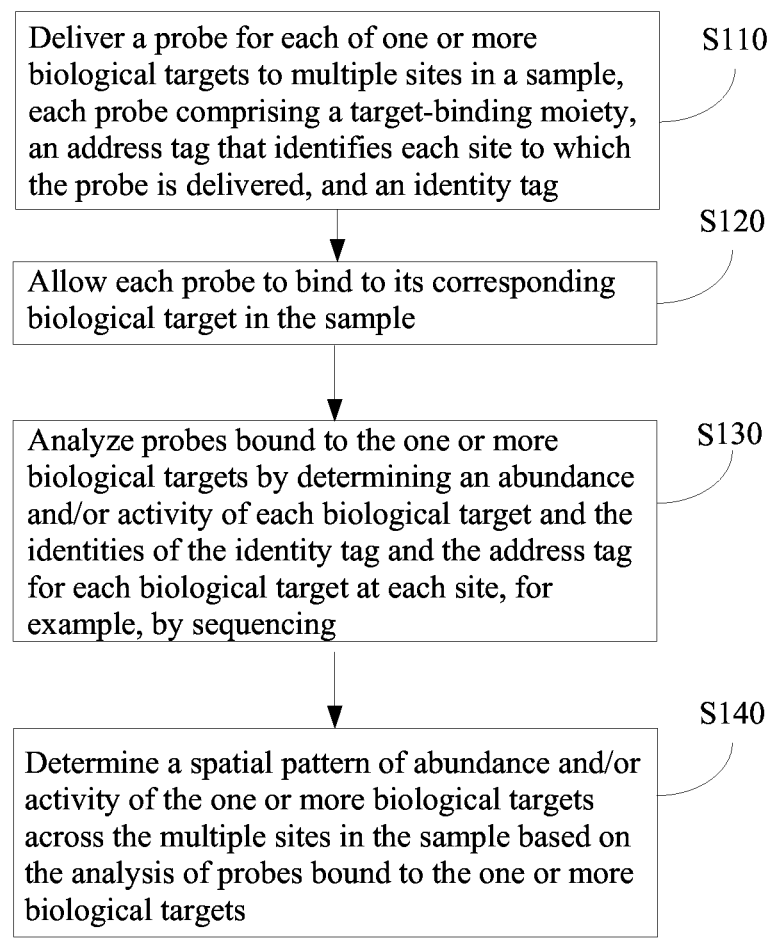
FIG. 1 is a flow chart illustrating exemplary steps of a method of determining a spatial pattern of abundance, expression, and/or activity of one or more biological targets across multiple sites in a sample, according to an embodiment of the present disclosure.

A detailed description of one or more embodiments of the claimed subject matter is provided below along with accompanying figures that illustrate the principles of the claimed subject matter. The claimed subject matter is described in connection with such embodiments, but is not limited to any embodiment. It is to be understood that the claimed subject matter may be embodied in various forms, and encompasses numerous alternatives, modifications and equivalents. Therefore, specific details disclosed herein are not to be interpreted as limiting, but rather as a basis for the claims and as a representative basis for teaching one skilled in the art to employ the claimed subject matter in virtually any appropriately detailed system, structure or manner. Numerous specific details are set forth in the following description in order to provide a thorough understanding of the present disclosure. These details are provided for the purpose of example and the claimed subject matter may be practiced according to the claims without some or all of these specific details. It is to be understood that other embodiments can be used and structural changes can be made without departing from the scope of the claimed subject matter. For the purpose of clarity, technical material that is known in the technical fields related to the claimed subject matter has not been described in detail so that the claimed subject matter is not unnecessarily obscured.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

All publications, including patent documents, scientific articles and databases, referred to in this application and the bibliography and attachments are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The practice of the provided embodiments will employ, unless otherwise indicated, conventional techniques and descriptions of organic chemistry, polymer technology, molecular biology (including recombinant techniques), cell biology, biochemistry, and sequencing technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds., *Genome Analysis: A Laboratory Manual Series* (Vols. I-IV) (1999); Weiner, Gabriel, Stephens, Eds., *Genetic Variation: A Laboratory Manual* (2007); Dieffenbach, Dveksler, Eds., *PCR Primer: A Laboratory Manual* (2003); Bowtell and Sambrook, *DNA Microarrays: A Molecular Cloning Manual* (2003); Mount, *Bioinformatics: Sequence and Genome Anazvsis* (2004); Sambrook and Russell, *Condensed Protocols from Molecular Cloning: A Laboratory Manual* (2006); and Sambrook and Russell, *Molecular Cloning: A Laboratory Manual* (2002) (all from Cold Spring Harbor Laboratory Press); Ausubel et al. eds., *Current Protocols in Molecular Biology* (1987); T. Brown ed., *Essential Molecular Biology* (1991), IRL Press; Goeddel ed., *Gene Expression Technology* (1991), Academic Press; A. Bothwell et al. eds., *Methods for Cloning and Analysis of Eukaryotic Genes* (1990), Bartlett Publ.; M. Kriegler, *Gene Transfer and Expression* (1990), Stockton Press; R. Wu et al. eds., *Recombinant DNA Methodology* (1989), Academic Press; M. McPherson et al., *PCR: A Practical Approach* (1991), IRL Press at Oxford University Press; Stryer, *Biochemistry* (4th Ed.) (1995), W. H. Freeman, New York N.Y.; Gait, *Oligonucleotide Synthesis: A Practical Approach* (2002), IRL Press, London; Nelson and Cox, Lehninger, *Principles of Biochemistry* (2000) 3rd Ed., W. H. Freeman Pub., New York, N.Y.; Berg, et al., *Biochemistry* (2002) 5th Ed., W. H. Freeman Pub., New York, N.Y.; D. Weir & C. Blackwell, eds., *Handbook of*

*Experimental Immunology* (1996), Wiley-Blackwell; A. Abbas et al., *Cellular and Molecular Immunology* (1991, 1994), W.B. Saunders Co.; and J. Coligan et al. eds., *Current Protocols in Immunology* (1991), all of which are herein incorporated in their entirety by reference for all purposes.

As used herein and in the appended claims, the singular forms "a," "an," and "the" include plural referents unless the context clearly dictates otherwise. For example, "a" or "an" means "at least one" or "one or more." Thus, reference to "a biological target" refers to one or more biological targets, and reference to "the method" includes reference to equivalent steps and methods disclosed herein and/or known to those skilled in the art, and so forth.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

As used herein, an "individual" can be any living organism, including humans and other mammals. A "subject" as used herein can be an organism to which the provided compositions, methods, kits, devices, and systems can be administered or applied. In one embodiment, the subject can be a mammal or a cell, a tissue, an organ or a part of the mammal. Mammals include, but are not limited to, humans, and non-human animals, including farm animals, sport animals, rodents and pets.

As used herein, a "biological sample" can refer to any sample obtained from a living or viral source or other source of macromolecules and biomolecules, and includes any cell type or tissue of a subject from which nucleic acid or protein or other macromolecule can be obtained. The biological sample can be a sample obtained directly from a biological source or a sample that is processed. For example, isolated nucleic acids that are amplified constitute a biological sample. Biological samples include, but are not limited to, body fluids, such as blood, plasma, serum, cerebrospinal fluid, synovial fluid, urine and sweat, tissue and organ samples from animals and plants and processed samples derived therefrom.

As used herein, a "composition" can be any mixture of two or more products or compounds. It may be a solution, a suspension, liquid, powder, a paste, aqueous, non-aqueous or any combination thereof.

The terms "polynucleotide," "oligonucleotide," "nucleic acid" and "nucleic acid molecule" are used interchangeably herein to refer to a polymeric form of nucleotides of any length, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, and mRNA, whether spliced or unspliced, any other type of polynucleotide which is an N- or C-glycoside of a purine or pyrimidine base, and other polymers containing normucleotidic backbones, for example, polyamide (e.g., peptide nucleic acids ("PNAs")) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. Thus, these terms include, for example, 3'-deoxy-2', 5'-DNA, oligodeoxyribonucleotide N3' to P5' phosphoramidates, 2'-O-alkyl-substituted RNA, hybrids between DNA and RNA or between PNAs and DNA or RNA, and also include known types of modifications, for example, labels, alkylation, "caps," substitution of one or more of the nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. A nucleic acid generally will contain phosphodiester bonds, although in some cases nucleic acid analogs may be included that have alternative backbones such as phosphoramidite, phosphorodithioate, or methylphophoroamidite linkages; or peptide nucleic acid backbones and linkages. Other analog nucleic acids include those with bicyclic structures including locked nucleic acids, positive backbones, non-ionic backbones and non-ribose backbones. Modifications of the ribose-phosphate backbone may be done to increase the stability of the molecules; for example, PNA:DNA hybrids can exhibit higher stability in some environments. The terms "polynucleotide," "oligonucleotide," "nucleic acid" and "nucleic acid molecule" can comprise any suitable length, such as at least 5, 6, 7, 8, 9, 10, 20, 30, 40, 50, 100, 200, 300, 400, 500, 1,000 or more nucleotides.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., wherein one or more of the hydroxyl groups are replaced with halogen, aliphatic groups, or are functionalized as ethers, amines, or the like. The term "nucleotidic unit" is intended to encompass nucleosides and nucleotides.

"Nucleic acid probe" refers to a structure comprising a polynucleotide, as defined above, that contains a nucleic acid sequence that can bind to a corresponding target. The polynucleotide regions of probes may be composed of DNA, and/or RNA, and/or synthetic nucleotide analogs.

The terms "polypeptide", "oligopeptide", "peptide" and "protein" are used interchangeably herein to refer to polymers of amino acids of any length, e.g., at least 5, 6, 7, 8, 9, 10, 20, 30, 40, 50, 100, 200, 300, 400, 500, 1,000 or more amino acids. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

The terms "binding agent" and "target-binding moiety" as used herein may refer to any agent or any moiety thereof that specifically binds to a biological molecule of interest.

The biological targets or molecules to be detected can be any biological molecules including but not limited to proteins, nucleic acids, lipids, carbohydrates, ions, or multicomponent complexes containing any of the above. Examples of subcellular targets include organelles, e.g., mitochondria, Golgi apparatus, endoplasmic reticulum, chloroplasts, endocytic vesicles, exocytic vesicles, vacuoles, lysosomes, etc. Exemplary nucleic acid targets can include genomic DNA of various conformations (e.g., A-DNA, B-DNA, Z-DNA), mitochondria DNA (mtDNA), mRNA, tRNA, rRNA, hRNA, miRNA, and piRNA.

As used herein, "biological activity" may include the in vivo activities of a compound or physiological responses that result upon in vivo administration of a compound, composition or other mixture. Biological activity, thus, may encompass therapeutic effects and pharmaceutical activity of such compounds, compositions and mixtures. Biological activities may be observed in vitro systems designed to test or use such activities.

The term "binding" can refer to an attractive interaction between two molecules which results in a stable association in which the molecules are in close proximity to each other. Molecular binding can be classified into the following types: non-covalent, reversible covalent and irreversible covalent. Molecules that can participate in molecular binding include proteins, nucleic acids, carbohydrates, lipids, and small organic molecules such as pharmaceutical compounds. Proteins that form stable complexes with other molecules are often referred to as receptors while their binding partners are called ligands. Nucleic acids can also form stable complex with themselves or others, for example, DNA-protein complex, DNA-DNA complex, DNA-RNA complex.

As used herein, the term "specific binding" refers to the specificity of a binder, e.g., an antibody, such that it preferentially binds to a target, such as a polypeptide antigen. When referring to a binding partner (e.g., protein, nucleic acid, antibody or other affinity capture agent, etc.), "specific binding" can include a binding reaction of two or more binding partners with high affinity and/or complementarity to ensure selective hybridization under designated assay conditions. Typically, specific binding will be at least three times the standard deviation of the background signal. Thus, under designated conditions the binding partner binds to its particular target molecule and does not bind in a significant amount to other molecules present in the sample. Recognition by a binder or an antibody of a particular target in the presence of other potential interfering substances is one characteristic of such binding. Preferably, binders, antibodies or antibody fragments that are specific for or bind specifically to a target bind to the target with higher affinity than binding to other non-target substances. Also preferably, binders, antibodies or antibody fragments that are specific for or bind specifically to a target avoid binding to a significant percentage of non-target substances, e.g., non-target substances present in a testing sample. In some embodiments, binders, antibodies or antibody fragments of the present disclosure avoid binding greater than about 90% of non-target substances, although higher percentages are clearly contemplated and preferred. For example, binders, antibodies or antibody fragments of the present disclosure avoid binding about 91%, about 92%, about 93%, about 94%, about 95%, about 96%, about 97%, about 98%, about 99%, and about 99% or more of non-target substances. In other embodiments, binders, antibodies or antibody fragments of the present disclosure avoid binding greater than about 10%, 20%, 30%, 40%, 50%, 60%, or 70%, or greater than about 75%, or greater than about 80%, or greater than about 85% of non-target substances.

The term "antibody" as used herein may include an entire immunoglobulin or antibody or any functional fragment of an immunoglobulin molecule which is capable of specific binding to an antigen, such as a carbohydrate, polynucleotide, lipid, polypeptide, or a small molecule, etc., through at least one antigen recognition site, located in the variable region of the immunoglobulin molecule, and can be an immunoglobulin of any class, e.g., IgG, IgM, IgA, IgD and IgE. IgY, which is the major antibody type in avian species such as chicken, is also included. An antibody may include the entire antibody as well as any antibody fragments capable of binding the antigen or antigenic fragment of interest. Examples include complete antibody molecules, antibody fragments, such as Fab, F(ab')2, CDRs, VL, VH, and any other portion of an antibody which is capable of specifically binding to an antigen. Antibodies used herein are immunoreactive or immunospecific for, and therefore specifically and selectively bind to, for example, proteins either detected (i.e., biological targets) or used for detection (i.e., probes) in the assays of the invention. An antibody as used herein can be specific for any of the biological targets disclosed herein or any combinations thereof. In certain embodiments, a biological target itself of the present disclosure can be an antibody or fragments thereof.

As used herein, a "fragment thereof" "region thereof" and "portion thereof" can refer to fragments, regions and portions that substantially retain at least one function of the full length polypeptide.

As used herein, the term "antigen" may refer to a target molecule that is specifically bound by an antibody through its antigen recognition site. The antigen may be monovalent or polyvalent, i.e., it may have one or more epitopes recognized by one or more antibodies. Examples of kinds of antigens that can be recognized by antibodies include polypeptides, oligosaccharides, glycoproteins, polynucleotides, lipids, or small molecules, etc.

As used herein, the term "epitope" can refer to a peptide sequence of at least about 3 to 5, preferably about 5 to 10 or 15, and not more than about 1,000 amino acids (or any integer there between), which define a sequence that by itself or as part of a larger sequence, binds to an antibody generated in response to such sequence. There is no critical upper limit to the length of the fragment, which may, for example, comprise nearly the full-length of the antigen sequence, or even a fusion protein comprising two or more epitopes from the target antigen. An epitope for use in the subject invention is not limited to a peptide having the exact sequence of the portion of the parent protein from which it is derived, but also encompasses sequences identical to the native sequence, as well as modifications to the native sequence, such as deletions, additions and substitutions (conservative in nature).

The terms "complementary" and "substantially complementary" may include the hybridization or base pairing or the formation of a duplex between nucleotides or nucleic acids, for instance, between the two strands of a double-stranded DNA molecule or between an oligonucleotide primer and a primer binding site on a single-stranded nucleic acid. Complementary nucleotides are, generally, A and T (or A and U), or C and G. Two single-stranded RNA or DNA molecules are said to be substantially complementary when the nucleotides of one strand, optimally aligned and compared and with appropriate nucleotide insertions or deletions, pair with at least about 80% of the other strand, usually at least about 90% to about 95%, and even about 98% to about 100%. In one aspect, two complementary sequences of nucleotides are capable of hybridizing, preferably with less than 25%, more preferably with less than 15%, even more preferably with less than 5%, most preferably with no mismatches between opposed nucleotides. Preferably the two molecules will hybridize under conditions of high stringency.

"Hybridization" as used herein may refer to the process in which two single-stranded polynucleotides bind non-covalently to form a stable double-stranded polynucleotide. In one aspect, the resulting double-stranded polynucleotide can be a "hybrid" or "duplex." "Hybridization conditions" typically include salt concentrations of approximately less than 1 M, often less than about 500 mM and may be less than about 200 mM. A "hybridization buffer" includes a buffered salt solution such as 5% SSPE, or other such buffers known in the art. Hybridization temperatures can be as low as 5° C., but are typically greater than 22° C., and more typically greater than about 30° C., and typically in excess of 37° C. Hybridizations are often performed under stringent conditions, i.e., conditions under which a sequence will hybridize to its target sequence but will not hybridize to other, non-complementary sequences. Stringent conditions are sequence-dependent and are different in different circumstances. For example, longer fragments may require higher hybridization temperatures for specific hybridization than short fragments. As other factors may affect the stringency of hybridization, including base composition and length of the complementary strands, presence of organic solvents, and the extent of base mismatching, the combination of parameters is more important than the absolute measure of any one parameter alone. Generally stringent conditions are selected to be about 5° C. lower than the $T_m$ for the specific sequence at a defined ionic strength and pH. The melting temperature $T_m$ can be the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation, $T_m=81.5+0.41$ (% G+C), when a nucleic acid is in aqueous solution at 1 M NaCl (see e.g., Anderson and Young, Quantitative Filter Hybridization, in *Nucleic Acid Hybridization* (1985)). Other references (e.g., Allawi and SantaLucia, Jr., Biochemistry, 36:10581-94 (1997)) include alternative methods of computation which take structural and environmental, as well as sequence characteristics into account for the calculation of $T_m$.

In general, the stability of a hybrid is a function of the ion concentration and temperature. Typically, a hybridization reaction is performed under conditions of lower stringency, followed by washes of varying, but higher, stringency. Exemplary stringent conditions include a salt concentration of at least 0.01 M to no more than 1 M sodium ion concentration (or other salt) at a pH of about 7.0 to about 8.3 and a temperature of at least 25° C. For example, conditions of 5×SSPE (750 mM NaCl, 50 mM sodium phosphate, 5 mM EDTA at pH 7.4) and a temperature of approximately 30° C. are suitable for allele-specific hybridizations, though a suitable temperature depends on the length and/or GC content of the region hybridized. In one aspect, "stringency of hybridization" in determining percentage mismatch can be as follows: 1) high stringency: 0.1×SSPE, 0.1% SDS, 65° C.; 2) medium stringency: 0.2×SSPE, 0.1% SDS, 50° C. (also referred to as moderate stringency); and 3) low stringency: 1.0×SSPE, 0.1% SDS, 50° C. It is understood that equivalent stringencies may be achieved using alternative buffers, salts and temperatures. For example, moderately stringent hybridization can refer to conditions that permit a nucleic acid molecule such as a probe to bind a complementary nucleic acid molecule. The hybridized nucleic acid molecules generally have at least 60% identity, including for example at least any of 70%, 75%, 80%, 85%, 90%, or 95% identity. Moderately stringent conditions can be conditions equivalent to hybridization in 50% formamide, 5×Denhardt's solution, 5×SSPE, 0.2% SDS at 42° C., followed by washing in 0.2×SSPE, 0.2% SDS, at 42° C. High stringency conditions can be provided, for example, by hybridization in 50% formamide, 5×Denhardt's solution, 5×SSPE, 0.2% SDS at 42° C., followed by washing in 0.1×SSPE, and 0.1% SDS at 65° C. Low stringency hybridization can refer to conditions equivalent to hybridization in 10% formamide, 5×Denhardt's solution, 6×SSPE, 0.2% SDS at 22° C., followed by washing in 1×SSPE, 0.2% SDS, at 37° C. Denhardt's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M EDTA. Other suitable moderate stringency and high stringency hybridization buffers and conditions are well known to those of skill in the art and are described, for example, in Sambrook et al., Molecular Cloning: A Laboratory Manual, 2nd ed., Cold Spring Harbor Press, Plainview, N.Y. (1989); and Ausubel et al., Short Protocols in Molecular Biology, 4th ed., John Wiley & Sons (1999).

Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See M. Kanehisa, Nucleic Acids Res. 12:203 (1984).

A "primer" used herein can be an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Primers usually are extended by a DNA polymerase.

"Ligation" may refer to the formation of a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon terminal nucleotide of one oligonucleotide with a 3' carbon of another nucleotide.

"Sequencing," "sequence determination" and the like means determination of information relating to the nucleotide base sequence of a nucleic acid. Such information may include the identification or determination of partial as well as full sequence information of the nucleic acid. Sequence information may be determined with varying degrees of statistical reliability or confidence. In one aspect, the term includes the determination of the identity and ordering of a plurality of contiguous nucleotides in a nucleic acid. "High throughput digital sequencing" or "next generation sequencing" means sequence determination using methods that determine many (typically thousands to billions) of nucleic acid sequences in an intrinsically parallel manner, i.e. where DNA templates are prepared for sequencing not one at a time, but in a bulk process, and where many sequences are read out preferably in parallel, or alternatively using an ultra-high throughput serial process that itself may be parallelized. Such methods include but are not limited to pyrosequencing (for example, as commercialized by 454 Life Sciences, Inc., Branford, Conn.); sequencing by ligation (for example, as commercialized in the SOLiD™ technology, Life Technologies, Inc., Carlsbad, Calif.); sequencing by synthesis using modified nucleotides (such as commercialized in TruSeq™ and HiSeg™ technology by Illumina, Inc., San Diego, Calif.; HeliScope™ by Helicos Biosciences Corporation, Cambridge, Ma.; and PacBio RS by Pacific Biosciences of California, Inc., Menlo Park, Calif.), sequencing by ion detection technologies (such as Ion Torrent™ technology, Life Technologies, Carlsbad, Calif.); sequencing of DNA nanoballs (Complete Genomics, Inc., Mountain View, Calif.); nanopore-based sequencing technologies (for example, as developed by Oxford Nanopore Technologies, LTD, Oxford, UK), and like highly parallelized sequencing methods.

"SNP" or "single nucleotide polymorphism" may include a genetic variation between individuals; e.g., a single nitrogenous base position in the DNA of organisms that is variable. SNPs are found across the genome; much of the genetic variation between individuals is due to variation at SNP loci, and often this genetic variation results in phenotypic variation between individuals. SNPs for use in the present invention and their respective alleles may be derived from any number of sources, such as public databases (U.C. Santa Cruz Human Genome Browser Gateway (genome.ucsc.edu/cgi-bin/hgGateway) or the NCBI dbSNP website (www.ncbi.nlm.nih gov/SNP/), or may be experimentally determined as described in U.S. Pat. No. 6,969,589; and US Pub. No. 2006/0188875 entitled "Human Genomic Polymorphisms." Although the use of SNPs is described in some of the embodiments presented herein, it will be understood that other biallelic or multi-allelic genetic markers may also be used. A biallelic genetic marker is one that has two polymorphic forms, or alleles. As mentioned above, for a biallelic genetic marker that is associated with a trait, the allele that is more abundant in the genetic composition of a case group as compared to a control group is termed the "associated allele," and the other allele may be referred to as the "unassociated allele." Thus, for each biallelic polymorphism that is associated with a given trait (e.g., a disease or drug response), there is a corresponding associated allele. Other biallelic polymorphisms that may be used with the methods presented herein include, but are not limited to multinucleotide changes, insertions, deletions, and translocations. It will be further appreciated that references to DNA herein may include genomic DNA, mitochondrial DNA, episomal DNA, and/or derivatives of DNA such as amplicons, RNA transcripts, cDNA, DNA analogs, etc. The polymorphic loci that are screened in an association study may be in a diploid or a haploid state and, ideally, would be from sites across the genome.

As used herein, the term "microfluidic device" may generally refer to a device through which materials, particularly fluid borne materials, such as liquids, can be transported, in some embodiments on a micro-scale, and in some embodiments on a nanoscale. Thus, the microfluidic devices described by the presently disclosed subject matter can comprise microscale features, nanoscale features, and combinations thereof.

Accordingly, an exemplary microfluidic device typically comprises structural or functional features dimensioned on the order of a millimeter-scale or less, which are capable of manipulating a fluid at a flow rate on the order of a μL/min or less. Typically, such features include, but are not limited to channels, fluid reservoirs, reaction chambers, mixing chambers, and separation regions. In some examples, the channels include at least one cross-sectional dimension that is in a range of from about 0.1 μm to about 500 μm. The use of dimensions on this order allows the incorporation of a greater number of channels in a smaller area, and utilizes smaller volumes of fluids.

A microfluidic device can exist alone or can be a part of a microfluidic system which, for example and without limitation, can include: pumps for introducing fluids, e.g., samples, reagents, buffers and the like, into the system and/or through the system; detection equipment or systems; data storage systems; and control systems for controlling fluid transport and/or direction within the device, monitoring and controlling environmental conditions to which fluids in the device are subjected, e.g., temperature, current, and the like.

As used herein, the terms "channel," "micro-channel," "fluidic channel," and "microfluidic channel" are used interchangeably and can mean a recess or cavity formed in a material by imparting a pattern from a patterned substrate into a material or by any suitable material removing technique, or can mean a recess or cavity in combination with any suitable fluid-conducting structure mounted in the recess or cavity, such as a tube, capillary, or the like. In the present invention, channel size means the cross-sectional area of the microfluidic channel.

As used herein, the terms "flow channel" and "control channel" are used interchangeably and can mean a channel in a microfluidic device in which a material, such as a fluid, e.g., a gas or a liquid, can flow through. More particularly, the term "flow channel" refers to a channel in which a material of interest, e.g., a solvent or a chemical reagent, can flow through. Further, the term "control channel" refers to a flow channel in which a material, such as a fluid, e.g., a gas or a liquid, can flow through in such a way to actuate a valve or pump.

As used herein, "chip" may refer to a solid substrate with a plurality of one-, two- or three-dimensional micro structures or micro-scale structures on which certain processes, such as physical, chemical, biological, biophysical or biochemical processes, etc., can be carried out. The micro structures or micro-scale structures such as, channels and wells, electrode elements, electromagnetic elements, are incorporated into, fabricated on or otherwise attached to the substrate for facilitating physical, biophysical, biological, biochemical, chemical reactions or processes on the chip. The chip may be thin in one dimension and may have various shapes in other dimensions, for example, a rectangle, a circle, an ellipse, or other irregular shapes. The size of the major surface of chips of the present invention can vary considerably, e.g., from about 1 mm$^2$ to about 0.25 m$^2$. Preferably, the size of the chips is from about 4 mm$^2$ to about 25 cm$^2$ with a characteristic dimension from about 1 mm to about 5 cm. The chip surfaces may be flat, or not flat. The chips with non-flat surfaces may include channels or wells fabricated on the surfaces.

A microfluidic chip can be used for the methods and assay systems disclosed herein. A microfluidic chip can be made from any suitable materials, such as PDMS (Polydimethylsiloxane), glass, PMMA (polymethylmethacrylate), PET (polyethylene terephthalate), PC (Polycarbonate), etc., or a combination thereof.

"Multiplexing" or "multiplex assay" herein may refer to an assay or other analytical method in which the presence and/or amount of multiple targets, e.g., multiple nucleic acid target sequences, can be assayed simultaneously by using more than one capture probe conjugate, each of which has at least one different detection characteristic, e.g., fluorescence characteristic (for example excitation wavelength, emission wavelength, emission intensity, FWHM (full width at half maximum peak height), or fluorescence lifetime) or a unique nucleic acid or protein sequence characteristic.

Assays for Determining Spatial Patterns of Biological Targets

Disclosed herein are spatially-encoded, multiplexed methods and assay systems capable of high levels of multiplexing with an efficient spatial encoding scheme. In one embodiment, provided herein is instrumentation capable of delivering reagents to a sample and thereby spatially encoding multiple sites to which the reagents are delivered. In one aspect, reagents can be delivered to a sample according to a known spatial pattern, for example, a spatial pattern determined by histological features of the sample. In another aspect, reagents are delivered by random-access methods, such as inkjet and pin-spotting. In another aspect, microfluidic devices with addressing channels and the like are used to deliver reagents to a sample, and to spatially encode multiple sites in the sample to which the reagents are delivered. In some embodiments, the spatially-encoded ("addressed," or "address tagged"), multiplexed methods and assay systems comprise a decoding feature determined by a readout that is digital in nature. In one aspect, the methods and assay systems disclosed herein detect the presence or absence of a biological target or a biological activity indicative of a biological target. In another aspect, provided herein are methods and assay systems that can detect the amount or abundance of a biological target or biological activity indicative of a biological target at multiple sites in a sample, as well as the location of each of the multiple sites in the sample. Based on the analysis of the amount or abundance and the location information of one or more biological targets or activities, spatial patterns across the multiple sites in the sample can be generated. In any of the preceding embodiments, the method or assay system may not depend on an imaging technique for determining spatial or location information of the one or more biological targets in the sample, although the method or assay system may optionally comprise using an imaging technique for other purposes. Imaging techniques may include but are not limited to conventional immunohistochemical (IHC) imaging and immunofluorescence (IF) imaging. Methods and assays systems to determine a spatial pattern of abundance and/or activity of a biological target in a sample are disclosed in detail in U.S. application Ser. No. 13/080,616, entitled "Spatially encoded biological assays" (Pub. No.: US 2011/0245111), the disclosure of which is incorporated herein by reference for all purposes.

The present disclosure further provides instrumentation with an ability to deliver reagents to multiple sites in a sample, wherein each of the multiple sites can be identified by the reagents delivered thereto. In one embodiment, reagents are delivered in a spatially-defined pattern. The instrumentation, together with software, reagents and protocols, provides a key component of the methods and assay systems of the present disclosure, allowing for measurement of numerous biological targets or activities, including DNA, RNA and/or protein expression, and spatial localization of such biological targets or activities in a sample. In one embodiment, the abundance, expression, and/or activity and the location of biological targets in the biological samples are determined after the assay products of the multiplexed assay are removed from the biological sample and pooled for analysis. Determination of the abundance, expression, and/or activity and the location of biological targets can be performed by, e.g., next-generation sequencing, which easily provides millions to trillions of data points at low cost. The assay results such as the amount or activity of biological targets can then be mapped back to a specific location in the biological sample. The methods and assay systems provide tools to analyze the complex spatial patterns of cellular function and regulation in biological samples.

In one aspect, a method of determining a spatial pattern of abundance, expression, and/or activity of one or more biological targets across multiple sites in a sample is provided in FIG. 1. At Step 110, a probe for each of one or more biological targets is delivered to multiple sites in a sample, each probe comprising a target-binding moiety, an address tag that identifies each site to which the probe is delivered, and an identity tag.

In any of the embodiments of the present disclosure, the sample can be any biological sample or samples that can be affixed to a support or provided essentially in a two-dimensional manner, such that an assayed biological target or activity can be tied back to the location within the biological sample. In certain embodiments, the sample can be a freshly isolated sample, a fixed sample, a frozen sample, an embedded sample, a processed sample, or a combination thereof. Exemplary samples of the present disclosure include tissue sections (e.g., including whole animal sectioning and tissue biopsies), cell populations, or other biological structure disposed upon a support, such as on a slide (e.g., a microscope slide) or culture dish, and the like. In preferred embodiments, the methods and assay systems of the present disclosure are compatible with numerous biological sample types, including fresh samples, such as primary tissue sections, and preserved samples including but not limited to frozen samples and formalin-fixed, paraffin-embedded (FFPE) samples. In certain embodiments, the sample can be fixed with a suitable concentration of formaldehyde or paraformaldehyde, for example, 4% of formaldehyde or paraformaldehyde in phosphate buffered saline (PBS). In certain embodiments, the biological samples are immobilized on a substrate surface having discrete, independently measurable areas.

In one embodiment, the biological sample may contain one or more biological targets of interest. In any of the embodiment of the present disclosure, the one or more biological targets can be any biological molecules including but not limited to proteins, nucleic acids, lipids, carbohydrates, ions, or multicomponent complexes containing any of the above. Examples of subcellular targets include organelles, e.g., mitochondria, Golgi apparatus, endoplasmic reticulum, chloroplasts, endocytic vesicles, exocytic vesicles, vacuoles, lysosomes, etc. In some embodiments, the one or more biological targets can be nucleic acids, including RNA transcripts, genomic DNA sequences, cDNAs, amplicons, or other nucleic acid sequences. In other embodiments, the one or more biological targets can be proteins, enzymes (protein enzymes or ribozymes) and the like.

At Step 110, the probe for each of the multiple biological targets comprise: (1) a target-binding moiety capable of binding to the probe's corresponding biological target; (2) an address tag that identifies each site to which the probe is delivered; and (3) an identity tag that identifies the probe's corresponding biological target or target-binding moiety. Depending on the nature of the biological target, the target-binding moiety can be a target-specific nucleotide sequence (for example, a sequence complementary to a sequence of a nucleic acid target), small molecule, aptamer, antibody, lipid, carbohydrate, ion, affinity capture agent, or multicomponent complexes containing any of the above. The address tag identifies the position in the sample to which the probe is delivered, and the identity tag identifies the probe's corresponding biological target being assayed or the target-binding moiety. Thus, the identities of the address tag and the identity tag can be used to link assay results to biological targets and locations in the sample. In preferred embodiments, there can be at least two address tags for a biological target at each of multiple sites in a sample, each address tag identifying a parameter of each of the multiple sites. For example, there can be an X-axis address tag and a Y-axis address tag for each site in a sample placed on an X-Y coordinate plane. Thus, each site can be uniquely identified by its corresponding (X, Y) coordinates. In preferred embodiments of the present disclosure, the address tags and/or the identity tags can be oligonucleotides. In other embodiments, the address tags and/or the identity tags can be mass tags, fluorescent labels, or other moieties.

In some embodiments, the target-binding moiety, address tag, and/or identity tag of the probe are pre-coupled before being delivered to the biological sample. In the case where the probes are oligonucleotides, the target-binding sequence, address tag sequence, and/or identity tag sequence can be synthesized as a single oligonucleotide. Alternatively, the target-binding moiety, address tag, and/or identity tag of the probe can be synthesized or obtained separately and combined before delivery to the biological sample. For example, two separate oligonucleotides can be synthesized and coupled by, e.g., ligation; or an antibody and an oligonucleotide can be prepared separately and conjugated before delivery to the biological sample. In other embodiments, the probes and the address tags can be synthesized separately, and delivered to the biological sample at different steps (e.g., probes first and address tags thereafter, or vice versa) in the assay.

At Step 120, the probe is allowed to bind to its corresponding biological target in the sample and thereby to react or interact with the biological target. For example, conditions are provided to allow oligonucleotides to hybridize to nucleic acid targets, enzymes to catalyze reactions with protein targets, antibodies to bind epitopes within a target, etc. In the case where the biological targets are nucleic acids, the probes are typically oligonucleotides and hybridize to the target nucleic acids. In the case that the biological targets are proteins, the probes typically are aptamers, small molecules, or oligonucleotide-conjugated proteins that interact with target proteins by binding to them or by reacting with them (that is, one of the proteins is a substrate for the other). Oligonucleotides may be coupled to the probes or proteins by conjugation, chemical or photo-crosslinking via suitable groups and the like.

In some embodiments, after allowing the probes to bind to or interact with the one or more biological targets in the sample, probes bound to the biological targets may be separated from probes delivered to the sample but not bound to the biological targets. In one aspect, in the case where the biological targets are nucleic acids and the probes are oligonucleotides, the separation can be accomplished by, e.g., washing the unhybridized probes from the sample. Similarly, for other assays that are based on affinity binding, including those using aptamer, small molecule, and protein probes, washing steps can be used to remove low affinity binders. In the case where the probe is transformed via interaction with the target, e.g., in the case of a peptide, e.g., via cleavage by a protease or phosphorylation by a kinase, it is convenient to collect all probes, including both probes that have interacted with the biological targets and thus transformed and probes not transformed. After collection or pooling, an antibody or other affinity capture agent can be used to capture probes transformed by addition of a moiety (e.g., a phosphate group in cases of phosphorylation by a kinase). In cases where probes have been transformed via cleavage, the transformed probes can be separated, e.g., by capturing the non-transformed probes via a tag that is removed from the transformed probes during the transformation (e.g., by cleavage), or by adding a new tag at the site of cleavage.

In certain other embodiments, probes bound to the biological targets may not need to be separated from probes not bound to the biological targets for determining a spatial pattern of abundance, expression, and/or activity of the biological targets. At Step 130, probes bound to the one or more biological targets are analyzed. In certain embodiments, the analysis comprises determining abundance, expression, and/or activity of each biological target and the identities of the identity tag and the address tag for each biological target at each site. Numerous methods can be used to identify the address tags, identity tags and/or target-binding moieties of the probes of the methods and assay systems disclosed herein. The address tags can be detected using techniques such as mass spectroscopy (e.g., matrix-assisted laser desorption/ionization-time of flight mass spectrometry (MALDI-TOF), LC-MS/MS, and TOF/TOF™ LC/MS/MS), nuclear magnetic resonance imaging, or, preferably, nucleic acid sequencing. Examples of techniques for decoding the probes of the present invention can be found, for example, in US Pub. No. 20080220434, which is incorporated herein by reference. For example, the address tags may be oligonucleotide mass tags (OMTs or massTags). Such tags are described, e.g., in US Pub. No. 20090305237, which is incorporated by reference in its entirety. In yet another aspect, the probes can be amplified and hybridized to a microarray. This would require separate amplification reactions to be carried out, in which each amplification is specific to a particular address tag or subset of tags, accomplished by using tag-specific primers. Each amplification would also incorporate a different resolvable label (e.g. fluorophor). Following hybridization, the relative amounts of a particular target mapping to different spatial locations in the sample can be determined by the relative abundances of the resolvable labels. At Step 140, based on the analysis of probes bound to the one or more biological targets, a spatial pattern of abundance, expression, and/or activity of the one or more biological targets across the multiple sites in the sample is determined.

In a preferred aspect, the probes according to the present disclosure are substrates for high-throughput, next-generation sequencing, and highly parallel next-generation sequencing methods are used to confirm the sequence of the probes (including, for example, the sequence of the target-binding moiety, the address tag, and/or the identity tag). Suitable sequencing technologies include but are not limited to SOLiD™ technology (Life Technologies, Inc.) or Genome Ananlyzer (I lumina, Inc.). Such next-generation sequencing methods can be carried out, for example, using a one pass sequencing method or using paired-end sequencing. Next generation sequencing methods include, but are not limited to, hybridization-based methods, such as disclosed in e.g., Drmanac, U.S. Pat. Nos. 6,864,052; 6,309,824; and 6,401,267; and Drmanac et al., U.S. patent publication 2005/0191656; sequencing-by-synthesis methods, e.g., U.S. Pat. Nos. 6,210,891; 6,828,100; 6,969,488; 6,897,023; 6,833,246; 6,911,345; 6,787,308; 7,297,518; 7,462,449 and 7,501,245; US Publication Application Nos. 20110059436; 20040106110; 20030064398; and 20030022207; Ronaghi, et al., Science, 281:363-365 (1998); and Li, et al., Proc. Natl. Acad. Sci., 100:414-419 (2003); ligation-based methods, e.g., U.S. Pat. Nos. 5,912,148 and 6,130,073; and U.S. Pat. Appln Nos. 20100105052, 20070207482 and 20090018024; nanopore sequencing, e.g., U.S. Pat. Appln Nos. 20070036511; 20080032301; 20080128627; 20090082212; and Soni and Meller, Clin Chem 53:1996-2001 (2007), as well as other methods, e.g., U.S. Pat. Appln Nos. 20110033854; 20090264299; 20090155781; and 20090005252; also, see, McKernan, et al., Genome Res. 19:1527-41 (2009) and Bentley, et al., Nature 456:53-59 (2008), all of which are incorporated herein in their entirety for all purposes.

In preferred embodiments, probes bound to the one or more biological targets are analyzed by sequencing. Such analysis by sequencing comprises determining the amount of a sequencing product, which indicates abundance, expression, and/or activity of each biological target, the sequencing product comprising all or a portion of the address tag sequence and all or a portion of the identity tag sequence identifying each biological target at each site. In one embodiment, the address tag sequence of the sequencing product allows the mapping of the assay results back to the multiple sites in the sample.

In certain embodiments, two probes that bind to the same target molecule (for example, two polynucleotide probes that hybridize to adjacent sites on a nucleic acid target) may be assayed by extension followed by ligation (the extension-ligation assay). The extension-ligation assay allows certain target sequence to be determined de novo. For example, if the primer and the downstream oligo are separated by 20 bases and reverse transcriptase is used to fill this 20-base gap, 20 bases of sequence of the RNA target can be obtained. In certain embodiments, by using the extension-ligation assay in the present methods or assay systems, regions of sequence that are of particular interest may be characterized. For example, these regions may comprise mutations or variations, for example, with implications in cancer, MHC variations, and RNA editing.

In any of the embodiments disclosed herein, an extension assay may also be used and may allow certain target sequences, for example, nucleotide sequences, to be determined de novo. In one embodiment, an extension assay of the present disclosure may be performed as follows. A first primer may be used to make cDNA from a target sequence. In certain embodiments, the first primer can be a random primer (e.g., random hexamer) or a sequence-specific primer. A random primer can be used to make cDNA from the entire transcriptome, while a sequence-specific primer may be used to make cDNA from a specific target sequence. In certain aspects, the first primer may comprise a universal priming site for amplification of the assay products, an adaptor to enable sequence identification by sequencing techniques, and/or an adaptor for attaching address tags. In other embodiments, the first primer may be conjugated to an adaptor for attaching address tags. The X and Y address tags as described infra can be coupled to the first primer via the adaptor. Note that the X and Y address tags can be coupled to the same or different side relative to the target sequence, and the configuration may be used in any of embodiments disclosed herein. The Y address tag can be further linked to a universal priming site or an adaptor for sequencing coupled to biotin. The cDNA with conjugated X and Y address tags are then eluted and captured on a streptavidin bead, and a second primer can then be installed to the cDNA on the opposite side relative to the first primer. In some embodiments, capture of the polynucleotide sequence can be based on other hapten-binder combinations other than biotin-streptavidin, or be sequence-based. In certain embodiments, the second primer can be a random primer (e.g., random hexamer) or a sequence-specific primer. In certain aspects, the second primer may comprise a universal priming site for amplification of the assay products, an adaptor to enable sequence identification by sequencing techniques, and/or an adaptor for attaching address tags. In other embodiments, the second primer may be conjugated to a universal priming site or an adaptor for sequencing. Together with the priming site or adaptor coupled to biotin, the sequence can be extended from the second primer, amplified, and sequenced.

The methods and assay systems disclosed herein may comprise an amplification step, and in particular, a nucleic acid amplification step. In certain aspects, the amplification step is performed by PCR. In some embodiments, linear amplification (e.g., by T7 RNA polymerase) may be used instead of PCR or as a partial replacement for PCR. In one aspect, linear amplification of polynucleotides may cause less distortion of the relative abundances of different sequences. This can be accomplished by including a T7 RNA pol promoter in one of the universal portions of the sequence. In this case, the promoter itself and regions upstream of the promoter are not copied. In yet other embodiments, other amplification methods may be used in the methods and assay systems disclosed herein. For some sequencing methods (e.g., nanopore sequencing), amplification may be optional.

The T7 RNA polymerase based amplification is a commonly used protocol for mRNA amplification originally described by van Gelder et al., Proc. Natl. Acad. Sci. USA 87, 1663-1667 (1990). The protocol consists of the synthesis of a cDNA complementary to the mRNA ("first strand synthesis"), effected by reverse transcription, followed by second strand synthesis to yield double-stranded cDNA, and in vitro transcription using the double-stranded cDNA as template effected with T7 RNA polymerase. The last step provides single-stranded antisense RNA (aRNA), which may be labeled in case labeled nucleotides are provided. The nucleotides may be labeled by radioactive labeling or non-radioactive labeling methods. Eberwine et al. (Proc. Natl. Acad. Sci. USA 89, 3010-3014 (1992)) extended van Gelder's method by adding a second round of amplification using the RNA obtained in the first round as template. Wang et al. (Nature Biotechnol. 18, 457-459 (2000)) provided a variant of the original T7 method, characterized by a modified second strand synthesis method. The second strand synthesis method of Wang et al. is known in the art as the SMART™ technology (Clontech) for cDNA synthesis. Baugh et al. (Nucleic Acids Res. 29, E29 (2001)) describe an optimized variant of the method according to van Gelder et al. and analyze the performance on Affymetrix DNA chips (GeneChip®). Affymetrix GeneChips are designed to probe the anti-sense strand. Any other DNA chip or microarray probing the anti-sense strand may be envisaged when performing a T7 RNA amplification, wherein labeling occurs during the in vitro transcription step.

In other embodiments, amplification techniques such as rolling circle amplification (RCA) and circle to circle amplification (C2CA) may be used for probe, target, tag, and/or signal amplification of the present disclosure. RCA is a linear-isothermal process in the presence of certain DNA polymerases, using an ssDNA mini-circle as a template (Fire and Xu, Proc. Natl. Acad. Sci., 92: 4641-4645 (1995); Daubendiek et al., J. Am. Chem. Soc. 117:77818-7819 (1995)). In certain aspects, a polynucleotide sequence can be replicated about 500 to 1000 times, depending on the amplification time. For example, in a dual targeting assay for a target protein as discussed supra, a linear ligated product is formed (e.g., when two antibodies bind to adjacent domains on a target protein, the antibodies' oligonucleotide tags can be ligated), and can be cut by restriction enzymes and then re-ligated to form a DNA circle by a DNA ligase and a template. In certain embodiments, phi29 DNA polymerase can be used to extend the primer, which is also the template, to form a long ssDNA containing a number of sequences complementary to the initial DNA circle. C2CA is based on RCA, and may include three steps: replication, monomerization and ligation (Dahl et al., Proc. Natl. Acad. Sci., 101: 4548-4553 (2004)). The original circular DNA is considered as the positive polarity. After one step of replication (RCA reaction), the product is converted into the opposite polarity. Restriction oligos with the positive polarity (RO$^+$) can form duplex regions with the RCA product, and the duplex regions can be cleaved by restriction enzymes to generate monomers. Then the monomers can be guided into a ligation step and circularized. These circles serve as the templates for the next round of RCA, primed by the RO$^+$. The process can be further repeated to produce around 100-fold higher concentration of target sequences than conventional PCR.

Figure 2:
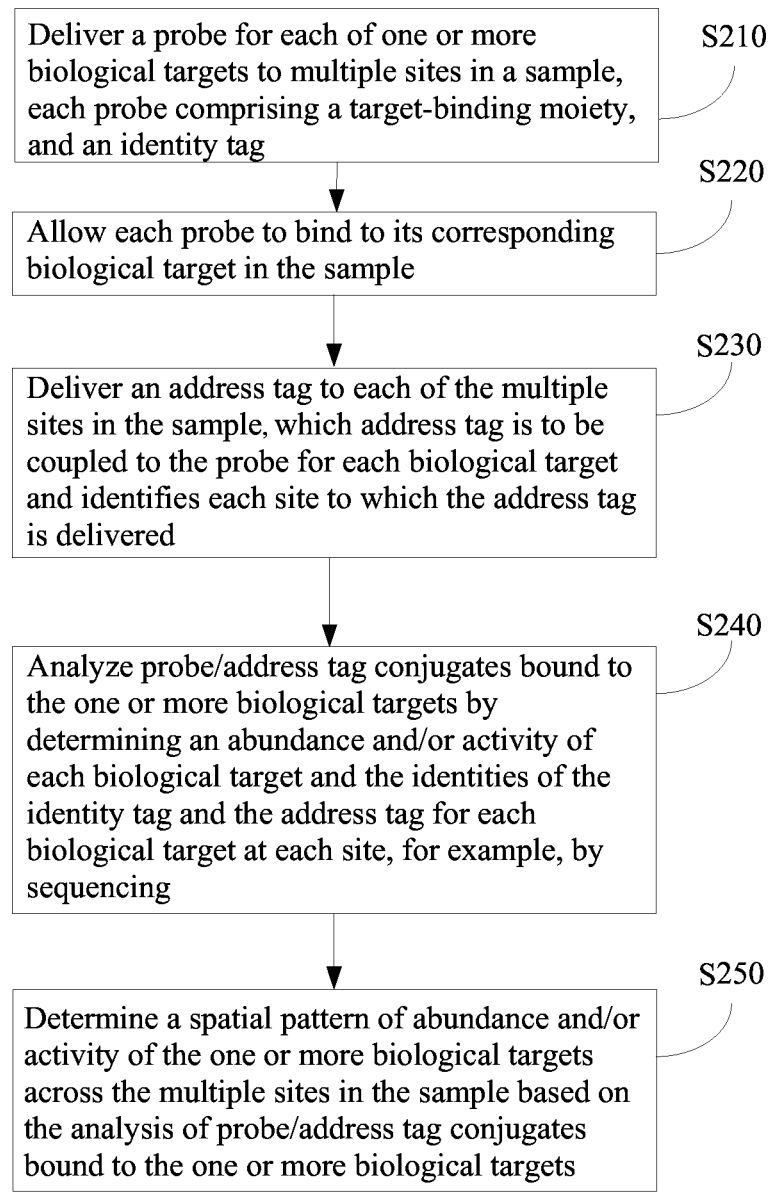
FIG. 2 is a flow chart illustrating exemplary steps of a method of determining a spatial pattern of abundance, expression, and/or activity of one or more biological targets across multiple sites in a sample, according to an embodiment of the present disclosure.

In another aspect, as shown in FIG. 2, a method of determining a spatial pattern of abundance, expression, and/or activity of one or more biological targets across multiple sites in a sample is provided, featuring an efficient implementation of an address tagging scheme for the one or more biological targets across the multiple sites. In one embodiment, the address tagging scheme is a combinatorial scheme using at least two address tags for the biological targets for each of the multiple sites in the sample. At Step 210, a probe for each of one or more biological targets to multiple sites in a sample is delivered, each probe comprising (1) a target-binding moiety capable of binding to the probe's corresponding biological target; and (2) an identity tag that identifies the probe's corresponding biological target or target-binding moiety. Depending on the nature of the biological target, the target-binding moiety can be a target-specific nucleotide sequence (for example, a sequence complementary to a sequence of a nucleic acid target), small molecule, aptamer, antibody, lipid, carbohydrate, ion, affinity capture agent, or multicomponent complexes containing any of the above. At Step 220, each probe is allowed to interact with or bind to its corresponding biological target in the sample, under appropriate conditions.

In certain embodiments, probes not bound to the biological targets may be removed, and thereby separated from probes bound to the biological targets. Such separation can be performed essentially as discussed above, for example, by washing the sample to remove unhybridized oligonucleotide probes. In certain other embodiments, probes bound to the biological targets may not need to be separated from probes not bound to the biological targets for determining a spatial pattern of abundance, expression, and/or activity of the biological targets.

Next, at Step 230, an address tag is delivered to each of the multiple sites in the sample, and the address tag is to be coupled to the probe for each biological target and identifies each site to which the address tag is delivered. Note that in this aspect, the probe and address tag are delivered in separate steps. In certain embodiments where the probes are oligonucleotides, the address tags may be coupled to the oligonucleotide probes by various means known to the skilled artisan, for example, by extension, ligation, ligation followed by extension, or any combination thereof. For instance, the information in the address tags can be transferred by using a DNA polymerase to extend a probe oligonucleotide that acts as a primer, and thereby copy and incorporate the sequence of the address tags.

At Step 240, probe/address tag conjugates bound to the one or more biological targets are analyzed. In certain embodiments, the analysis comprises determining abundance, expression, and/or activity of each biological target and the identities of the identity tag and the address tag for each biological target at each site. In one aspect, the abundance, expression, and/or activity of each biological target can be assessed by determining the amount of the probe or the probe/address tag conjugate bound to the target. Numerous methods can be used to identify the address tags, identity tags and/or target-binding moieties of the probes, as discussed above. In preferred embodiments, probes or probe/address tag conjugates bound to the one or more biological targets are analyzed by sequencing. Any suitable sequence techniques and methods as discussed above can be used, including high-throughput, next-generation sequencing, and highly parallel next-generation sequencing methods. Preferably, in any of embodiments of the present disclosure, all or a portion of the address tag sequence and all or a portion of the identity tag sequence are determined from the same sequencing product. Preferably, also determined at the same time is the abundance of the sequencing product, for example, the "copy number" or "hits" of the sequencing product. The abundance of the sequencing product may correlate with the amount of the probe or probe/address tag conjugate bound to the target, which in turn can correlate with the abundance, expression, and/or activity of each biological target. In some embodiments, the abundance of sequence products reveals the relative quantity of biological targets at the location.

Based on the analysis of probe/address tag conjugates bound to the one or more biological targets at Step 240, a spatial pattern of abundance, expression, and/or activity of the one or more biological targets across the multiple sites in the sample is determined at Step 250, for example, by mapping the assayed abundance, expression, and/or activity of each biological target back to each site of the sample.

Although individual steps are discussed in a particular order in certain embodiments to better explain the claimed subject matter, the precise order of the steps can be varied. For example, Steps 210 and 230 can be combined, so that a mixture of the probes and address tags is delivered. Coupling of the address tag to the probe may be carried out immediately after the combined steps 210 and 230, or concomitantly with them. It can therefore be appreciated that the address tagging of probe molecules and the separation of probes based on their ability to interact with their corresponding targets can be accomplished with flexibility. Similarly, there is considerable flexibility in the address tagging scheme. As described infra, the methods and assay systems disclosed herein are particularly amenable to combinatorial methods.

Spatially Encoded Genomic Assay

Figure 3:
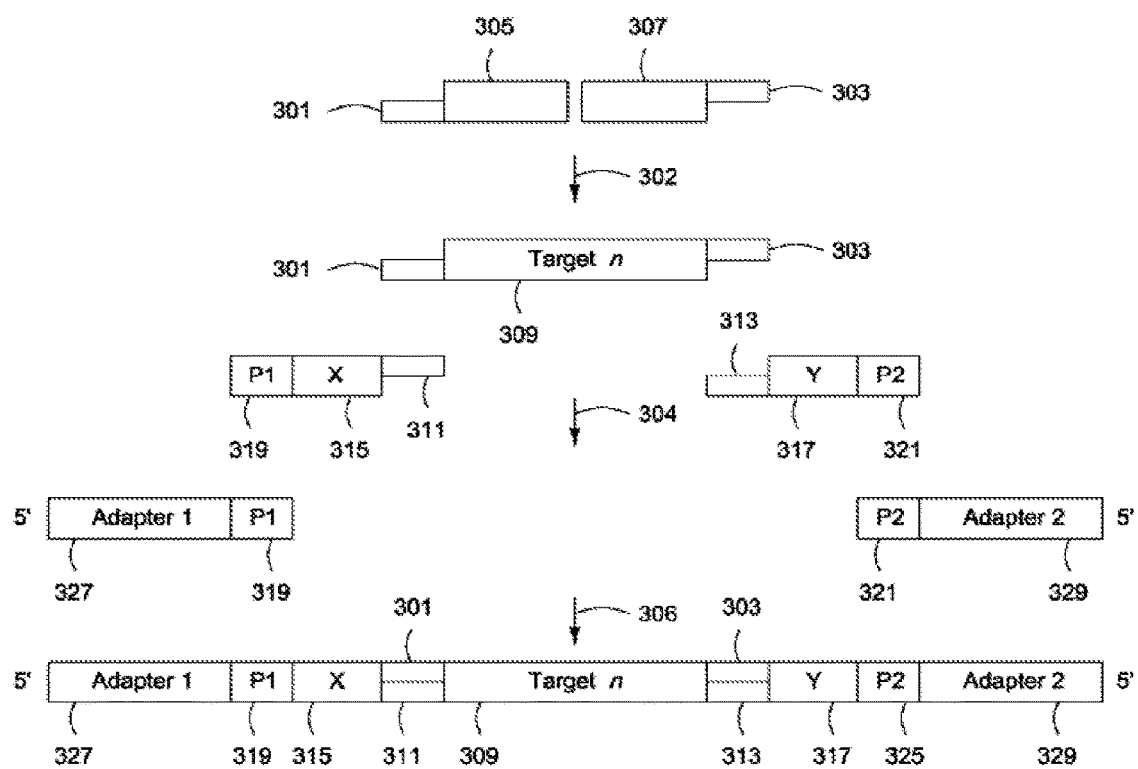
FIG. 3 illustrates a combinatorial addressing scheme, according to one embodiment of the present disclosure.

In particular embodiments, the methods and assay systems can be used for nucleic acid analysis, for example, for genomic analysis, genotyping, detecting single nucleotide polymorphisms (SNPs), quantitation of DNA copy number or RNA transcripts, localization of particular transcripts within samples, and the like. FIG. 3 illustrates an exemplary assay and address tagging scheme. For illustrative purposes, the target is a nucleic acid sequence, and two oligonucleotide probes are provided, and it should be understood that the disclosed methods and assay systems can be used for any suitable target employing one or more suitable probes. Each oligonucleotide probe comprises a target-specific region seen at 305 and 307, respectively. In certain embodiments, for example for detecting SNPs, the two target-specific regions are located on either side of the SNP to be analyzed. Each oligonucleotide probe also comprises a ligation region, seen at 301 and 303, respectively. The oligonucleotide probes are allowed to hybridize to a target nucleic acid (not shown) in the biological sample. At Step 302, one or both of the oligonucleotide probes may be extended and ligated to the other probe to form an extended probe comprising target nucleic acid region 309 and ligation regions 301 and 303. In some embodiments, the two probes are immediately adjacent to each other, and only ligation is needed to form an extended probe. In some embodiments, Step 302 may be used to incorporate an SNP sequence or other target sequences to be assayed.

Two address tags, both comprising an address tag region (seen at 315 and 317), a ligation region (seen at 311 and 313), and a primer region (seen at 319 and 321) are combined with and ligated to the extended probe at step 304 to form a target-specific oligonucleotide. In contrast with FIG. 1, the probes and address tags are delivered at separate steps. In some embodiments, a pair of address tags ligate specifically to one side of the target sequence or the other (i.e., 5' or 3' of the target sequence), respectively. In certain embodiments, the ligation and primer regions of the address tags and probes are universal; that is, the set of ligation and primer regions used in constructing the probes and address tags are constant, and only the target-specific regions of the probes and the address tag region of the address tag differ. In alternative embodiments, the ligation and primer regions are not universal and each probe and/or address tag may comprise a different ligation and/or primer region.

Following ligation, the probe/address tag conjugates are eluted, pooled, and, optionally, sequencing adaptors are added to the probe/address tag conjugates via PCR. In alternative embodiments, sequencing primers may be ligated to the address tags, or sequencing primer sequences can be included as part of the address tags. As seen in FIG. 3, each sequencing adaptor comprises primer region 319 or 321, compatible with the primer regions 319 and 321 on the address tags. The final construct comprising first adaptor 327, first primer region 319, first coding tag 315, ligation regions 311 and 301, target region 309, ligation regions 313 and 303, second coding tag 317, second primer region 325 and second adaptor 329 can be subject to sequencing, for example, by input into a digital high-throughput sequencing process.

A combination of extension and ligation reactions are exemplified in FIG. 3, but it should be appreciated that a variety of reactions may be used to couple the address tags to the target-specific probes, including ligation only (e.g., for oligonucleotides that hybridize to contiguous portions of the target nucleic acid sequence). Alternatively, an assay utilizing an additional oligonucleotide, such as in the GOLDEN-GATE® assay (Illumina, Inc., San Diego, Calif.) (see Fan, et al., Cold Spring Symp. Quant. Biol., 68:69-78 (2003)), may be employed.

To maximize the efficiency of address tagging, a combinatorial approach using pairs of address tags can be used. By de-coupling the target-specific information and the spatial information in the address tags, the number of oligonucleotides required for determining a spatial pattern of one or more biological targets across multiple sites in a sample is dramatically reduced, with a concomitant decrease in cost.

Figure 4:
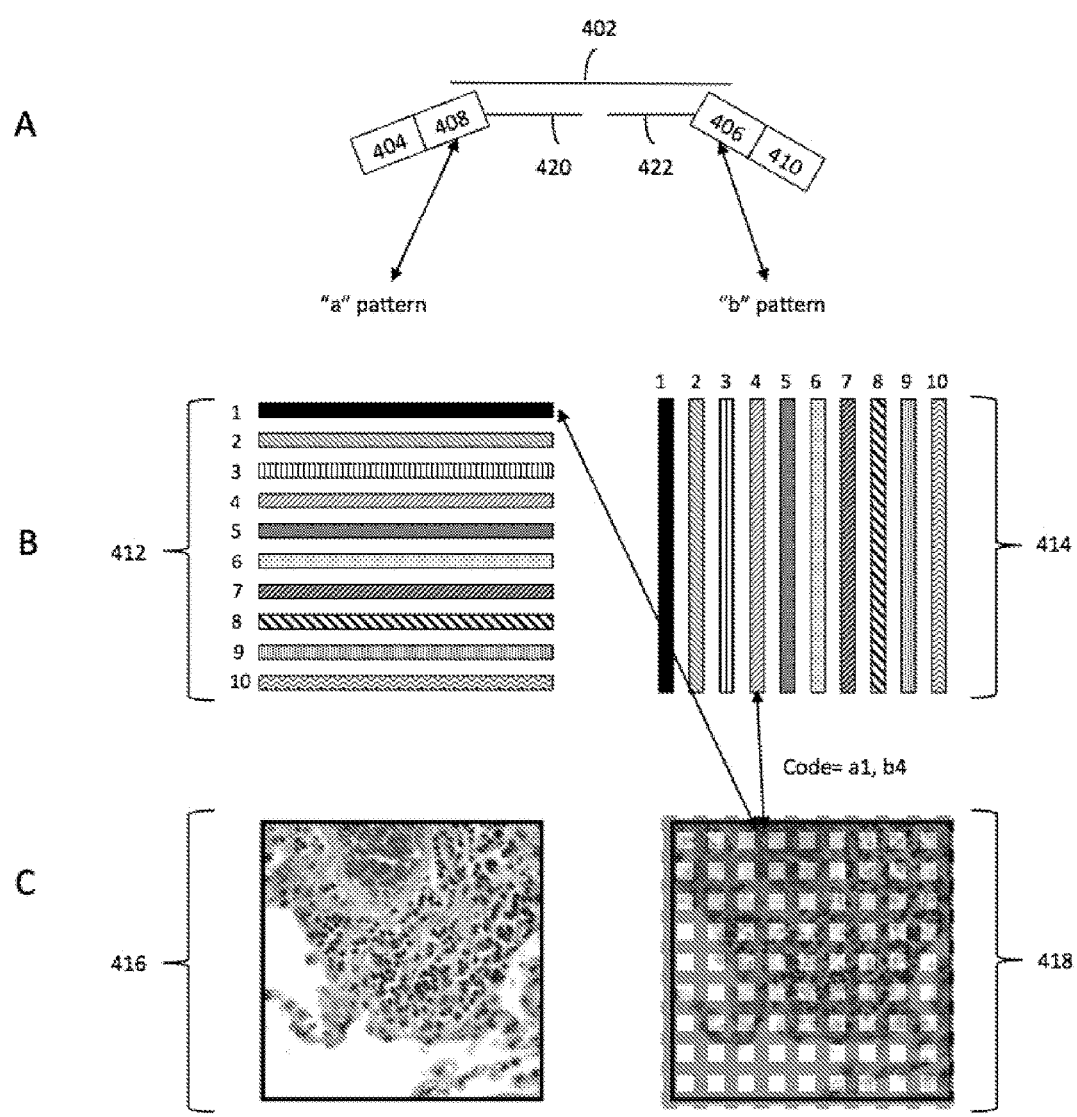
FIG. 4 illustrates combinatorial addressing schemes applied to a sample, according to embodiments of the present disclosure.
Figure 4:
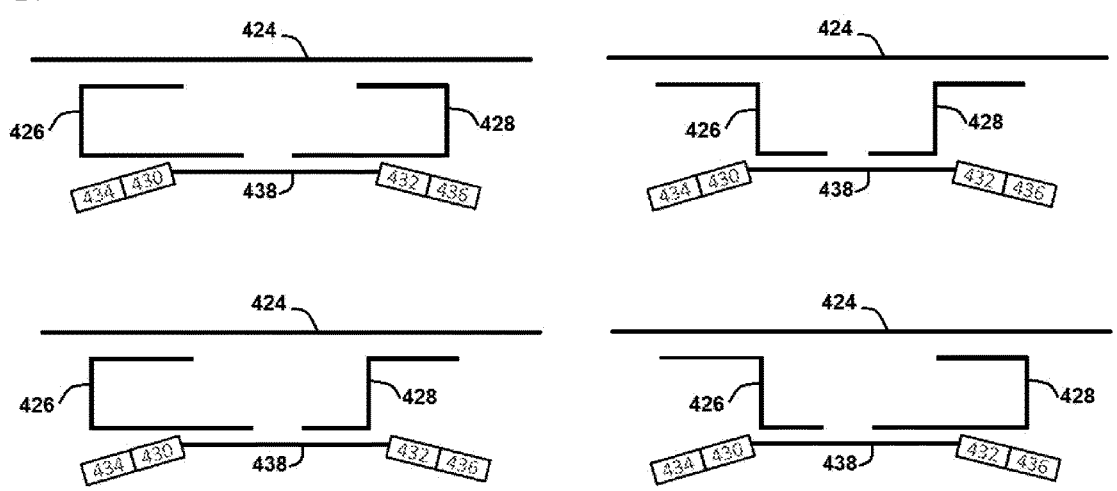

FIG. 4 illustrates one embodiment of a combinatorial address tagging scheme, where nucleic acids in a representative tissue section (shown at 416) are assayed. FIG. 4A shows two probe/address tag conjugates 420 and 422 specifically bound to a biological target 402 of interest. The first probe/address tag conjugate 420 comprises address tag 408, associated with tag 404. Tag 404 can be a universal priming site for amplification of the assay products or an adaptor to enable identification of the address tag 408 and/or other regions of probe/address tag conjugates 420, for example, using sequencing technologies. The second probe/address tag conjugate 422 comprises address tag 406, associated with tag 410. Tag 410 can be a universal priming site for amplification of the assay products or an adaptor to enable identification of the address tag 406 and/or other regions of probe/address tag conjugates 422, for example, using sequencing technologies.

In other embodiments, a biological target 424 is assayed according to the combinatorial address tagging scheme shown in FIG. 4D. Two probes 426 and 428 specifically bind to the biological target 424 of interest. In some embodiments, a portion of each of probes 426 and 428 specifically binds to the target, while each probe also has a portion that specifically binds to an adaptor 438, for example, by specific nucleic acid hybridization. In one embodiment, the probe or probes specifically hybridize to the adaptor. In cases where the biological target is a nucleic acid and the probes are oligonucleotides, the adaptor can specifically bind to the following combinations: 1) the 5' portion of probe 426 and the 3' portion of probe 428; 2) the 3' portion of probe 426 and the 5' portion of probe 428; 3) the 5' portion of probe 426 and the 5' portion of probe 428; or 4) the 3' portion of probe 426 and the 3' portion of probe 428. In certain embodiments, probe 426 or 428 is a linear molecule, a branched molecule, a circular molecule, or a combination thereof. After binding of the two probes to the biological target and the adaptor to the two probes, address tags can be delivered to the sample and coupled to the adaptor. For example, the adaptor can be tagged with address tag 430, associated with tag 434, and/or with address tag 432, associated with tag 436. Tags 434 and 436 can be universal priming sites for amplification of the assay products or sequences to enable identification of the address tags and/or other regions of adaptor/address tag conjugates, for example, using sequencing technologies. In certain embodiments, the address tags are tagged at the same end of the adaptor, or at different ends of the adaptor. In other embodiments, an address tag and/or tag 434 or 436 can be pre-coupled to the adaptor, and the adaptor/address tag or adaptor/tag conjugate or complex is then delivered to the sample in order to bind to the probe bound to the biological target. In certain aspects, the adaptor is a linear molecule, a branched molecule, a circular molecule, or a combination thereof. In some embodiments, after an address tag is attached to each end of the adaptor, the ends can be joined. For example, in FIG. 4D, address tags 434 and/or 436 can comprise structures and/or sequences that allow the two ends of the tagged adaptor 438 to be joined to form a circular construct, to facilitate amplification and/or sequencing of the construct.

In certain embodiments, all or a portion of the adaptor/address tag conjugate sequence is determined, for example, by nucleic acid sequencing. In other embodiments, all or a portion of the probe sequence, and/or all or a portion of the adaptor/address tag conjugate sequence, is determined. For example, a first address tag can be coupled to probe 426, and a second address tag can be coupled to adaptor 438. The duplex formed between probe 426 and adaptor 438 can be subjected to extension and sequencing, to generate a conjugate that comprises sequences of the first address tag, all or a portion of probe 426, all or a portion of adaptor 438, and the second address tag.

The tagging scheme is not limited to the use of two or more probes for the same biological target. For example, in cases where one probe is used, a tag (e.g., an address tag, an adaptor for ligation, or a universal sequencing primer or amplification primer sequence) can be coupled to an adaptor that specifically binds to the probe, rather than to the probe itself.

In some embodiments, at least two adaptors are used. In one aspect, more than one probes are delivered to the sample, and at least one adaptor is provided for each probe that specifically binds to the probe. In one aspect, one or more adaptors are provided for specifically binding to each probe. For example, a pair of adaptors is used to specifically bind to the probe 426 and 428, respectively. In certain embodiments, the adaptors of the pair are DNA molecules that: 1) hybridize or otherwise bind to probe 426 or 428; 2) have free 3' and/or 5' ends that enable the encoding sequences (e.g., address tags 430 and 432) to be attached in a subsequent step or steps, for example, by ligation; 3) are in a form where they can be joined if they are co-localized or in proximity to each other. In some embodiments, part of probe 426 or 428 acts as a splint to enable ligation, or extension and ligation, of the adaptors in the adaptor pair. Additional tags (e.g., an address tag, an adaptor for ligation, or a universal sequencing primer or amplification primer sequence) can be coupled to the adaptor generated by joining the adaptor pair.

FIG. 4B shows an address tagging scheme that may be used for 100 unique sites in a sample. For example, twenty probe/address tag conjugates a1 through a10 and b1 through b10 can be used, with each of a1 through a10 corresponding to a probe/address tag conjugate 420 (comprising an address tag 408) and each of b1 through b10 corresponding to a probe/address tag conjugate 422 (comprising an address tag 406). The address tag comprised in each of a1 through a10 and b1 through b10 may be uniquely identified. Probe/address tag conjugate a1, for example, is delivered to the biological sample through an addressing channel shown as the first horizontal channel in 412. Probe/address tag conjugate a2 is delivered to the biological sample through the second horizontal channel in 412. Probe/address tag conjugate a3 is delivered to the biological sample through the third horizontal channel in 412, and so on. Whereas the "a" probe/address tag conjugates are delivered in ten horizontal channels, the "b" probe/address tag conjugates are delivered in ten vertical channels as shown in 414. For example, probe/address tag conjugate b1 is delivered to the biological sample through the first horizontal channel of 414, probe/address tag conjugate b2 is delivered to the biological sample through the second horizontal channel of 414, and so on. In other embodiments, the "a" tags may be referred to as the "X" tags and the "b" tags as "Y" tags. The intersections or junctions between the horizontal and vertical channels are shown as solid squares. Each intersection or junction can be uniquely identified by the combination of the "a" probe/address tag conjugate and the "b" probe/address tag conjugate delivered to the area in the sample corresponding to the intersection or junction.

FIG. 4C shows a representative tissue section 416 coincident with grid 418. The arrows show how the "a" probe/address tag conjugates and the "b" probe/address tag conjugates are delivered on grid 418 that is coincident with tissue section 416. If, once analyzed, probe/address tag conjugates a1 and b4, e.g., are associated with a target, then that target is present in the tissue section at location (a1, b4).

Figure 5:
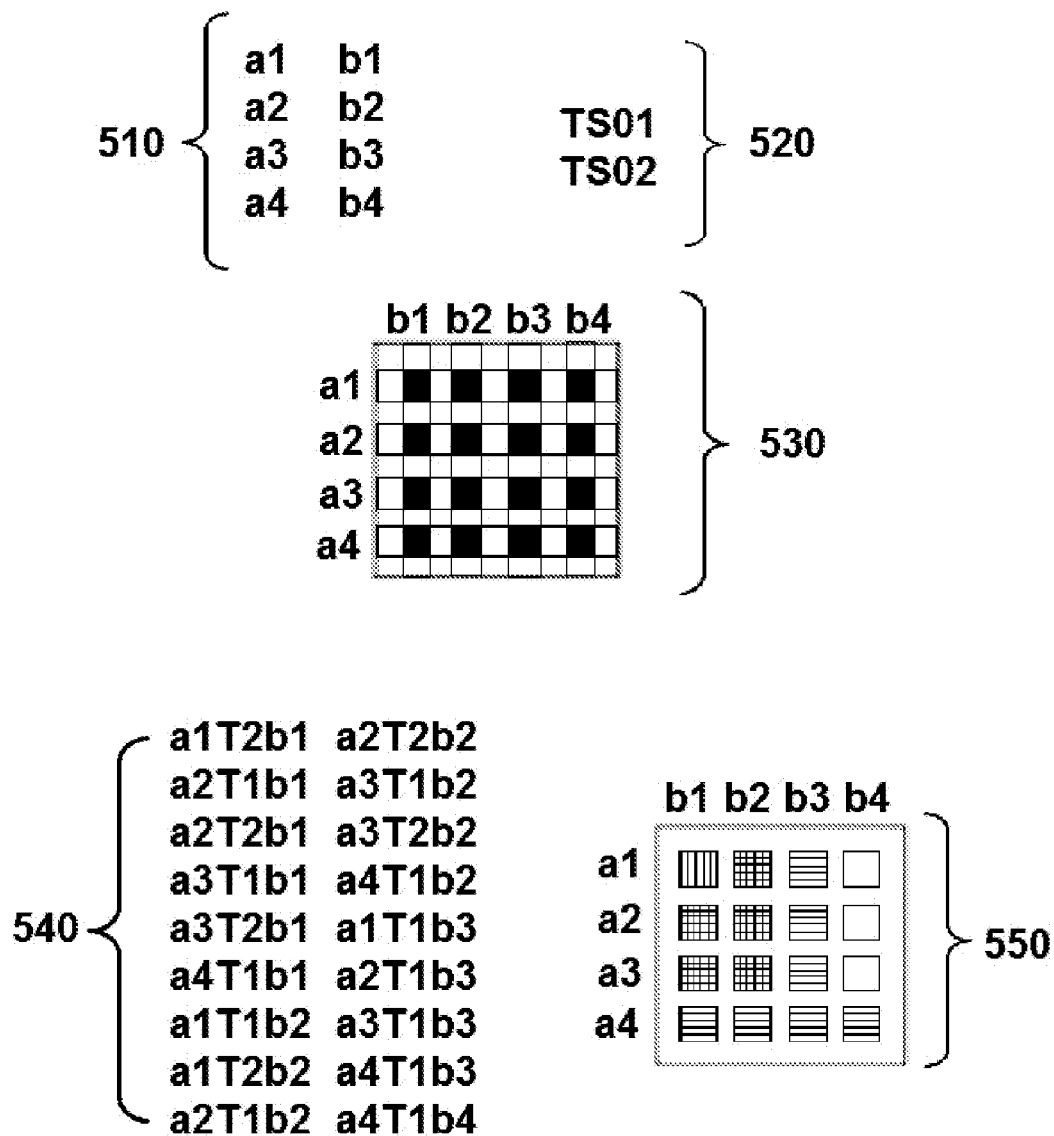
FIG. 5 illustrates a combinatorial addressing scheme applied to a sample, according to one embodiment of the present disclosure.

The methods and assay systems disclosed herein are capable of multiplexing. For example, FIG. 5 provides an address tagging (or "address coding") scheme used in a multiplexed assay. For clarity, two probes TS01 and TS02, specific for target 1 and target 2, respectively, are shown at 520. FIG. 5 shows address tags 510, comprising a1, a2, a3, a4 and b1, b2, b3 and b4. A delivery or dispensing scheme is shown at 530. Like the grid exemplified in FIG. 4, a1 through a4 are delivered to the sample through horizontal channels, and b1 through b4 are delivered to the sample through vertical channels. The intersections between the horizontal and vertical channels are shown as solid squares. Each intersection can be uniquely identified by the combination of the "a" probe/address tag conjugate and the "b" probe/address tag conjugate delivered to the area in the sample corresponding to the intersection.

Probes TS01 and TS02 are delivered to the biological sample and allowed to interact with the entire sample. Probes TS01 and TS02 specifically bind to their corresponding targets if the targets are present in the sample. Unbound probes are then removed, for example, by washing. Address tags 510 are then delivered to the biological sample according to the spatial pattern shown at 530. The address tags are coupled, for example, by ligation (or by extension followed by ligation), to probes that specifically bind to the biological target 1 or biological target 2 in the sample. The coupled constructs (or "probe/address tag conjugates") are then eluted from the biological sample and pooled. In certain embodiments, sequencing adaptors may be added through, e.g., PCR or ligation, if the sequencing adaptors are not already included in the address tags or probe/address tag conjugates. The probe/address tag conjugates are sequenced by, e.g., high throughput or next generation sequencing.

The pool of resulting assay products is shown at 540. For example, presence of the "a1T2b1" product in the pool indicates readout is obtained for TS02 at position (a1, b1) and therefore target 2 is detected at position (a1, b1). Thus, a sequence readout is obtained for only TS01 at positions (a4, b1), (a4, b2), (a1, b3), (a2, b3), (a3, b3), (a4, b3) and (a4, b4) (positions shown with horizontal lines in spatial pattern 550), and a sequence readout is obtained for TS02 only at position (a1, b1) (position shown with vertical lines in spatial pattern 550). A sequence readout is obtained for both TS01 and TS02 at positions (a2, b1), (a3, b1), (a1, b2), (a2, b2), and (a3, b2) (positions shown with cross-hatching in spatial pattern 550). No sequence readout is obtained for either TS01 or TS02 at (a1, b4), (a2, b4) or (a3, b4) (positions shown without shading in spatial pattern 550). Thus, in the biological sample, target 1 is detected in a large portion of the left side and at the bottom of the sample, while target 2 is detected only in the upper left portion of the sample, and neither target is detected in the upper right portion of the biological sample. The differential expression of the two biological targets may be mapped back to the biological sample and to the biological structures or cell types in these locations in the biological sample.

In addition to location information, relative abundance of the biological targets across the multiple sites in the sample can be obtained. For example, if it is found that there are ten times as many a4T1b1 sequences occurring in the data set as compared to a4T1b2 sequences, this would indicate that target 1 is ten times more abundant at location (a4, b1) than at location (a4, b2).

In the case of nucleotide analysis as shown in FIG. 3, by ligating the address tags directly to the probes, only 2n probes are needed for n targets. For example, assaying 100 different targets at 10,000 sites in a sample would require 2×100 probes and 2×100 address tags which are to be coupled to the probes. The total count of assay oligonucleotides would be only 400 (200 probes and 200 address tags), not counting universal primers. In contrast, if the address tags are not decoupled from the probes, the total count of assay oligonucleotides would be (n×X positions)+(n×Y positions), or in the above example, 20,000 oligonucleotides, not counting universal primer sequences. In other embodiments, for each site in the sample, three, four or more address tags may be used, and attached to the probes or one another by varying means and in varying combinations of steps.

The methods and assay systems disclosed herein are particularly suitable for generating a large amount of information with even a modest number of assays. For example, five or more biological targets assayed at five or more positions in the sample generates 25 or more combinations. Using digital sequencing as a readout, the optimum number of sequence reads per combination depends on the sensitivity and dynamic range required, and can be adjusted. For example, if for each combination on average 100 reads are sampled, the total for 25 combination is 2,500 reads. If 1,000 targets are assayed at 1,000 locations with an average sampling depth of 1,000, then $10^9$ reads are required. These numbers, although large, are within the capacity of intrinsically parallel digital sequencing methods, which can generate datasets of billions or even trillions of reads in a reasonable timeframe and at a very low cost per read. Therefore, by varying the numbers of positions or biological targets assayed, or both, and using digital sequencing, large amounts of information can be obtained. In specific aspects, multiple locations are assayed for two or more biological molecules.

Thus, provided herein is an ability to look at many different biological targets in many locations of a sample at the same time, for example, in the same reaction run. In some embodiments, the product of the multiple biological targets being assayed and the multiple sites in the biological sample is greater than about 20. In other embodiments, the product of the multiple biological targets being assayed and the multiple sites in the biological sample is greater than about 50. In other embodiments, the product of the multiple biological targets being assayed and the multiple sites in the biological sample is greater than about 100, greater than about 500, greater than about 1,000, greater than about 10,000, greater than about 25,000, greater than about 100,000, greater than about 500,000, or greater than about 1,000,000. It will be appreciated that even much larger numbers can be contemplated. For example, assaying 10,000 targets per location for 10,000 locations in a sample would generate $10^8$ different assays. In some embodiments, sufficient numbers of sites in a sample can be assayed to reach a resolution on the order of that of single cells. Further, in embodiments where high-throughput digital sequencing is employed, the sequences of at least 1,000 probes or probe/address tag conjugates are typically determined in parallel. More typically, using a digital readout, it is desirable to obtain multiple sequence reads for each assay (defined by a target and a location, i.e., by the identities of an identity tag and an address tag of a target). It is desirable to obtain an average of at least 3 copies per assay, and more typically at least 10 or at least 30 copies per assay, depending on the design of the experiment and requirements of the assay. For a quantitative readout with suitable dynamic range, it may be desirable to obtain at least 1,000 reads per assay. Therefore, if 1,000,000 assays are carried out, the number of sequence reads may be 1 billion or more. With high-throughput digital sequencing, and allowing for redundancy, the sequence of at least 10,000 probes or probe/address tag conjugates can be determined in parallel, or the sequence of at least 100,000, 500,000, 1,000,000, 10,000,000, 100,000,000, 1,000,000,000 or more probes or probe/address tag conjugates can be determined in parallel.

In certain aspects, disclosed herein are methods and assay systems for evaluating differences in the amount and/or activity of biological targets between different locations in a sample and/or between samples. In one embodiment, the method comprises evaluating the differences in quantity of the biological targets at each location in the biological sample. In another embodiment, the method comprises comparing spatial patterns of abundance, expression, and/or activity of one or more biological targets among multiple samples.

Spatially Encoded Protein In Situ Assay

In certain embodiments, it is desirable to correlate spatial patterns of a target polynucleotide expression, for example, mRNA expression patterns within a 2D sample, with histological features of the sample. In certain aspects, the histological features may include the expression pattern of a known marker for the sample, for example, a tissue-specific marker, a cell type marker, a cell lineage marker, a cell morphology marker, a cell cycle marker, a cell death marker, a developmental stage marker, a stem cell or progenitor cell marker, a marker for a differentiated state, an epigenetic marker, a physiological or pathophysiological marker, a marker for a transformed state, a cancer marker, or any combination thereof. In certain aspects, the histological feature comprises tissue morphology, for example, as indicate by the expression pattern of a protein marker. In certain embodiments, in order to obtain spatial information of the sample, e.g., histological features of the sample, expression pattern of a protein marker, and/or tissue morphology, imaging techniques have to be used. For instance, immunohistochemical (IHC) and/or immunofluorescent (IF) imaging may need to be used.

In certain aspects, provided herein are methods called Spatially Encoded Protein In Situ Assays (SEPIA) for multiplexed in situ analysis of proteins. In some embodiments, SEPIA and related assay systems can obtain spatial information on the relative abundance of many proteins in tissue sections. In certain embodiments, the methods and assay systems of the present disclosure are based on the use of antibodies (or other affinity capture agents capable of specifically binding to a target, other than by nucleotide sequence complementarity) that are labeled with an identity tag that identifies the target protein or the antibody, and one or more address tags that identify the location of each of multiple sites in a sample. In one embodiment, there are provided at least two address tags for each site, one of the at least two address tags identifying the location in the tissue section in one dimension (for example, an X coordinate) and the other identifying the location in another dimension (for example, a Y coordinate).

In any of the embodiments disclosed herein, the biological target can be a peptide or a protein, and the methods or assay systems can be used to analyze the presence of antibodies, enzymatic and other protein activities, posttranslational modifications, active and non-active forms of peptides, as well as peptide isoforms in a biological sample. Accordingly, the probes may comprise an active region of an enzyme, a binding domain of an immunoglobulin, defined domains of proteins, whole proteins, synthetic peptides, peptides with introduced mutations, aptamers and the like.

In any of the embodiments disclosed herein, the probes can comprise substrates for enzymes or proenzymes, e.g., kinases, phosphatases, zymogens, proteases, or fragments thereof. In certain aspects, the probes may comprise phosphorylation substrates used to detect proteins involved in one or more signal transduction pathways. In other aspects, the probes can comprise specific protease substrates that associate with specific individual proteases or specific classes of proteases. In other aspects, the probes can comprise different processed forms, isoforms and/or domains of an enzyme. In certain embodiments, a protein-based probe can be conjugated or otherwise linked to an oligonucleotide address tag. In preferred embodiments, the oligonucleotide address tag may comprise a nucleotide sequence component that allows for identification of the protein probe.

In preferred embodiments, antibodies that are conjugated to oligonucleotide tags are compatible with the address tagging scheme disclosed herein. In certain aspects, provided herein are methods and assay systems that are highly multiplexed, scalable, and high-throughput for determining a spatial pattern of abundance, expression, and/or activity of a target protein across multiple sites in a sample, using a nucleic acid readout and independent of imaging for the target protein. In preferred embodiments, provided herein are methods and assay systems to correlate nucleic acid expression patterns (e.g., DNA or RNA expression patterns) with cell type-specific protein marker abundance without the need for imaging for the protein marker, for example, by immunohistochemical or immunofluorescent imaging. In preferred embodiments, spatial resolution of the present methods and assay systems may approach the scale of individual cells. In certain aspects, correlated 2D and 3D maps of RNA and protein abundance can be generated using the present methods and assay systems.

Figure 6:
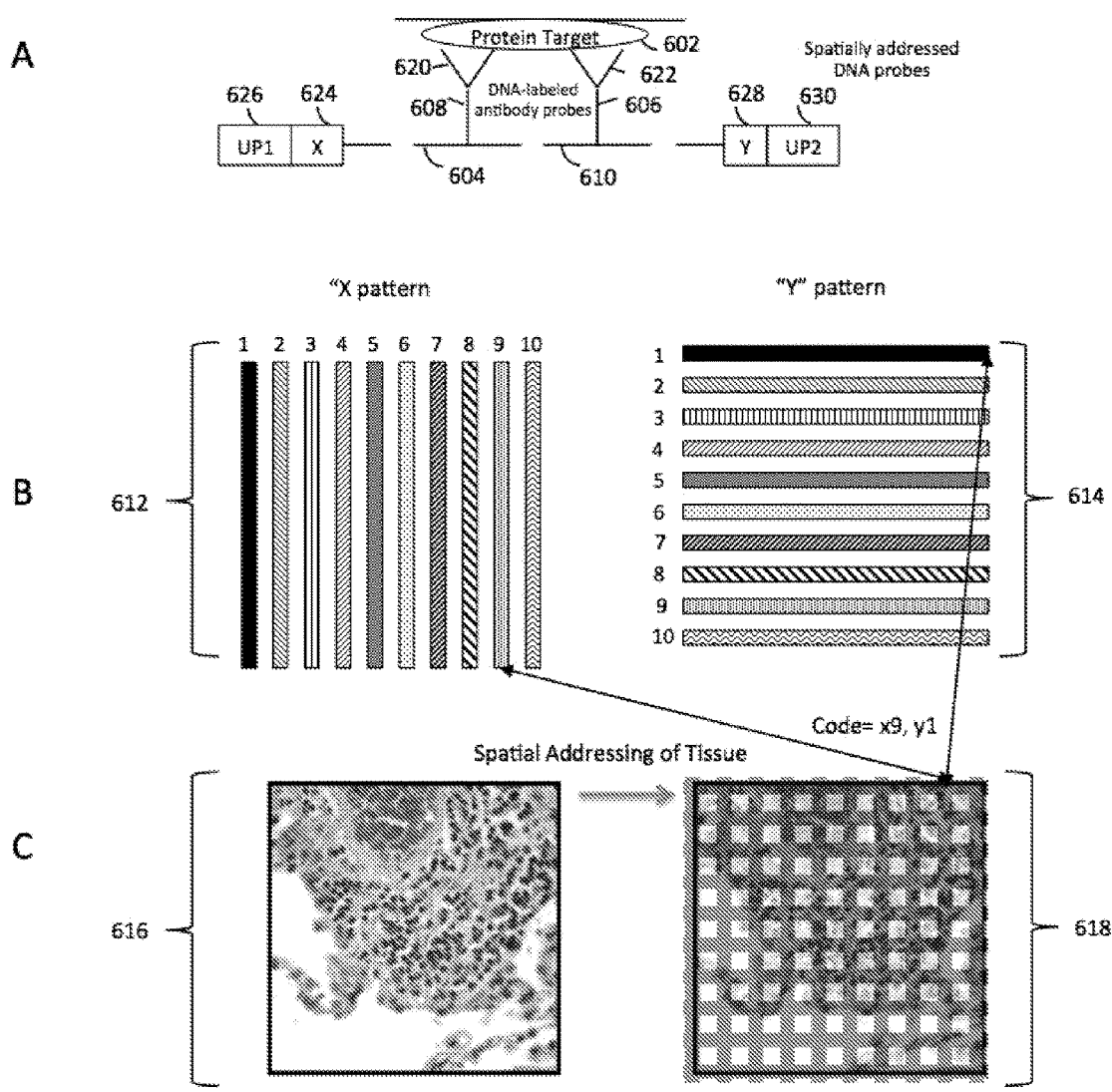
FIG. 6 illustrates multiplexable protein detection assays with combinatorial addressing schemes applied to a sample, according to embodiments of the present disclosure.

As shown in FIG. 6, in one aspect, a highly multiplexable protein detection assay is carried out on a sample 616 (shown in FIG. 6C). In preferred embodiments, sample 616 preserves the spatial organization of cells in a tissue. For example, sample 616 can be a paraffin-embedded or fresh-frozen tissue section fixed to a glass slide. FIG. 6A shows two probes 620 and 622 specifically bound to a protein target 602 of interest. The first probe 620 may comprise target-binding moiety 608, associated with oligonucleotide tag 604. Target-binding moiety 608 and oligonucleotide tag 604 can be conjugated or covalently linked. Target-binding moiety 608 can comprise any affinity capture agents, e.g., antibodies, that specifically bind to protein target 602. Probe 620 may further comprise address tag 624 and tag 626. Tag 626 can be a universal priming site for amplification of the assay products and/or an adaptor to enable identification of the address tag 624 and/or oligonucleotide tag 604 and/or other regions of probe 620, for example, using sequencing technologies. In certain embodiments, tag 626 is conjugated or linked to or otherwise associated with address tag 624, for example, by ligation, extension, ligation followed by extension, or any combination thereof. In one aspect, conjugated, linked or otherwise associated tag 626 and address tag 624 as a whole are conjugated or linked to or otherwise associated with oligonucleotide tag 604. In alternative embodiments, tag 626 and address tag 624 may be separately conjugated or linked to or otherwise associated with probe 620, for example, at target-binding moiety 608 and/or oligonucleotide tag 604.

Similarly, the second probe 622 may comprise target-binding moiety 606, associated with oligonucleotide tag 610. Target-binding moiety 606 and oligonucleotide tag 610 can be conjugated or covalently linked. Target-binding moiety 606 can comprise any affinity capture agents, e.g., antibodies, that specifically bind to protein target 602. Probe 622 may further comprise address tag 628 and tag 630. Tag 630 can be a universal priming site for amplification of the assay products and/or an adaptor to enable identification of the address tag 628 and/or oligonucleotide tag 610 and/or other regions of probe 622, for example, using sequencing technologies. In certain embodiments, tag 630 is conjugated or linked to or otherwise associated with address tag 628, for example, by ligation, extension, ligation followed by extension, or any combination thereof. In one aspect, conjugated, linked or otherwise associated tag 630 and address tag 628 as a whole are conjugated or linked to or otherwise associated with oligonucleotide tag 610. In alternative embodiments, tag 630 and address tag 628 may be separately conjugated or linked to or otherwise associated with probe 622, for example, at target-binding moiety 606 and/or oligonucleotide tag 610.

In certain embodiments, target-binding moiety 606 and target-binding moiety 608 bind to adjacent sites on target 602, so that two free ends of oligonucleotide tags 604 and 610 are brought close to each other. In one embodiment, oligonucleotide tags 604 and 610 may be ligated and the ligation product assayed. In other embodiments, one or both of oligonucleotide tags 604 and 610 may be extended and then ligated to the other probe to form an extended probe comprising target target-binding moiety 606 and target-binding moiety 608. For example, a DNA ligase may be added together with a splint to join two free ends of oligonucleotide tags 604 and 610, and the DNA ligated product can serve as the template detectable by real-time PCR and/or various sequencing technologies. Such a dual targeting approach may be used to increase assay specificity. Other aspects and embodiments of the dual targeting approach that converts specific protein detection into nucleic acid analysis, including the proximity ligation assay described in Fredriksson et al., 2002, Nat Biotechnol 20, 473-7, may be used in the methods and assay systems of the present disclosure. It is also within the present disclosure that in certain embodiments, target-binding moiety 606 and target-binding moiety 608 may bind to different protein targets. When the protein targets are in close proximity, for example, when the two are in the same complex or brought into contact with each other in a reaction, a ligation product may be formed between oligonucleotide tags 604 and 610 and detected.

In certain embodiments, a primary antibody and a secondary antibody may be used. For example, target-binding moiety 606 and/or target-binding moiety 608, instead of specifically binding to target 602 directly, may specifically bind to a primary antibody that specifically recognizes target 602. In this case, target-binding moiety 606 and/or target-binding moiety 608 may be comprised in a secondary antibody. In certain aspects, the approach involving a primary antibody and a secondary antibody may be suitable when target expression in low in a sample, because one molecule of target 602 may be able to bind multiple molecules of a primary antibody, thereby amplifying the signal.

In other embodiments, a biological target 632 is assayed according to the combinatorial address tagging scheme shown in FIG. 6D. Two probes 650 and 652 specifically bind to the biological target 632 of interest. In one embodiment, the first probe 650 comprises target-binding moiety 638, associated with oligonucleotide tag 634, and the second probe 652 comprises target-binding moiety 636, associated with oligonucleotide tag 640. Target-binding moiety 638 and oligonucleotide tag 634 (or target-binding moiety 636 and oligonucleotide tag 640) can be conjugated or covalently linked. In particular embodiments, target-binding moiety 638 or 636 comprises an affinity capture agent, e.g., an antibody, that specifically binds to target 632. In certain embodiments, target 632 comprises a protein moiety, an oligosaccharide or polysaccharide moiety, a fatty acid moiety, and/or a nucleic acid moiety. In some embodiments, each probe has a portion that specifically binds to an adaptor 662, for example, by specific nucleic acid hybridization. In one embodiment, oligonucleotide tag 634 or 640 (or a portion thereof) specifically hybridizes to the adaptor. The adaptor can specifically bind to the following combinations: 1) the 5' portion of oligonucleotide tag 634 and the 3' portion of oligonucleotide tag 640; 2) the 3' portion of oligonucleotide tag 634 and the 5' portion of oligonucleotide tag 640; 3) the 5' portion of oligonucleotide tag 634 and the 5' portion of oligonucleotide tag 640; or 4) the 3' portion of oligonucleotide tag 634 and the 3' portion of oligonucleotide tag 640. In certain embodiments, oligonucleotide tag 634 or 640 is a linear molecule, a branched molecule, a circular molecule, or a combination thereof. After binding of the two probes to the biological target and the adaptor to the two probes, address tags can be delivered to the sample and coupled to the adaptor. For example, the adaptor can be tagged with address tag 654, associated with tag 656, and/or with address tag 658, associated with tag 660. Tags 656 and 660 can be universal priming sites for amplification of the assay products or sequences to enable identification of the address tags and/or other regions of adaptor/address tag conjugates, for example, using sequencing technologies. In certain embodiments, the address tags are tagged at the same end of the adaptor, or at different ends of the adaptor. In other embodiments, an address tag and/or tag 656 or 660 can be pre-coupled to the adaptor, and the adaptor/address tag or adaptor/tag conjugate or complex is then delivered to the sample in order to bind to the probe bound to the biological target.

In certain embodiments, all or a portion of the adaptor/address tag conjugate sequence is determined, for example, by nucleic acid sequencing. In other embodiments, all or a portion of the oligonucleotide tag sequence, and/or all or a portion of the adaptor/address tag conjugate sequence, is determined. For example, a first address tag can be coupled to oligonucleotide tag 634, and a second address tag can be coupled to adaptor 662. The duplex formed between oligonucleotide tag 634 and adaptor 662 can be subjected to extension and sequencing, to generate a conjugate that comprises sequences of the first address tag, all or a portion of oligonucleotide tag 634, all or a portion of adaptor 662, and the second address tag.

The tagging scheme is not limited to the use of two or more probes for the same biological target. For example, in cases where one probe is used, a tag (e.g., an address tag, an adaptor for ligation, or a universal sequencing primer or amplification primer sequence) can be coupled to an adaptor that specifically binds to the probe, rather than to the probe itself.

Additional details of the polynucleotide-protein conjugates used in the present disclosure are disclosed in U.S. Provisional Patent Application Ser. No. 61/902,105, filed Nov. 8, 2013, entitled "Polynucleotide conjugates and methods for analyte detection," the disclosure of which is incorporated by reference in its entirety for all purposes.

In some embodiments, more than one adaptor is used. For example, a pair of adaptors is used to specifically bind the oligonucleotide tag 634 and 640, respectively. In certain embodiments, the adaptors of the pair are DNA molecules that: 1) hybridize or otherwise bind to the protein-DNA conjugates, for example, probe 650 or 652; 2) have free 3' and/or 5' ends that enable the encoding sequences (e.g., address tags 654 and 658) to be attached in a subsequent step or steps, for example, by ligation; 3) are in a form where they can be joined if they are co-localized or in proximity to each other. In some embodiments, part of the oligonucleotide portion of probe 650 or 652 acts as a splint to enable ligation, or extension and ligation, of the adaptors in the adaptor pair. Additional tags (e.g., an address tag, an adaptor for ligation, or a universal sequencing or amplification primer sequence) can be coupled to the adaptor generated by joining the adaptor pair.

In another embodiment, a method disclosed herein makes it easier to carry out protein-based assays at the same time as nucleic-acid based assays. For example, the adaptors can be designed so that they are compatible with the same encoding oligonucleotides used for the nucleic-acid based assays, e.g., RNA-based assays. Thus, two types of binding assays (i.e., detecting a protein target using a protein-polynucleotide conjugate, and detecting a nucleic acid target using a nucleic acid probe) can be carried out in the same reaction volume or in the same experimental run, and the spatial addressing can be performed on both types of probes simultaneously.

In yet another embodiment, the present disclosure provides a control for assays detecting a protein target or a biological target comprising a protein moiety. For example, the nucleic acid portion of the protein-nucleic acid conjugate is used to hybridize to a nucleic acid in the sample. This anchors an "artificial" protein (known composition and abundance based on the abundance of the hybridizing sequence) in the sample. The "artificial" protein can then be detected using a number of means, including protein-binding spatially-addressed assays disclosed herein. The approach is not limited to proteins. For example, small molecules, such as haptens, can also be used. In one aspect, FIG. 6E illustrates the general concept of a method of detecting an RNA with known composition and abundance in the sample, thereby providing a control for the detection of other targets (e.g., protein targets) in the sample. In FIG. 6E, conjugates 662 and 664 each comprises a nucleic acid portion and an antibody-binding portion (circle indicates the antibody-binding portion of conjugate 662, and triangle indicates the antibody-binding portion of conjugate 664). In certain aspects, RNA 666 with known composition and abundance in the sample is specifically bound by the nucleic acid portions of conjugates 662 and 664. In some embodiments, the composition and/or abundance of RNA 666 are determined experimentally, for example, using a method of the present disclosure, and in specific embodiments, simultaneously with the detection of the protein target. In other embodiments, the composition and/or abundance of RNA 666 is derived from prior knowledge or knowledge in the art. In particular embodiments, the antibody-binding portions can be HA or FLAG, and the antibody portions of probes 650 and 652 can be an anti-HA antibody or an anti-FLAG antibody, for example, polyclonal or monoclonal antibodies. Other protein-antibody binding pairs are known in the art and can be used in the present disclosure.

FIG. 6B shows an address tagging scheme that may be used for 100 unique sites in a sample. For example, twenty probes/address tag conjugates X1 through X10 and Y1 through Y10 can be used, with each of X1 through X10 comprising an address tag 624 and each of Y1 through Y10 comprising an address tag 628. The address tag comprised in each of X1 through X10 and Y1 through Y10 may be uniquely identified. Probe/address tag conjugate X9, for example, is delivered to the biological sample in the ninth vertical channel in 612. Whereas the "X" probe/address tag conjugates are delivered in ten vertical channels, the "Y" probe/address tag conjugates are delivered in ten horizontal channels as shown in 614. For example, probe/address tag conjugate Y1 is delivered to the biological sample in the first horizontal channel of 614. In other embodiments, the "X" tags may be referred to as the "a" tags and the "Y" tags as "b" tags.

FIG. 6C shows a representative tissue section 616 coincident with grid 618. The arrows show how the "X" probe/address tag conjugates and the "Y" probe/address tag conjugates are delivered on grid 618 that is coincident with tissue section 616. If, once analyzed, probe/address tag conjugates X9 and Y1, e.g., are associated with a target, then that target is present in the tissue section at location (X9, Y1).

Figure 7:
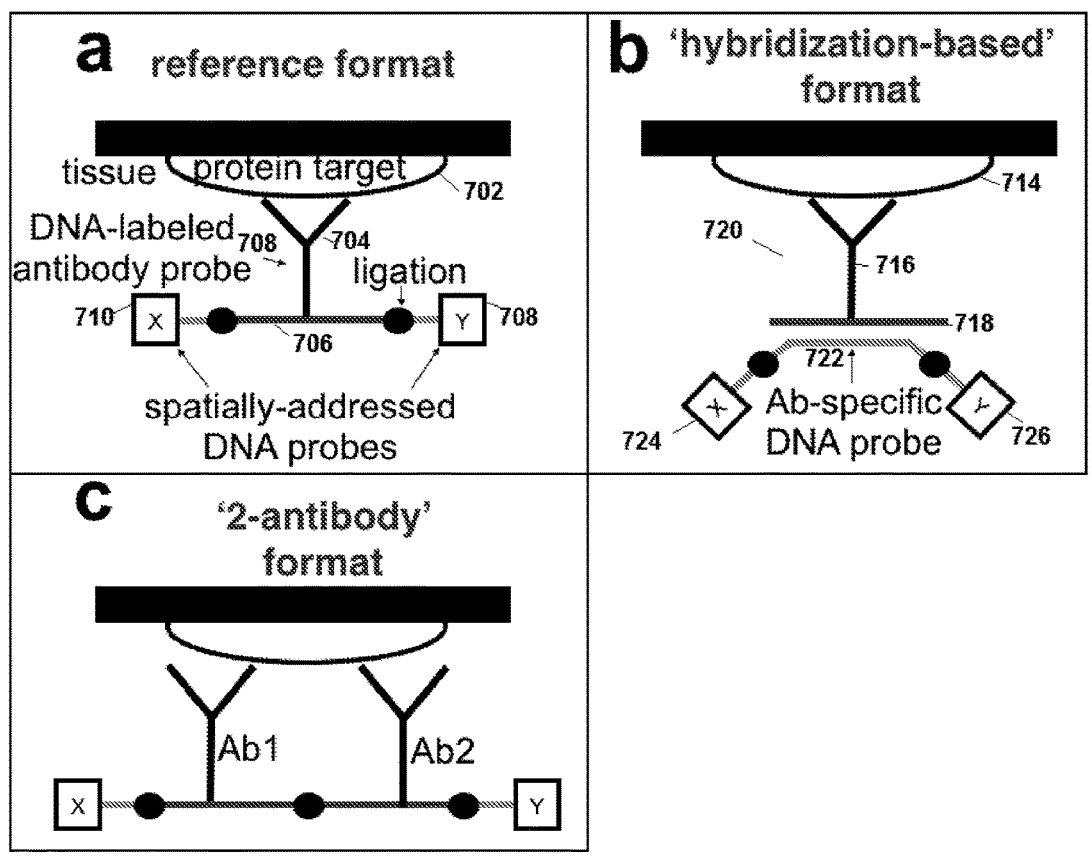
FIG. 7 illustrates exemplary antibody-DNA conjugate configurations, according to certain embodiments of the present disclosure.

Any suitable configuration of the oligonucleotide/antibody (or other target-specific binder) conjugate may be used to convert specific protein detection into nucleic acid analysis. In certain embodiments, for example, as shown in FIG. 7A, probe 708 specifically binds to protein target 702. Probe 708 may comprise target-binding moiety 704, associated with oligonucleotide tag 706. Target-binding moiety 704 and oligonucleotide tag 706 can be conjugated or covalently linked. Target-binding moiety 704 can comprise any affinity capture agents, e.g., antibodies, that specifically bind to protein target 702. Probe 708 may further comprise "X" address tag 710 and "Y" address tag 712. Both address tags 710 and 712 may be conjugated to a universal priming site for amplification of the assay products and/or an adaptor (not shown in FIG. 7) to enable identification of the address tags 710 and 712 and/or oligonucleotide tag 706 and/or other regions of probe 708, for example, using sequencing technologies. Conjugation of the various tags may be accomplished by ligation, extension, ligation followed by extension, or any combination thereof. In some embodiments, address tags 710 and 712 are conjugated to one side of oligonucleotide tag 706 or the other (i.e., 5' or 3' of the sequence), respectively. In alternative embodiments, both address tags 710 and 712 may be conjugated to either 5' or 3' of oligonucleotide tag 706. For example, address tags 710 and 712 may be directly or indirectly conjugated, and address tag 710 or 712 may be directly or indirectly conjugated to either 5' or 3' of oligonucleotide tag 706.

In other embodiments, for example, as shown in FIG. 7B, probe 720 specifically binds to protein target 714. Probe 720 may comprise target-binding moiety 716, conjugated, linked, or otherwise associated with oligonucleotide tag 718. Target-binding moiety 716 can comprise any affinity capture agents, e.g., antibodies, that specifically bind to protein target 714. Probe 720 may further comprise oligonucleotide sequence 722 that specifically hybridizes to oligonucleotide tag 718. In one embodiment, sequence 722 is complementary to oligonucleotide tag 718. Sequence 722 may be conjugated to "X" address tag 724 and "Y" address tag 726. Both address tags 724 and 726 may be conjugated to a universal priming site for amplification of the assay products and/or an adaptor (not shown in FIG. 7) to enable identification of the address tags 724 and 726 and/or sequence 722 and/or other regions of probe 720, for example, using sequencing technologies. Conjugation of the various tags may be accomplished by ligation, extension, ligation followed by extension, or any combination thereof. Similar to FIG. 7A, address tags 724 and/or 726 can be conjugated to either side of oligonucleotide sequence 722 (i.e., 5' or 3' of the sequence), either directly or indirectly.

In further embodiments, for example, as shown in FIG. 7C, a "2-antibody" format may be used. The "2-antibody" format is similar to the dual targeting approach discussed above, for example, in FIG. 6. In this embodiment, two antibodies specific for a protein target are conjugated to an oligonucleotide, which can be directly or indirectly conjugated to the "X" and "Y" address tags and a universal priming site for amplification of assay products and/or an adaptor for sequencing. In some embodiments, the two antibodies may bind to different epitopes or sites on the protein target. In preferred embodiments, binding of both antibodies to the target is required to generate a signal, thus providing higher specificity than using only one antibody. It is also contemplated that more than two antibodies may be conjugated to an oligonucleotide and used in the methods and assay systems of the present disclosure.

As disclosed herein, the methods and assay systems permit high levels of multiplexing. In one embodiment, the probes can be delivered over the entire surface of a 2D sample in a bulk process, and then address tagged by delivering the address tags in a spatially defined pattern. For example, two sets of address tags (the "X" and "Y" tags) can be used in a combinatorial fashion as discussed supra. Once the in situ assay is completed, the assay products are eluted and sequenced. The address tag sequence information identifies the location at which the assay is performed, and the probe sequence information (the identity tag) identifies the protein that is targeted. In one aspect, the frequency of a particular assay product (for example, a sequencing product) in the digital readout can be used to infer the relative abundance of its target in the sample. This information can then be associated with other information, including conventional histological information, and/or transcript abundance obtained via the related Spatially Encoded Genomic Assays (SEGA). In preferred embodiments, the methods and assay systems do not depend on imaging techniques for the spatial information of the target protein. Instead, in preferred embodiments, the spatial pattern of the target protein abundance, expression, and/or activity can be determined by sequencing.

In one embodiment, in order to integrate the protein and gene expression assays, the same address tagging scheme is compatible with and can be used for both assay types. For example, for each of multiple sites in a sample, the same combination of "X" and "Y" address tags can be tagged to an antibody-DNA conjugate for a target protein, and to a probe for a target polynucleotide sequence. In one embodiment, the target polynucleotide or the complement thereof encodes all or a portion of the target protein. Therefore, for each site in the sample, the abundance, expression, and/or activity of the target protein and its corresponding polynucleotide can be detected by assaying for sequencing products with the same set of address tags. In preferred embodiments, the step of analyzing probes or probe/address tag conjugates bound to the target protein and the step of analyzing probes or probe/address tag conjugates bound to the target polynucleotide can be performed in parallel in the same reaction run. In alternative embodiments, different address tags may be coupled to an antibody-DNA conjugate for a target protein, and to a probe for a target polynucleotide sequence, to determine the abundance, expression, and/or activity of the target protein and the target polynucleotide at a given site. Assay results for the target protein and the target polynucleotide can then be integrated for each site in the sample.

Various methods can be used to form an amplifiable construct, for example, by using ligation of proximal probes followed by sequential ligation of a pair of spatial encoding adaptors (address tags) as shown in FIG. 8A. In one embodiment, two DNA probes are hybridized proximal to one another on an RNA target (or template). The probes are subsequently ligated to one another and the quantity of the ligated pair is taken as a measure of the amount of the target present in the sample. In certain cases, however, the efficiency of T4 DNA ligase is reduced when the ligation reaction occurs on an RNA template as compared to a DNA template. In other cases, the ligation efficiency is dependent on the sequence of the DNA probes that are being joined, particularly on the identity of the first few bases on either side of the junction. In some embodiments, a method disclosed herein mitigates both problems. FIG. 8B shows the general principle of the method. In this case, instead of using probes that hybridize in direct proximity on an RNA target, the probes are separated by some distance with non-hybridizing overhanging sequences on their proximal ends. These overhanging sequences are designed to be complementary to a short DNA splint. This splint can be universal for all the probe pairs in a multiplexed assay or can be specific for a given probe pair or subset of probe pairs. The distance between the two probes in a pair can be adjusted to optimize ligation efficiency. There is flexibility in this distance, which provides an additional degree of freedom when designing probes versus the use of proximal probes. Once the probes are hybridized to the RNA target, excess probes are washed away. The splint is hybridized to the overhanging regions at the proximal ends of the probes, and the probes are joined by enzymatic ligation. After ligation, the remaining steps of the assay are performed, for example, ligating the spatial encoding adaptors to each end of the ligated probe pair. In certain aspects, since DNA splinted ligation is more efficient than RNA splinted ligation, a method disclosed herein improves the efficiency at which the two probes are joined. In addition, using a universal splint eliminates the sequence-dependent variation in ligation efficiency between the multiple probe sets in a multiplexed in situ assay. In another aspect, probes can be more easily designed, and more suitable probe sets can be designed, due to increased freedom of varying the distance between probes.

Reagent Delivery Systems

The reagent delivery system of the present disclosure includes instrumentation that allows the delivery of reagents to discrete portions of the biological sample, maintaining the integrity of the spatial patterns of the addressing scheme. Reagent delivery systems of the present assay systems comprise optional imaging means, reagent delivery hardware and control software. Reagent delivery can be achieved in a number of different ways. It should be noted that reagents may be delivered to many different biological samples at one time. A single tissue section has been exemplified herein; however, multiple biological samples may be manipulated and analyzed simultaneously. For example, serial sections of a tissue sample can be analyzed in parallel and the data combined to build a 3D map.

Integral to the assay system of the present disclosure is instrumentation that allows for spatial patterning of reagents onto the biological sample. Technologies for formulating and delivering both biological molecules (e.g., oligonucleotides or antibodies) and chemical reagents (e.g., small molecules or dNTPs) are known in the art, and uses of these instrument systems are known to one skilled in the art and easily adaptable to the assay systems of the present disclosure. One example of a suitable reagent delivery system is the Labcyte™ Echo acoustic liquid handler, which can be used to deliver nanoliter scale droplets containing biological molecules with high precision and reproducibility. One skilled in the art could incorporate this reagent delivery device into the overall system using software to specify the locations to which reagents should be delivered.

Other instruments that can be used for the delivery of agents and/or coding identifiers onto biological samples include, but are not limited to, ink jet spotting; mechanical spotting by means of pin, pen or capillary; micro contact printing; photochemical or photolithographic methods; and the like. For several applications, it may be preferred to segment or sequester certain areas of the biological samples into one or more assay areas for different reagent distributions and/or biological target determination. The assay areas may be physically separated using barriers or channels.

In one exemplary aspect, the reagent delivery system may be a flow-based system. The flow-based systems for reagent delivery in the present invention can include instrumentation such as one or more pumps, valves, fluid reservoirs, channels, and/or reagent storage cells. Reagent delivery systems are configured to move fluid to contact a discrete section of the biological sample. Movement of the reagents can be driven by a pump disposed, for example, downstream of the fluid reagents. The pump can drive each fluid reagent to (and past) the reaction compartment. Alternatively, reagents may be driven through the fluid by gravity. US Pub. Nos. 20070166725 and 20050239192 disclose certain general purpose fluidics tools that can be used with the assay systems of the present disclosure, allowing for the precise manipulation of gases, liquids and solids to accomplish very complex analytical manipulations with relatively simple hardware.

In a more specific example, one or more flow-cells can be attached to the substrate-affixed biological sample from above. The flow-cell can include inlet and outlet tubes connected thereto and optionally an external pump is used to deliver reagents to the flow-cell and across the biological sample. The flow cells are configured to deliver reagents only to certain portions of the biological sample, restricting the amount and type of reagent delivered to any specific section of the biological sample.

In another aspect, a microfluidic system can be integrated into the substrate upon which the biological sample is disposed or externally attached on top of the substrate. Microfluidic passages for holding and carrying fluid may be formed on and/or above the planar substrate by a fluidics layer abutted to the substrate. Fluid reagents can be selected and delivered according to selective opening and closing of valves disposed between reagent reservoirs.

Pumps generally include any mechanism for moving fluid and/or reagents disposed in fluid. In some examples, the pump can be configured to move fluid and/or reagents through passages with small volumes (i.e., microfluidic structures). The pump can operate mechanically by exerting a positive or negative pressure on fluid and/or on a structure carrying fluid, electrically by appropriate application of an electric field(s), or both, among other means. Exemplary mechanical pumps may include syringe pumps, peristaltic pumps, rotary pumps, pressurized gas, pipettors, etc. Mechanical pumps may be micromachined, molded, etc. Exemplary electrical pumps may include electrodes and may operate by electrophoresis, electroendosmosis, electrocapillarity, dielectrophoresis (including traveling wave forms thereof), and/or the like.

Valves generally include any mechanism for regulating the passage of fluid through a channel. Valves can include, for example, deformable members that can be selectively deformed to partially or completely close a channel, a movable projection that can be selectively extended into a channel to partially or completely block a channel, an electrocapillary structure, and/or the like.

An open gasket can be attached to the top of the biological sample and the sample and reagents can be injected into the gasket. Suitable gasket materials include, but are not limited to, neoprene, nitrile, and silicone rubber. Alternatively, a watertight reaction chamber may be formed by a gasket sandwiched between the biological sample on the substrate and a chemically inert, water resistant material such as, but not limited to, black-anodized aluminum, thermoplastics (e.g., polystyrene, polycarbonate, etc.), glass, etc.

Microfluidic devices that can be used in the methods and systems of the present disclosure are disclosed in detail in U.S. Application Ser. No. 61/839,320, filed Jun. 25, 2013, entitled "Spatially encoded biological assays using a microfluidic device," and in International Application No. PCT/US2014/044191, filed Jun. 25, 2014, entitled "Spatially encoded biological assays using a microfluidic device," the disclosures of which are incorporated herein in their entireties by reference for all purposes.

In an optional embodiment, the assay system comprises imaging means to determine features and organization of the biological sample of interest. The images obtained, e.g., may be used to design the delivery pattern of the reagents. Imaging means are optional, as an individual can instead view the biological sample using, e.g., a microscope, analyze the organization of the biological sample, and specify a spatial pattern for delivery assay reagents. If included, the delivery system can comprise a microcircuit arrangement including an imager, such as a CCD or IGFET-based (e.g., CMOS-based) imager and an ultrasonic sprayer for reagent delivery such as described in US Pub. No. 20090197326, which is incorporated herein by reference. Also, it should be noted that although an X-Y grid configuration is illustrated herein, other configurations can be used, such as, e.g., following the topology of a tissue sample; targeting certain groups of cells, cell layers and/or cell types in a tissue, and the like.

In yet another alternative, the reagent delivery system controls the delivery of reagents to specific patterns on a biological sample surface using semiconductor techniques such as masking and spraying. Specific areas of a biological sample can be protected from exposure to reagents through use of a mask to protect specific areas from exposure. The reagents may be introduced to the biological sample using conventional techniques such as spraying or fluid flow. The use of masked delivery results in a patterned delivery scheme on the substrate surface.

In one aspect, the reagent delivery instrumentation is based on inkjet printing technology. There are a variety of different ink jetting mechanisms (e.g., thermal, piezoelectric) and compatibility has been shown with aqueous and organic ink formulations. Sets of independently actuated nozzles can be used to deliver multiple reagents at the same time, and very high resolutions are be achieved.

In order to target specific sites of interest, an informative image of the biological sample to be assayed may be used to assist in the reagent delivery methods and associated encoding scheme. Sample regions of the biological sample can be identified using image processing (e.g., images of cell types differentiated by immunohistochemistry or other staining chemistries) integrated with other features of the assay system. In some aspects, software is used to automatically translate image information into a reagent delivery pattern. In some embodiments, a mechanism to register and align very precisely the biological sample for reagent delivery is an important component of the assay systems. Mechanisms such as the use of fiducial markers on slides and/or other very accurate physical positioning systems can be adapted to this purpose.

The present methods and assay systems may comprise a complete suite of software tailored to the methods or assay systems. Optionally, oligonucleotide design software is used to design the encoding nucleotides (and in embodiments where nucleic acids are assayed, the target-specific oligonucleotides) for the specific assay to be run, and may be integrated as a part of the system. Also optionally, algorithms and software for reagent delivery and data analysis (i.e., sequence analysis) may be integrated to determine assay results. Integrated data analysis is particularly useful, as the type of dataset that is generated may be massive as a consequence of scale. Algorithms and software tools that are specifically designed for analysis of the spatially-associated data generated by the assay systems, including pattern-analysis software and visualization tools, enhance the value of the data generated by the assay systems.

In certain aspects, the assay system comprises processes for making and carrying out the quality control of reagents, e.g., the integrity and sequence fidelity of oligonucleotide pools. In particular, reagents are formulated according to factors such as volatility, stability at key temperatures, and chemical compatibility for compatibility with the reagent delivery instrumentation and may be analyzed by instrumentation integrated within the assay system.

Applications of Assay System

It will be apparent to one skilled in the art upon reading the present disclosure that there are numerous important areas of biological research, diagnostics, and drug development that will benefit from a high throughput multiplexed assay system that can measure simultaneously the amount and spatial location of a biological target in a biological sample. For example, combining the ability to estimate the relative abundance of different RNA transcripts with the ability to reconstruct an image of spatial patterns of abundance across many locations, which may be as small as or even smaller than individual cells, in a tissue enables many different areas of basic research. The following are exemplary uses and are by no means meant to be limiting in scope.

In one embodiment, the assay systems and devices disclosed herein can discriminate different tissue types on the basis of tissue-specific differences in gene expression. In one aspect, the assay systems and devices disclosed herein can be used to assay and discriminate mRNA and hnRNA, and therefore can be used for parallel analysis of RNA processing in situ. In one aspect, probes are designed to target introns and/or exons. In one aspect, intronic probes give signal from hnRNA, but not from mRNA. The gDNA background signal can be measured using selective pretreatments, with DNase and/or RNase. In one aspect, splice-site specific probes that are selective for spliced RNAs may be designed and used. In certain embodiments, a combination of intronic probes, exonic probes, and/or splice-site specific probes may be used to identify the relative level of processing intermediates and their differences between different cells in a tissue section. In general, RNA may be bound to proteins of various types, and hnRNA, in particular, is complexed with proteins to form hnRNP (heterogeneous nuclear ribonucleoprotein). In one embodiment, the devices and assay systems disclosed herein can be used to perform highly parallel in situ footprinting experiments. In certain aspects, instead of targeting 1,000 different RNAs, probes can be tiled densely through a smaller number of RNAs in order to generate a signal profile along the molecule. Relative changes in this profile between cell types would then indicate differences in availability of the RNA, at the specific locations assayed.

In one example, 3-dimensional patterns of gene expression are determined by analyzing a series of tissue sections, in a manner analogous to image reconstruction in CT scanning. Such a method can be used to measure changes in gene expression in disease pathology, e.g., in cancerous tissue and/or a tissue upon injury, inflammation, or infection. With the assay systems of the invention, more detailed information on gene expression and protein localization in complex tissues is obtained, leading to new insights into the function and regulation both in normal and diseased states, and provides new hypotheses that can be tested. For example, an assay system of the invention may enable some of the insights gained from many individual studies and larger programs like ENCODE (Birney, et al., Nature, 447: 799-816 (2007)) and modENCODE to be integrated at the tissue level. The assay systems also aid computational efforts to model interacting networks of gene expression in the field of systems biology.

The assay systems also provide a novel approach to analysis of somatic variation, e.g., somatic mutations in cancer or variability in response to infectious organisms. For example, tumors are typically highly heterogeneous, containing cancer cells as well as genetically normal cells in an abnormal local environment. Cancer cells undergo mutation and selection, and in this process it is not unusual for local clones to develop. Identifying relatively rare somatic mutations in the context of tumors may enable the study of the role of key mutations in the selection of clonal variants. Transcriptional patterns associated with angiogenesis, inflammation, or other cancer-related processes in both cancer and genetically normal cells can be analyzed for insights into cancer biology and assist in the development of new therapeutic agents for the treatment of cancers. In another example, individuals have varying susceptibility to infectious organisms, and the assay systems of the invention can be used to study the interaction between microbes and tissues or the various cell types within the tissue.

Importantly, in addition to providing spatially-associated information, the invention allows a great increase in the sensitivity of detecting rare mutations, as signal to noise can be dramatically increased since only a small location is assayed in any given reaction. In a typical assay for rare mutations in a mixed sample, the sample is treated in bulk, i.e., nucleic acids are extracted from many cells into a single pool. Thus, if a mutation is present in one cell in 10,000, it must be detected against a background of normal DNA from ~10,000 cells. In contrast, with the assay systems of the invention many cells can be analyzed, but individual cells or small groups of cells would be identified by the spatial coding system. Therefore, in the assay systems of the present invention, background is reduced by orders of magnitude, greatly increasing sensitivity. Furthermore, the spatial organization of mutant cells can be observed, which may be particularly important in detecting key mutations in tissue sections in cancer. Already molecular histological analyses are yielding insights into cancer biology and may have potential for use in diagnostics. The technology of the invention promises to greatly increase the power of such approaches.

The following exemplary embodiments and examples are intended to further describe and illustrate various aspects of the invention, but not to limit, the scope of the invention in any manner, shape, or form, either explicitly or implicitly.

Example 1 Proof of Concept of the Addressing Scheme and Scalability

A model system was developed using a microarray to demonstrate a working multiplexed spatially encoded abundance assays for polynucleotide targets. The basic design validates the concept of the assay, and the addressing scheme, and establishes a working assay prior to addressing issues related to the analysis of a more complicated biological sample.

A microarray was used as a proxy for a tissue section. The target sequences of the microarray were fully specified, so that the composition of the targets was known and was varied systematically, simplifying analysis by next-generation sequencing. One of skill in the art would appreciate that similar assays can be performed on various samples including tissue sections, and for various targets including polynucleotide or protein targets, as well as other biological targets, according to the present disclosure.

A 16-Plex×8-Site Assay Using 8-Section Microarray as Artificial Sample

This 16-plex×8-site assay was performed using a custom DNA microarray (Agilent) as an artificial sample. Eight sites were used because of the commercial availability of 8-section microarrays. Sixteen different target sequences were each assayed over a 128-fold range in DNA amount. Differences in DNA amount were obtained by varying the surface area over which each sequence was synthesized. Differences in DNA amount were detected over the entire range for all sixteen targets, using next-generation sequencing as the readout. This example demonstrated a working multiplex assay using a microarray as an artificial sample, and the spatial encoding accuracy for the model system.

Example 2 A Demonstration of Spatial Encoding Using a Spotted Microarray

Scalability of both the spatial addressing and assay systems is demonstrated by carrying out a 24-plex×24-site assay using a microarray model system.

The amount of biological target, here a DNA target sequence, at each assay location is systematically varied on the microarray substrate. For example, in a microarray with 50 micron spot size (center to center), a 1 mm² area contains ~400 spots. The region around each site is optionally occupied by a region that is devoid of these spots to allow individual resolvability of the target sequences. Alternatively, the spots may be clustered, with two or more directly adjacent spots surrounded by or adjacent to a region that is devoid of target sequences.

In order to demonstrate that spatial addressing or encoding is accurate, the sites comprise different target compositions to show that the assay readout matches the expected composition of each site. With 24 target sequences, a simple digital pattern is made with each site having a different set of 12 targets present and 12 targets absent, to make a binary code (0=absent, 1=present). The assay readout is then determined to show that the detected regions match the expected signal after spatial decoding. In this particular example, the code (address tag) space is large enough (2^24) so that even a few errors would not result in different codes being mixed up. Moreover, this design allows identification of errors and allows estimation not only of accuracy of spatial encoding but also of accuracy calling the presence or absence of target sequences.

The ability to detect quantitative differences is evaluated by generating dose-response curves for each of the 24 assays that are carried out at each site in a 24-site assay. This allows estimation of the limit of detection, dynamic range, and power to detect a given fold-change across the range.

In one aspect, a latin square design is used to represent individual targets at different ratios by varying the number of features for each target. In other words, with multiple spots in a site, the number of spots allocated to each of the 24 target sequences can be varied and each of the 24 sites can have a different composition. A 1×3 inch microarray is sufficiently large to permit multiple replicates. This larger set of 24 sequences will require deconvolution, and this is accomplished by using high throughput techniques such as next-generation sequencing technologies (e.g., SOLiD™ technology (Life Technologies, Inc., Carlsbad, Calif.) or Genome Analyzer (Illumina, Inc., San Diego, Calif.)). The use of the 24-plex assay demonstrates both the accuracy of spatial encoding and decoding, and the quantitative response of the assay system.

Example 3 Assays for Preserved Samples and Biological Samples

Genomic DNA is assayed in order to characterize variation in coding and regulatory sequences, such as single nucleotide polymorphisms (SNPs) or mutations, small insertions and deletions (indels), copy number variants such as gene deletions or amplifications, and genetic rearrangements such as translocations, all of which may be functionally significant in cancer and other diseases. Genomic sequence variation as a function of position in the sample may indicate somatic mosaicism in the sample. In cancer samples, mutations may provide prognostic or diagnostic markers that may be useful in determining the best course of treatment. Mutations may identify regions of the sample that contain cancer cells and assist in distinguishing them from normal cells, or cells in the tumor microenvironment that are genetically normal at the sequence level but perturbed in other ways as a result of the influence of cancer cells. In order to distinguish signal generated from DNA targets from those generated by RNA targets, probes can be designed to hybridize to non-coding sequences that are not transcribed. Alternatively, or in order to confirm the specificity of DNA targeting, RNA may be degraded by treatment with RNase. Genomic DNA is also assayed in order to obtain information about its organization and to provide information on the state of activation of certain genes. For example, the ability of probes to bind to DNA may be used as an indicator of whether DNA is condensed or otherwise inaccessible, or whether DNA is in an open conformation for transcription. This type of determination can benefit from comparative analysis of samples in which genes are differentially active. Similarly it may be useful to relate information about RNA and/or protein abundance to information about the activation state of genes. Other types of information are obtained from analysis of epigenetic markers associated with genomic DNA, such as methylation state and the presence of histones and other proteins and modifications.

The handling of small absolute numbers of product molecules generated from very small or compromised samples are enhanced to counter the issue of low recovery efficiency; that is, elution is efficient and losses resulting from adsorption of molecules to surfaces are prevented. An approach to addressing the latter issue is to include a carrier material, such as glycogen or carrier nucleic acids.

In order to adapt the assay to a biological sample and make the tissue section RNA assays as informative as possible, pre-existing information on expression levels in specific tissues to target transcripts across a range of abundances are used in the assay design. Both high abundance transcripts, as well as some medium and low abundance transcripts, are targeted to enable an initial assessment of the quantitative performance characteristics of the assay. In this assay, a control RNA template is immobilized to a solid support in order to create an artificial system. The assay is performed using T4 DNA ligase, which can repair nicks in DNA/RNA hybrids. Assays are carried out on matched slides, or different sections of the same slide, where in one case gDNA is assayed and in the other RNA is assayed. When assaying gDNA the slide can be pretreated with RNase, and when assaying RNA the slide is pretreated with DNase. Results of the assay are confirmed by extracting gDNA or RNA and quantitating the relative amounts by qPCR or RT-qPCR, respectively.

Example 4 Multiplex Spatially Encoded Polynucleotide Abundance Assays

This example describes representative multiplex spatially encoded abundance assays for polynucleotide targets. One of skill in the art would appreciate that similar assays can be performed for protein targets, as well as other biological targets, according to the present disclosures.

A 57-Plex Assay Using Formalin-Fixed, Paraffin-Embedded (FFPE) Samples

A scheme using ligation of proximal probes followed by sequential ligation of a pair of spatial encoding adaptors (address tags) was used to form an amplifiable construct. For example, as shown in FIG. 8A, two target-specific probe oligos were ligated together following in situ hybridization. A unique adaptor or address tag encoding the X position was introduced via a microfluidic channel and ligated to the 5' end of the probes. A second address tag encoding the Y position was similarly installed to the 3' end of the probes. The address tags contained universal priming sites that allowed installation of additional sequencing adaptors via PCR. The final construct is a substrate for next-generation sequencing.

A 57-plex assay was performed using a pool of probes for 57 targets on commercially sourced FFPE sections of normal human liver and pancreas (Pantomics). The pool included probes for 18 liver specific targets, 19 pancreas specific targets, 4 housekeeping targets, 6 custom-generated negative controls sequences, and 10 pluripotency markers. All liver-specific probes were strongly enriched in liver and all but 3 of the pancreas-specific probes were strongly enriched in pancreas. These 3 probes had very few total counts so it is likely that they were sequences that hybridized or ligated inefficiently and thus were not reporting accurately. The results of this assay were consistent with published data for expression in normal liver and pancreas (BioGPS, available at biogps.org/#goto=welcome).

A number of different reagent delivery technologies, including random-access methods such as inkjet and pin-spotting, can be used for the multiplex assays. A system using microfluidic flow-channel devices was chosen for several reasons. First, soft-lithographic techniques allow rapid development of such devices at a fraction of the cost and time needed to develop or buy a suitable instrument for printing or spotting reagents. Second, the size of the sampling area can be strictly defined using microfluidic devices, whereas printed droplets of reagent would likely spread non-uniformly on the surface of an FFPE sample and yield sampling areas of varying size and shape. Third, the reagent delivery system using microfluidic devices does not require precise alignment of the sample. This feature allows sequential ligation of the two encoding positional adaptors (i.e., the two address tags). Compared to simultaneous ligation of the two address tags, sequential ligation minimizes the formation of undesired products. For reagent delivery technologies using inkjet or pin-spotting, the location of each droplet or spot of the first address tag must coincide with a droplet or spot of the second address tag in order to form the full construct during sequential ligation. This would require that precise registration of the sample be preserved throughout both printing steps. In contrast, the microfluidic device based method and system uses a pair of microfluidic devices each having a set of parallel channels, where the first and second devices have their channels oriented perpendicular to one another as shown in FIG. 9A.

Figure 9:
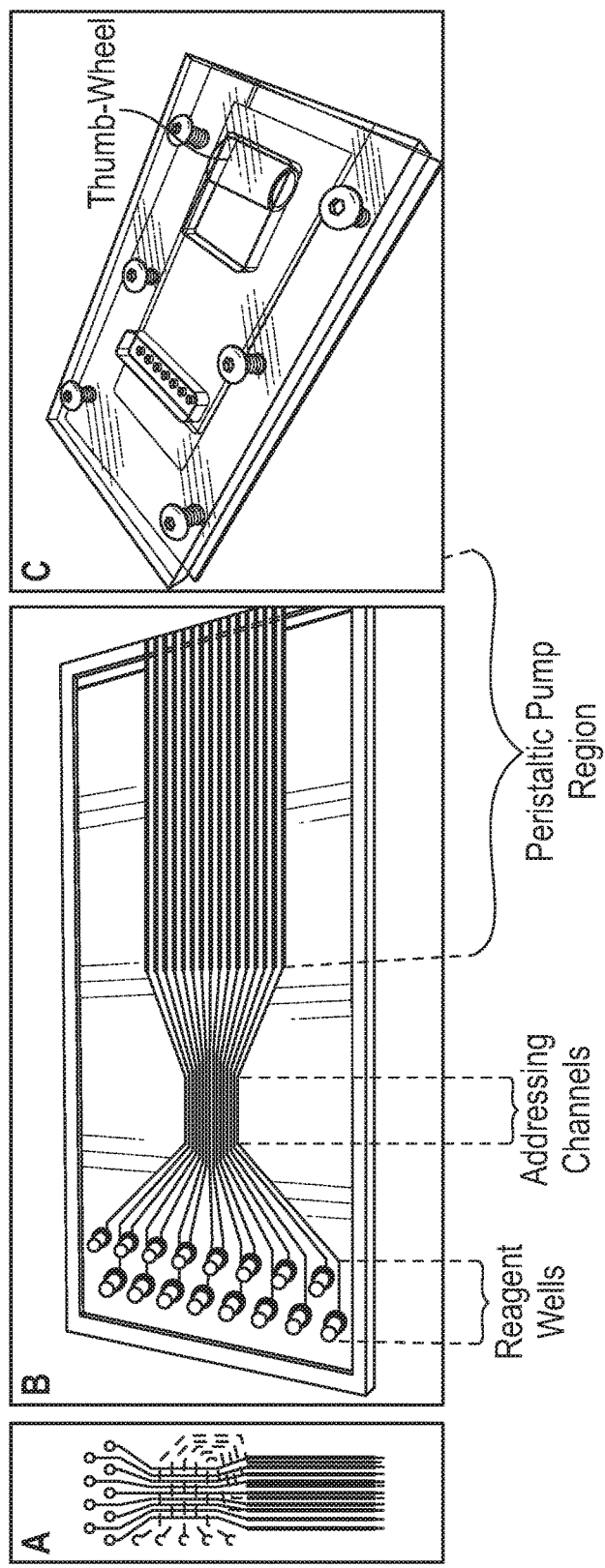
FIG. 9 illustrates a microfluidic addressing device, according to one embodiment of the present disclosure.

A microfluidic addressing device is shown with overlayed layout for a pair of addressing devices in FIG. 9A, a poly(dimethylsiloxane) (PDMS) elastomer device with 16×16 channels and 100 µm channel width in FIG. 9B, and an assembled device with the clamp and peristaltic pump mechanism in FIG. 9C.

The geometry of the devices defines a rectangular array of junctions, each having an area that is defined by the width of the two channels. If each channel receives a different address tag, the result is a unique pair of identifying address tags for each junction or intersection in the array. Fluid flow in microfluidic devices is usually driven by external syringe pumps or vacuum and often requires a complex plumbing setup including connections between the microscopic channels and the macroscopic components of the system. The reagent delivery system used in the example is a self-contained system for loading reagents into the channels. The device is cast out of a PDMS elastomer and includes reagent reservoirs, and microscopic addressing channels, each of which is connected to a larger peristaltic pump channel. The device is applied to the surface of an FFPE sample and clamped in place. A thumb-wheel is applied across all the pump channels and the rolling action draws the liquid from each reservoir through the addressing channel where it contacts the tissue sample and the address tag is ligated onto the hybridized probes. After the first ligation, the device is removed and the sample washed. The second, perpendicular device is used to install the second set of address tags. Only the probes under the area at the intersection of two channels receive both address tags. The devices can be cleaned and reused.

Figure 10:
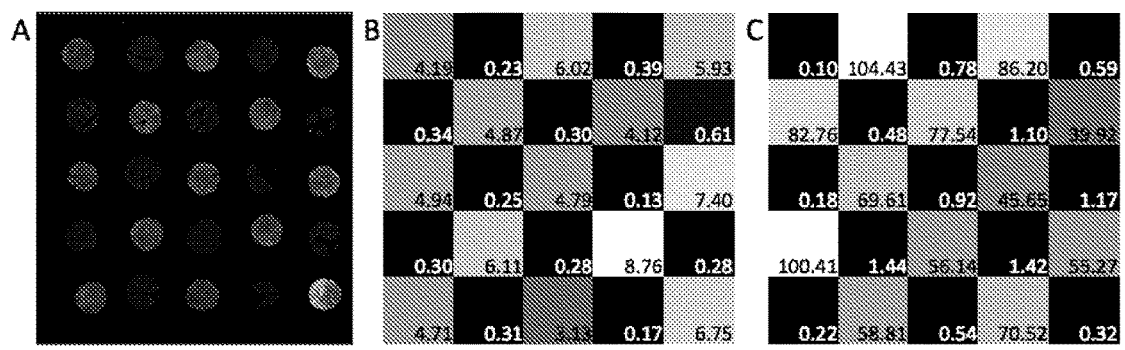
FIG. 10 provides an immunofluorescence image (FIG. 10A) and representative expression maps (FIG. 10B-C) generated according to some embodiments of the present disclosure.

A set of microfluidic devices with a 5-site×5-site layout was fabricated, to match a set of custom-designed tissue microarrays (TMAs) that contained a corresponding 5×5 checkerboard pattern was produced. The TMAs contained the same commercially sourced FFPE sections of normal human liver and pancreas (Pantomics) used above in this example, arranged in a checkerboard pattern. This known pattern of tissue spots on the array was used to verify the accuracy of the spatial encoding system. FIG. 10 shows an immunofluorescence image of a TMA as well as expression maps generated by the assay system using the microfluidic reagent delivery system. FIG. 10A shows immunofluorescence (IF) image of a custom TMA stained with two liver specific antibodies: PYGL, specific to hepatocytes and Annexin A2, specific to bile-duct cells. The reference was Protein Atlas, available at www.proteinatlas.org. The brightly stained spots are liver tissue and dim spots are pancreas. FIG. 10B shows a map of the sum of the 22 most abundant liver-specific genes by abundance, normalized to housekeeping genes (GAPDH and ActB). Each square corresponds to the signal mapped to one junction, a 500 µm×500 µm area centered on one of the tissue cores of the TMA. FIG. 10C shows a map of the sum of the 22 most abundant pancreas genes by abundance, normalized by housekeeping genes. The addressing channels of the microfluidic devices used are 500 µm wide at a 2 mm pitch with a depth of 50 µm, which corresponds to a "virtual-volume" of 12.5 nL that encompasses the intersection of the perpendicular channels.

These results demonstrate that mapped sequencing data using the multiplex system reproduced the expected expression pattern of the tissue sample, and that the multiplex assay is compatible with immunofluorescence imaging, allowing the determination of cell types based on protein markers and correlation with gene expression data.

A 134-Plex Assay Using Formalin-Fixed, Paraffin-Embedded (FFPE) Samples

A probe pool and two device layouts were developed. The probe pool consisted of 134 targets representing 69 unique genes shown in Table 1. When reading out expression by sequencing, a few highly expressed genes can account for the majority of the reads, limiting dynamic range of the assay. This issue was mitigated by attenuating some of the most highly expressed genes in the pool. This was accomplished by adding in attenuator probes in known ratios with the active probes. An attenuator probe lacks a 5' phosphate necessary for ligation, preventing production of an amplifiable product and thus decreasing the signal from that target. Table 2 shows the results of attenuation of the top 5 genes. Before attenuation they accounted for 73% of the reads whereas afterwards they accounted for less than 18%. This strategy can be used to achieve very high levels of multiplexing with current sequencing technology while still achieving high dynamic range.

TABLE 1

List of genes and number of unique targets per gene in 134-plex probe pool.

| Pluripotency | | Liver | | Liver | | Pancreas | | Pancreas | |
|---|---|---|---|---|---|---|---|---|---|
| AURKB | 3 | AGXT | 2 | KRT19 | 2 | AQP8 | 2 | DPEP1 | 2 |
| HMGB3 | 2 | ALDO | 2 | KRT7 | 2 | CARS | 2 | GP2 | 2 |
| JARID2 | 3 | APOB | 2 | MCAM | 2 | CEL | 2 | PRSS1 | 2 |
| LIN28A | 1 | BHMT | 2 | MYH9 | 2 | CLPS | 2 | SOX9 | 2 |
| SOX2 | 1 | CPB2 | 2 | POGZ | 2 | CPA1 | 2 | WDR38 | 2 |
| Housekeeping | | CYP2A6 | 2 | SMARCA4 | 2 | GCG | 2 | ASB9 | 2 |
| ACTB | 2 | CYP2C8 | 2 | ALB | 2 | INS | 1 | CHGA | 2 |
| GAPDH | 2 | HPX | 2 | ARG1 | 2 | PNLIP | 2 | GAD2 | 2 |
| H2AFX | 2 | SAA4 | 2 | CD14 | 2 | PNLIPRP2 | 2 | INSM1 | 2 |
| Controls | | SERPIND1 | 2 | MBL2 | 2 | PPP4C | 2 | NCAM1 | 2 |
| 18S | 3 | VTN | 2 | PYGL | 2 | REG1B | 2 | PAX6 | 2 |
| Rand Neg | 3 | CA9 | 2 | SLC27A5 | 2 | SEL1L | 2 | PPY | 2 |
| Other | | EPB41L2 | 2 | STOM | 2 | CA12 | 2 | SV2A | 2 |
| FXR1 | 2 | HNF1B | 2 | | | CPA2 | 2 | UCHL1 | 2 |

TABLE 2

Attenuation of top 5 assay targets

| | Fraction of Reads | | Atten. |
|---|---|---|---|
| Probe Name | w/o Atten. | w/ Atten. | Factor |
| PNLIP_2 | 0.253 | 0.048 | 5.268 |
| PNLIP_1 | 0.203 | 0.035 | 5.871 |
| PRSS1_2 | 0.114 | 0.034 | 3.343 |
| CPA1_2 | 0.111 | 0.023 | 4.841 |
| CLPS_2 | 0.051 | 0.037 | 1.373 |
| Sum | 0.732 | 0.177 | |

Example 5 Elution and Preparation of Spatially Encoded Probes for Next Generation Sequencing Using the methods described supra, a 134-plex pool of probe pairs was hybridized to an FFPE sample, ligated and spatially encoded with X-positional and Y-positional adaptors. In preparation for elution, a hybridization chamber (Agilent) was applied to the slide and clamped in place to form a leakproof chamber containing the FFPE tissue sample. Using syringes, this chamber was filled with deionized water and the assembly was heated to 80° C. for 30 minutes after which time the eluate was removed using a syringe and transferred to a tube.

The spatially encoded constructs were purified by two rounds of positive selection using magnetic beads to isolate them from any un-encoded probes, leftover positional-encoding adaptors, or malformed constructs. In the first round of purification, the eluate was hybridized to a biotinylated capture probe comprising a sequence that was complementary to a sequence spanning the junction of the X positional adaptor (address tag) and the 5' end of the joined probe pair. This capture probe was then captured on streptavidin functionalized magnetic beads, which were then washed extensively to remove unbound material. Constructs hybridized to capture probes were then eluted by heating in an elution buffer containing a blocking oligonucleotide that was complementary to the capture probe. The eluate was separated from the magnetic beads using a magnet, transferred to a new container, and hybridized with a biotinylated capture probe comprising a sequence that was complementary to a sequence spanning the junction of the 3' end of the joined probe pair and the Y positional adaptor (address tag). This capture probe, together with hybridized constructs, was subsequently captured on streptavidin functionalized magnetic beads and washed.

The beads were transferred directly into a PCR mix that included primers comprising sequences that enable sequencing of the PCR products on an Illumina MiSeq instrument. The primers also comprised TruSeq barcodes to allow demultiplexing of multiple samples in a single sequencing run. A fraction of the PCR product was analyzed by gel electrophoresis to verify the presence of the amplified spatially encoded constructs. The remaining product was purified using a Qiagen PCR purification Kit. Finally, the spatially encoded constructs were purified by size selection using either a conventional gel electrophoresis device or the Pippen Prep System (Sage Science).

The purified encoded construct was sequenced using an Illumina MiSeq instrument and the data were used to generate expression maps.

Example 6 Spatially Encoded Protein In Situ Assays

This example describes a spatially encoded protein in situ assay. A highly multiplexable protein detection assay was carried out on a tissue microarray like the ones described supra containing a checkerboard pattern of liver and pancreas tissue cores. In this case a two-plex assay was encoded using a 5-site×5-site addressing scheme. The assay was performed by first applying a typical immunostaining procedure with two different primary antibodies, one specific to exocrine cells in the pancreas and one specific to hepatocytes in the liver. Two antibody-DNA conjugates were used as secondary antibodies and were applied to the entire tissue microarray. The conjugates included an oligonucleotide comprising an identity tag as well as an upstream and downstream splint region to allow ligation of X and Y address tags. After applying the primary antibody and secondary antibody conjugate to the entire sample and washing sufficiently, a pair of microfluidic channel devices was used to deliver sequentially the X and Y address tags, which were ligated to the oligonucleotide on the conjugate. The conjugates were eluted from the sample and the combined X and Y tags plus the intervening identity tag formed an amplifiable construct which was amplified, purified and subjected to next generation sequencing to identify the abundance of the antibody targets at each spatially encoded location.

Example 7 Spatially Encoded Protein In Situ Assays

This example describes a spatially encoded protein in situ assay. As shown in FIG. 6A, a highly multiplexable protein detection assay can be carried out on a sample that preserves the spatial organization of cells in a tissue, e.g., a paraffin-embedded or fresh-frozen tissue section fixed to a glass slide. Assay reagents are protein binders (e.g. antibodies) that are identified via linked DNA tags that can be further encoded with tag sequences that encode positional or address information (in this example, indicated as "X" dimension and "Y" dimension). The address tags X and Y are flanked by universal sequences (UP1 and UP2) that can be used as PCR priming sites, adaptors for next-generation sequencing, or both.

As shown in FIG. 6B, the binders, for example, the DNA-labeled antibody probes in this example, are delivered over the entire sample surface in a bulk process. The X and Y address tags are then delivered to the sample and coupled to the probes, so that the probes are encoded by the X and Y address tags in a spatially defined pattern. In this example, two sets of tags (i.e., a set of 10 X address tags, namely X1, X2, X3, . . . , X10, and a set of 10 Y address tags, namely Y1, Y2, Y3, . . . , Y10) are used in a combinatorial fashion, and 100 sites in the sample can be uniquely identified by the combinations of X and Y address tags. For example, a site in the sample shown in Figure XB is uniquely identified as (X9, Y1).

Once the in situ assay is completed, the assay products are eluted and sequenced. The address tag sequence information identifies the site at which the assay is performed, and the probe sequence information identifies the protein that is targeted. The frequency of a particular assay product in the digital readout can be used to infer the relative abundance of its target sequence in the sample. This information can then be associated with other information, including conventional histological information, and/or transcript abundance obtained via the related spatially encoded genomic assay.

Example 8 A Method to Reduce Background and Increase Signal-to-Noise Ratio

This example describes a method of detecting rare variant sequences in a mixed population of nucleic acids. The method can be integrated into the methods and assay systems disclosed herein, for example, to reduce the background contributed by random errors and thus to increase the signal to noise ratio (S/N).

Parallel clonal amplification methods in combination with digital sequencing have permitted large-scale analysis of variation at resolutions in the range of 1% (Druley et al., 2009, Nat. Methods 6: 263-65), but not much below. Although next-generation sequencing enables de novo discovery and holds great promise for deep analysis of variation across the genome, a combination of factors at various steps in the sequencing process have made it difficult to obtain very low error rates at readout. These factors include cross-talk between detection channels, incomplete reactions leading to signal loss, increased background as a result of loss in synchronicity of nucleotide addition, and noise and errors in image processing and signal extraction, which worsen significantly at higher sequencing densities. Thus the sequencing readout error rate is far above intrinsic rates exhibited by the high fidelity polymerases used in sequencing reactions. For example, an error rate of $4.4 \times 10^{-7}$ is estimated for Pfusion™ polymerase (New England Biolabs, Ipswich, Mass.). The method described in this example addresses the above technical issues, by using tags to identify target sequences that are "identical by descent." As illustrated in FIG. 11A, sequence reads can be partitioned into related groups on this basis.

FIG. 11A shows the concept of the rare variant assay, and FIG. 11B provides exemplary configurations of probes that can be used to integrate the rare variant assay in the spatially encoded assays of the present disclosure. The top panel of FIG. 11A shows a target sequence of interest flanked by adaptors that contain Illumina adaptor sequences for surface PCR (labeled a and b). The target can be obtained from a variety of sources, for example, a PCR amplicon. The adaptors contain a variable tag region (labeled z). Both strands are shown to illustrate that the Illumina adaptors are asymmetric. The tagged adaptors are used to construct libraries for sequencing. Single molecules are amplified to form "clusters" on the surface of a flowcell. Sequences are determined for each target region and its associated tag regions. In the final step shown, reads are grouped according to their tag regions, based on the assumption that reads with the same tag sequences are identical by descent, given that z is sufficiently long. The groupings are then analyzed to identify rare variant sequences (e.g. targets in the last set numbered 4 are shown in darker color compared to those in sets 1-3 to indicate that the target sequence differs from those in sets 1-3). Similar methods for rare variant sequence detection have been described in Fu et al., 2011, Proc. Natl. Acad. Sci., 108: 9026-9031, and in Schmitt et al., 2012, Proc. Natl. Acad. Sci., 109: 14508-14513, the disclosures of which are incorporated by reference herein for all purposes.

With this strategy, the contribution of random sequencing errors can be virtually eliminated. Therefore, barring contamination, the ability to detect a rare variant will be limited in theory by the sample size. Note that although the design shown in FIG. 11A references the Illumina adaptors and surface amplification methodology, the method is general and can be used with other sequencing platforms such as the SOLiD platform (Life Technologies), the 454 platform (Roche), and the Pacific Biosciences and Ion Torrent library constructions methods.

A model system was established to quantitate the improvements in the limit of detection over standard sequencing with the Illumina GAIIx instrument. The model system consisted of a wild-type 100-mer oligo and a mutant sequence containing a unique, single point mutation in the wild-type sequence. Synthetic oligos were cloned into an *E. coli* plasmid vector and individual clones were picked and sequence verified in order to obtain constructs that contained the desired sequences, providing pure, well defined sequence constructs free from oligonucleotide chemical synthesis errors (typically in the range of 0.3-1%). The 100-mer of interest was then excised from the plasmid clone by restriction digestion. Mutant and wild-type oligos were quantitated and mixed at ratios of 1:0, 1:20, 1:1000, 1:10,000, 1:100,000 and 1:1,000,000, and 0:1 to simulate the presence of a rare variant in a wild-type DNA background.

Next, custom adaptors containing random 10-mer tags were designed and synthesized. Libraries were prepared from the defined oligo mixtures, and sequenced on an Illumina GAIIx instrument according to the constructs and steps outlined in FIG. 11A. The data were first analyzed without utilizing the tag information (tag z as shown in FIG. 11A). This resulted in detection of the point mutation only in the 1:20 sample. A second round of analysis utilizing the tags was done using only high quality reads in which tag1/tag2 pairs were retained if the tags were grouped with each other >99% of the time and had ≥2 replicates. In order for a tag group to be scored as a mutation, at least 90% of reads in the group had to agree.

The mutant allele was also successfully detected in the 1:10,000, 1:100,000, and 1:1,000,000 samples as shown in Table 3. Mutant allele frequencies within a factor of 2 of the expected value were observed, and this difference was accounted for in dilution and pipetting error. The power to observe a mutation in the wild-type (negative control) sample with ~7.5 M tag groups is greater than 0.999. Therefore, the difference between the 1:1,000,000 spiked sample and the negative control was highly significant.

TABLE 3

Demonstration of ability to detect a mutant allele over ~6 orders of magnitude

| Mutant:WT | Number of Tag Groups Assayed | Number of Mutant Alleles Observed | Estimated Allele Frequency |
|---|---|---|---|
| 1:20 | 3,433 | 273 | 0.08 |
| 1:1,000 | 2,539 | 6 | 0.0024 |
| 1:10,000 | 157,431 | 26 | 1.65E−04 |
| 1:100,000 | 1,752,922 | 33 | 1.88E−05 |
| 1:1,000,000 | 4,186,545 | 5 | 1.19E−06 |
| (Negative Ctrl) 1:0 | 7,488,853 | 0 | 0 |

The power to observe a mutant with frequency f is $1-(1-f)^{\#tags}$, so additional sequencing depth can increase the detection power. The limit of detection in this model system is determined only by sample size and any background contamination that might be present.

This method can be used to distinguish in vitro amplification errors from rare variants present in the original sample. For example, a simple threshold that the mutation frequency within a tag group must be >0.9 can be used to exclude PCR amplification errors from the analysis. This is based on the observation that the expected fraction of copies containing an error at that particular location equals 0.5, conditional on the error occurring in the very first cycle and neglecting the chance of consecutive PCR errors at the same position. No tags in the negative control pass this criterion.

This method can be integrated into the methods and assay systems for determining a spatial pattern of a target abundance, expression, or activity, in order to reduce the background contributed by random errors and thus to increase the signal to noise ratio (S/N). Non-limiting exemplary configurations of probes that integrate the X and Y address tags and the variable tag region z are shown in FIG. 11B.

Example 9 Analysis of Brain Tissue

This example describes production of an at least 24-plex protein assay panel and confirmation of its tissue/cell-type specificity by correlation with fluorescent labeling and by analysis of tissue microarrays.

A set of 26 antigens is selected. These antigens are expressed in neurons, astrocytes, oligodendrocytes, microglia or proliferating cells, and antibodies that have been raised against the antigens are commercially available (Table 4). These antibodies have been successfully used, in conjunction with well-established staining techniques, to mark different cell types and regions within brain sections (Lyck, et al., 2008, J Histochem Cytochem 56, 201-21). For the purpose of the assay, it is necessary to avoid procedures for antibody binding that damage RNA.

Antigen accessibility is addressed by exploring systematically a range of "antigen retrieval" protocols and testing their compatibility with RNA. See, MacIntyre, 2001, Br J Biomed Sci. 58, 190-6; Kap et al., 2011, PLoS One 6, e27704; Inoue and Wittbrodt, 2011, PLoS One 6, e19713. A panel of antibody assays rather than any individual assay are explored to identify a suitable subset for use in a multiplexed panel.

The assay system is also validated by using spatially-encoded and conventional IHC fluorescence data and spatially encoded RNA data, applied to brain tissue. High-dimensional protein and mRNA data from 32×32 sites in sections of human brain tissue are generated and compared with published data and brain atlas data.

The Allen Brain Atlas (www.brain-map.org) can be used to select target genes for production of a panel of gene expression assays with high information content, using the methods and assay systems of the present disclosure. The "Differential Search" tool is used to interrogate the rich spatial expression dataset (generated by in situ hybridization), it is identified that ~200 genes are present at a range of abundances in at least one structure/compartment of the brain, and/or are strongly differentially expressed between the different structures/compartments. The selection is reviewed to incorporate any new information or criteria. Probes against the set of ~200 mRNAs are designed and tested for their performance in the multiplexed assay, using the online gene expression data as a reference.

Protein panels and RNA assay panels are applied simultaneously to analyze sections of normal human brain. For example, the abundance of at least 24 proteins and 192 mRNA analytes over a 32×32 grid of 50 μm pixels from sections of healthy human brain is analyzed. The results are used to generate a rich map of the brain's spatially-organized molecular terrain, and are amenable to analysis in various ways, including those that reveal:

1. The organization of brain into distinct sub-structures: both at the anatomical scale, and at the lower-level multi-cellular level;

2. Spatial variation in the representation of different cell types across the tissue (e.g. using sets of proteins/mRNAs known to be specific to particular cell types); and 3. The relation between mRNA and protein expression from the same gene at different tissue locations.

TABLE 4

Candidate proteins to differentiate brain tissues, which have been used in immunohistochemistry and have commercially available antibodies.

| Protein | Observed Specificity {Lyck, 2008} |
|---|---|
| b-tubulin III | Neuropil and neuronal bodies |
| CD11b | None |
| CD14 | Perivascular macrophages |
| CD34 | Endothelium and white blood cells |
| CD39 | Endothelium, astroglia, and macrophages |
| CD45 | Microglia, macrophages, and lymphocytes |
| CD68 | Microglia and macrophages |
| CD169 | Endothelial and perivascular macrophages |
| CNPase | Myelinated fibers and round cell bodies |
| GFAP | Astroglia in white matter and neocortex |
| HLA-DR | Microglia/macrophages and lymphocytes |
| Ki-67 | Perivascular space and sub-ventricular zone |
| MAP-2 | Neurons and proximal part of apical dendrites |
| MBP | Myelinated fibers |
| Nestin | Endothelial cells/vessel wall |
| NeuN | Neuronal cell bodies |
| Neurofilament | Neuronal cell processes |
| NG2 | None |
| Nkx-2.2 | None |
| NSE | Neuropil |
| O4 sulfatide | Myelinated fibers |
| PDGFa-R | None |
| p25a | Neuropil and round cell bodies |
| S100b | Astroglia in white matter and neocortex |

TABLE 4-continued

Candidate proteins to differentiate brain tissues, which have been used in immunohistochemistry and have commercially available antibodies.

| Protein | Observed Specificity {Lyck, 2008} |
|---|---|
| TOAD-64 | Neuropil |
| Vimentin | Astroglia and endothelial cells/vessel wall |

All headings are for the convenience of the reader and should not be used to limit the meaning of the text that follows the heading, unless so specified.

Citation of the above publications or documents is not intended as an admission that any of them is pertinent prior art, nor does it constitute any admission as to the contents or date of these publications or documents.

While various embodiments of the invention have been described above, it should be understood that they have been presented by way of example only, and not by way of limitation. Likewise, the various diagrams may depict an example architectural or other configuration for the disclosure, which is done to aid in understanding the features and functionality that can be included in the disclosure. The disclosure is not restricted to the illustrated example architectures or configurations, but can be implemented using a variety of alternative architectures and configurations. Additionally, although the disclosure is described above in terms of various exemplary embodiments and implementations, it should be understood that the various features and functionality described in one or more of the individual embodiments are not limited in their applicability to the particular embodiment with which they are described. They instead can, be applied, alone or in some combination, to one or more of the other embodiments of the disclosure, whether or not such embodiments are described, and whether or not such features are presented as being a part of a described embodiment. Thus the breadth and scope of the present disclosure should not be limited by any of the above-described exemplary embodiments.

We claim:

1. A method, comprising:
delivering a probe for a target protein to multiple sites in a sample, wherein the probe comprises: (1) a target-binding moiety capable of binding to the target protein; (2) a first address tag that identifies each of the multiple sites to which the probe is delivered; and (3) an identity tag that identifies the target protein or the target-binding moiety;
allowing the probe to bind to the target protein in the sample;
analyzing the probe bound to the target protein, the analysis comprising: (1) determining abundance, expression, and/or activity of the target protein by assessing the amount of the probe bound to the target protein; and (2) determining the identities of the identity tag and the first address tag of the probe for the target protein; and
determining a spatial pattern of abundance, expression, and/or activity of the target protein across the multiple sites in the sample based on the analysis,
the method further comprising:
delivering a probe for a target polynucleotide to each of the multiple sites in the sample, wherein the probe for the target polynucleotide comprises: (1) a sequence that hybridizes to and identifies the target polynucleotide; (2) a second address tag that identifies each of the multiple sites to which the probe for the target polynucleotide is delivered;
allowing the probe for the target polynucleotide to bind to the target polynucleotide in the sample;
analyzing the probe bound to the target polynucleotide, the analysis comprising: (1) determining abundance, expression, and/or activity of the target polynucleotide by assessing the amount of the probe bound to the target polynucleotide; and (2) determining the identities of the sequence that hybridizes to and identifies the target polynucleotide and the second address tag of the probe for the target polynucleotide; and
determining a spatial pattern of abundance, expression, and/or activity of the target polynucleotide across the multiple sites in the sample based on the analysis of the probe bound to the target polynucleotide at each of the multiple sites in the sample.

2. The method of claim 1, wherein the analyzing step is carried out by sequencing, wherein the amount of a sequencing product indicates abundance, expression, and/or activity of the target protein, the sequencing product comprising all or a portion of the first address tag sequence and all or a portion of the identity tag sequence.

3. A method, comprising:
delivering a probe for a target protein to multiple sites in a sample, wherein the probe comprises: (1) a target-binding moiety capable of binding to the target protein; and (2) an identity tag that identifies the target protein or the protein-binding moiety;
allowing the probe to bind to the target protein in the sample;
delivering a first address tag to each of the multiple sites in the sample, wherein the first address tag is to be coupled to the probe bound to the target protein and identifies the site to which it is delivered;
analyzing the probe/first address tag conjugate bound to the target protein, the analysis comprising: (1) determining abundance, expression, and/or activity of the target protein by assessing the amount of the probe/first address tag conjugate bound to the target protein; and (2) determining the identities of the identity tag and the first address tag of the probe/first address tag conjugate; and
determining a spatial pattern of abundance, expression, and/or activity of the target protein across the multiple sites in the sample based on the analysis,
the method further comprising:
delivering a probe for a target polynucleotide to each of the multiple sites in the sample, wherein the probe for the target polynucleotide comprises a sequence that hybridizes to and identifies the target polynucleotide;
allowing the probe for the target polynucleotide to bind to the target polynucleotide in the sample;
delivering a second address tag to each of the multiple sites in the sample, wherein the second address tag is to be coupled to the probe bound to the target polynucleotide and identifies the site to which it is delivered;
analyzing the probe/second address tag conjugate bound to the target polynucleotide, the analysis comprising: (1) determining abundance, expression, and/or activity of the target polynucleotide by assessing the amount of the probe/second address tag conjugate bound to the target polynucleotide; and (2) determining the identities of the sequence that hybridizes to and identifies the target polynucleotide and the second address tag of the probe/second address tag conjugate; and determining a spatial pattern of abundance, expression, and/or activity of the target polynucleotide across the multiple sites in the sample based on the analysis of the probe/second address tag conjugate bound to the target polynucleotide at each of the multiple sites in the sample.

4. The method of claim 3, wherein the target polynucleotide or the complement thereof encodes all or a portion of the target protein.

5. The method of claim 3, wherein the step of analyzing the probe or probe/first address tag conjugate bound to the target protein and the step of analyzing the probe or probe/second address tag conjugate bound to the target polynucleotide are performed in parallel in the same reaction run.

6. The method of claim 3, wherein the first address tag and the second address tag are the same for a given site of the multiple sites in the sample.

7. The method of claim 3, wherein the first address tag and the second address tag are different for a given site of the multiple sites in the sample.

8. The method of claim 3, further comprising associating abundance, expression, and/or activity of the target protein to abundance, expression, and/or activity of the target polynucleotide at each of the multiple sites in the sample.

9. The method of claim 3, wherein the target protein comprises an enzyme activity.

10. The method of claim 3, wherein the target-binding moiety of the probe comprises a moiety selected from the group consisting of an antibody or an antigen binding fragment thereof, an aptamer, a small molecule, an enzyme substrate, a putative enzyme substrate, an affinity capture agent, and a combination thereof.

11. The method of claim 3, wherein the target-binding moiety is conjugated to a polynucleotide comprising the identity tag.

12. The method of claim 3, wherein the target-binding moiety is conjugated to a polynucleotide capable of specifically hybridizing to a polynucleotide comprising the identity tag.

13. The method of claim 3, wherein the probe comprises a multiplicity of target-binding moieties capable of binding to the same domain or different domains of the target, or capable of binding to different targets.

14. The method of claim 3, wherein there are two address tags that identify each of the multiple sites in the sample.

15. The method of claim 3, wherein two probes for each target are delivered to the sample.

16. The method of claim 3, wherein the sample is a biological sample selected from the group consisting of a freshly isolated sample, a fixed sample, a frozen sample, an embedded sample, a processed sample, or a combination thereof.

17. The method of claim 3, wherein the address tag comprises an oligonucleotide.

18. The method of claim 3, wherein the identity tag comprises an oligonucleotide.

19. The method of claim 3, wherein the analyzing step is performed by nucleic acid sequencing or high-throughput sequencing.

20. The method of claim 3, wherein the product of the number of the target(s) being assayed is x and the number of the multiple sites being assayed in the sample is y, and the value of x×y is greater than 20, 50, 75, 100, 1,000, 10,000, 100,000, or 1,000,000.

21. The method of claim 3, wherein at least one hundred thousand, at least five hundred thousand, or at least one million probes or probe/address tag conjugates bound to the target(s) are analyzed in parallel.

22. The method of claim 3, wherein software programmed hardware performs at least two steps of the delivering step(s), the analyzing step(s) and the determining step(s).

23. The method of claim 3, wherein one or more microfluidic devices are used to perform the delivering step(s).

24. The method of claim 3, wherein a known percentage of the probe for the biological target, the probe for the target protein, or the probe for the target polynucleotide is an attenuator probe.

25. The method of claim 24, wherein the attenuator probe limits production of an amplifiable product.

26. The method of claim 24, wherein the attenuator probe lacks a 5' phosphate.

27. The method of claim 3, wherein the address tag is coupled to the probe by ligation or by extension or any combination thereof.

28. The method of claim 3, further comprising constructing a 3-dimensional pattern of abundance, expression, and/or activity of each target from spatial patterns of abundance, expression, and/or activity of each target of multiple samples.

29. The method of claim 28, wherein the multiple samples are consecutive tissue sections of a 3-dimensional tissue sample.

30. The method of claim 3, wherein the analyzing step is carried out by sequencing, wherein the amount of a sequencing product indicates abundance, expression, and/or activity of the target protein, the sequencing product comprising all or a portion of the first address tag sequence and all or a portion of the identity tag sequence.

* * * * *